US010350595B2

(12) United States Patent
Dimov et al.

(10) Patent No.: US 10,350,595 B2
(45) Date of Patent: Jul. 16, 2019

(54) METHODS AND APPARATUSES FOR SORTING TARGET PARTICLES

(71) Applicant: Orca Biosystems, Inc., Mountain View, CA (US)

(72) Inventors: Ivan K. Dimov, Mountain View, CA (US); Nathaniel Fernhoff, Menlo Park, CA (US); Lagnajeet Pradhan, Union City, CA (US)

(73) Assignee: Orca Biosystems, Inc., Menlo Park, CA (US)

( * ) Notice: Subject to any disclaimer, the term of this patent is extended or adjusted under 35 U.S.C. 154(b) by 0 days.

(21) Appl. No.: 16/044,166

(22) Filed: Jul. 24, 2018

(65) Prior Publication Data

US 2018/0353960 A1 Dec. 13, 2018

Related U.S. Application Data

(63) Continuation of application No. PCT/US2017/061414, filed on Nov. 13, 2017.
(Continued)

(51) Int. Cl.
*B01L 3/00* (2006.01)
*B01L 9/00* (2006.01)
(Continued)

(52) U.S. Cl.
CPC ....... *B01L 3/502715* (2013.01); *B01L 3/5088* (2013.01); *B01L 3/50853* (2013.01); *B01L 9/523* (2013.01); *G01N 15/1436* (2013.01); *G01N 21/6402* (2013.01); *G01N 21/6458* (2013.01); *G02B 21/16* (2013.01); *H01S 5/18388* (2013.01); *H01S 5/423* (2013.01);
(Continued)

(58) Field of Classification Search
CPC . H01S 5/18388; H01S 5/423; G01N 21/6402; G01N 21/6458; G01N 21/16; B01L 3/502715; B01L 3/50853
USPC .......................................................... 209/509
See application file for complete search history.

(56) References Cited

U.S. PATENT DOCUMENTS 4,115,535 A 9/1978 Giaever
4,731,337 A 3/1988 Luotola et al.
(Continued)

FOREIGN PATENT DOCUMENTS

CN 1030139 A 1/1989
CN 1032399 A 4/1989
(Continued)

OTHER PUBLICATIONS

Al et al. Engineering and characterizing monomeric fluorescent proteins for live-cell imaging applications. Nat Protoc 9:910-28 (2014).
(Continued)

*Primary Examiner* — Terrell H Matthews
(74) *Attorney, Agent, or Firm* — Wilson Sonsini Goodrich & Rosati

(57) ABSTRACT

This disclosure provides methods and apparatuses for sorting target particles. In various embodiments, the disclosure provides a cassette for sorting target particles, methods for sorting target particles, methods of loading a microchannel for maintaining sample material viability, methods of quantifying sample material, and an optical apparatus for laser scanning and particle sorting.

25 Claims, 40 Drawing Sheets

Related U.S. Application Data

(60) Provisional application No. 62/421,979, filed on Nov. 14, 2016.

(51) Int. Cl.
*G02B 21/16* (2006.01)
*G01N 15/14* (2006.01)
*G01N 21/64* (2006.01)
*H01S 5/183* (2006.01)
*H01S 5/42* (2006.01)

(52) U.S. Cl.
CPC .......... *B01L 2200/0605* (2013.01); *B01L 2300/0829* (2013.01); *G01N 2015/149* (2013.01)

(56) References Cited

U.S. PATENT DOCUMENTS

| | | | |
|---|---|---|---|
| 4,758,523 A | 7/1988 | Harjunmaa | |
| 4,777,145 A | 10/1988 | Luotola et al. | |
| 5,351,332 A | 9/1994 | Cook | |
| 5,538,848 A | 7/1996 | Livak et al. | |
| 5,639,606 A | 6/1997 | Willey | |
| 5,643,765 A | 7/1997 | Willey | |
| 5,846,717 A | 12/1998 | Brow et al. | |
| 5,876,978 A | 3/1999 | Willey et al. | |
| 5,962,223 A | 10/1999 | Whiteley et al. | |
| 5,985,557 A | 11/1999 | Prudent et al. | |
| 5,994,069 A | 11/1999 | Hall et al. | |
| 6,001,567 A | 12/1999 | Brow et al. | |
| 6,023,540 A | 2/2000 | Walt et al. | |
| 6,027,873 A | 2/2000 | Schellenberger et al. | |
| 6,090,543 A | 7/2000 | Prudent et al. | |
| 6,133,436 A | 10/2000 | Koester et al. | |
| 6,716,629 B2 | 4/2004 | Hess et al. | |
| 6,794,127 B1 | 9/2004 | Lafferty et al. | |
| 6,838,056 B2 | 1/2005 | Foster | |
| 6,866,824 B2 | 3/2005 | Lafferty et al. | |
| 6,964,872 B2 | 11/2005 | Sakurai et al. | |
| 7,122,384 B2 | 10/2006 | Prober et al. | |
| 7,264,972 B2 | 9/2007 | Foster | |
| 7,572,640 B2 | 8/2009 | Goix et al. | |
| 8,460,878 B2 | 6/2013 | Rissin et al. | |
| 8,460,879 B2 | 6/2013 | Rissin et al. | |
| 8,492,098 B2 | 7/2013 | Rissin et al. | |
| 8,632,768 B2 | 1/2014 | Ildstad et al. | |
| 9,314,764 B2 | 4/2016 | Hess et al. | |
| 9,395,359 B2 | 7/2016 | Walt et al. | |
| 9,452,184 B2 | 9/2016 | Ildstad et al. | |
| 9,523,076 B2 | 12/2016 | Schoenbrunn et al. | |
| 9,643,180 B2 | 5/2017 | Abrams et al. | |
| 9,657,290 B2 | 5/2017 | Dimov et al. | |
| 9,658,219 B2 | 5/2017 | Verschuren et al. | |
| 9,746,457 B2 | 8/2017 | Hare et al. | |
| 2002/0045270 A1 | 4/2002 | Schurenberg et al. | |
| 2002/0094533 A1 | 7/2002 | Hess et al. | |
| 2002/0155439 A1 | 10/2002 | Rodriguez et al. | |
| 2002/0176804 A1* | 11/2002 | Strand | B01J 19/0093 422/400 |
| 2003/0096220 A1 | 5/2003 | Lafferty et al. | |
| 2003/0156993 A1* | 8/2003 | Staats | B01L 3/502707 204/455 |
| 2003/0224531 A1* | 12/2003 | Brennen | B01L 3/5025 436/180 |
| 2005/0009101 A1* | 1/2005 | Blackburn | B01L 3/5027 435/7.1 |
| 2005/0196376 A1 | 9/2005 | Loomis | |
| 2006/0078998 A1 | 4/2006 | Puskas et al. | |
| 2007/0259448 A1 | 11/2007 | Rissin et al. | |
| 2008/0032401 A1 | 2/2008 | Edinger et al. | |
| 2008/0280285 A1* | 11/2008 | Chen | B01L 3/502715 435/5 |
| 2010/0300559 A1* | 12/2010 | Schultz | B01L 3/502738 137/561 A |
| 2010/0303687 A1* | 12/2010 | Blaga | B01L 3/50273 422/504 |
| 2011/0298883 A1 | 12/2011 | Ohyama | |
| 2012/0122149 A1 | 5/2012 | Kocagoz | |
| 2014/0011690 A1 | 1/2014 | Dimov et al. | |
| 2014/0273207 A1 | 9/2014 | Chan et al. | |
| 2014/0295421 A1 | 10/2014 | Link et al. | |
| 2014/0345364 A1 | 11/2014 | Lin et al. | |
| 2015/0011406 A1 | 1/2015 | Rich et al. | |
| 2016/0040123 A1 | 2/2016 | Kanemura et al. | |
| 2016/0199834 A1* | 7/2016 | Bransky | B01L 3/502715 435/309.1 |
| 2016/0215324 A1* | 7/2016 | Srinivasan | C12Q 1/18 |
| 2016/0244749 A1 | 8/2016 | Cochran et al. | |
| 2016/0245805 A1 | 8/2016 | Baer et al. | |
| 2016/0281061 A1 | 9/2016 | Beachley et al. | |
| 2016/0303564 A1* | 10/2016 | Gilbert | B01L 3/502746 |
| 2017/0000825 A1 | 1/2017 | Ildstad et al. | |
| 2017/0246277 A1 | 8/2017 | Schneck et al. | |
| 2017/0292915 A1 | 10/2017 | Dimov et al. | |

FOREIGN PATENT DOCUMENTS

| | | |
|---|---|---|
| CN | 1360638 A | 7/2002 |
| CN | 1491359 A | 4/2004 |
| CN | 102224260 A | 10/2011 |
| EP | 2163640 B1 | 12/2011 |
| EP | 2306191 B1 | 12/2012 |
| EP | 2606120 B1 | 10/2015 |
| EP | 3037522 A1 | 6/2016 |
| JP | H0750113 B2 | 5/1995 |
| JP | 2004510996 A | 4/2004 |
| JP | 2010512534 A | 4/2010 |
| WO | WO-1986004684 | 8/1986 |
| WO | WO-1987007386 | 12/1987 |
| WO | WO-2000063404 | 10/2000 |
| WO | WO-2001038583 | 5/2001 |
| WO | WO-2002031203 | 4/2002 |
| WO | WO-2004004637 A2 | 1/2004 |
| WO | WO-2004044232 A1 | 5/2004 |
| WO | WO-2006110098 A1 | 10/2006 |
| WO | WO-2007035586 A2 | 3/2007 |
| WO | WO-2007098148 A2 | 8/2007 |
| WO | WO-2012007537 A1 | 1/2012 |
| WO | WO-2014008056 | 1/2014 |
| WO | WO-2016133907 A1 | 8/2016 |
| WO | WO-2016134370 A1 | 8/2016 |
| WO | WO-2018053485 A1 | 3/2018 |
| WO | WO-2018089953 A1 | 5/2018 |

OTHER PUBLICATIONS

Anderson et al., Memory CD4+ T cells do not induce graft-versus-host disease, The Journal of Clinical Investigation 112(1):101-108, 2003.

Andersson et al. Micromachined flow-through filter-chamber for chemical reactions on beads. Sensors and Actuators 37:203-208 (2000).

Bao et al. A microfluidic device for physical trapping and electrical lysis of bacterial cells. Applied Physics Letters 92:1-2(2008).

Chalfie, et al. Green fluorescent protein as a marker for gene expression. Science 1994. 263(5148):802-805.

Chao et al. Isolating and engineering human antibodies using yeast surface display. Nature protocols 1:755-768 (2006).

Chen et al., High-throughput analysis and protein engineering using microcapillary arrays, Nature Chemical Biology 12:76-81, 2016. Published Dec. 7, 2015. (9 pages).

De Freitas et al. Pulsatile dynamic stiffness of cartilage-like materials and use of agarose gels to validate mechanical methods and models. 78B(2):347-357 (2006).

EP13813011.7 Extended European Search Report dated Jun. 24, 2016.

Fitzgerald et al. Exploiting Highly Ordered Subnanoliter Volume Microcapillaries as Microtools for the Analysis of Antibody Producing Cells. Anal Chem 87:997-1003 (2015). Published Dec. 5, 2014.

(56) References Cited

OTHER PUBLICATIONS

Galajda et al. A Wall of Funnels Concentrates Swimming Bacteria. Journal of Bacteriology 189:8704-8707 (2007).
Groisman et al. A microfluidic chemostat for experiments with bacterial and yeast cells. Nature Methods 2:685-689 (2005).
Heim et al. Improved green fluorescence. Nature 373:663-664 (1995).
Huft et al. Three-dimensional large-scale microfluidic integration by laser ablation of interlayer connections. Lab Chip 10:2358-2365 (2010).
Kielberg et al. Tech Note No. 14 from Cryopreservation of Mammalian Cells, Thermo Scientific (2010).
Laurell et al. Chip integrated strategies for acoustic separation and manipulation of cells and particles. Chem. Soc. Rev. 36:492-506 (2007).
Lim et al. Bead-based microfluidic immunoassays: The next generation. Biosensors and Bioelectronics 22:1197-1204 (2007).
Mandal et al. Encapsulation of Magnetic and Fluorescent Nanoparticles in Emulsion Droplets. Langmuir 21:4175-4179 (2005).
Miraglia, et al. Homogeneous Cell- and Bead-Based Assays for High Throughput Screening Using Fluorometric Microvolume Assay Technology. 1999, J. of Biomol. Screen. 4: 193-204.
Murakami et al. On-chip micro-flow polystyrene Bead-based immunoassay for quantitative detection of tacrolimus (FK506). Analytical Biochemistry 334:111-116.
PCT/US2013/047792 International Search Report dated Jan. 16, 2014.
PCT/US2016/018954 International Search Report dated Jun. 24, 2016.
PCT/US2017/052218 International Search Report dated Dec. 5, 2017.
PCT/US2017/061414 International Search Report dated Mar. 8, 2018.
Hu et al. Engineering of a fungal ß-galactosidase to remove product inhibition by galactose. Appl Microbiol Biotechnol 87:1773-1782 (2010).
O'Brien et al. Functional Interrelationships in the Alkaline Phosphatase Superfamily: Phosphodiesterase Activity of *Escherichia coli* Alkaline Phosphatase. Biochemistry 40:5691-5699 (2001).
Kariolis et al. An engineered Axl 'decoy receptor' effectively silences the Gas6/Axl signaling axis Nat Chem Biol 10:977-983 (2014).
Shaner et al. Improved monomeric red, orange and yellow fluorescent proteins derived from *Discosoma* sp. red fluorescent protein. Nat Biotechnol. 22:1567-1572 (2014).
Albertstein et al. Removing allosteric feedback inhibition of tomato 4-coumarate:CoA ligase by directed evolution. Plant J 69:57-69 (2012).
Alford et al. A Fluorogenic Red Fluorescent Protein Heterodimer. Chem Biol 19:353-60 (2012).
Alford et al. Dimerization-Dependent Green and Yellow Fluorescent Proteins. ACS Synth Biol 1:569-575 (2012).
Andrews et al. Probing the Origins of Catalytic Discrimination between Phosphate and Sulfate Monoester Hydrolysis: Comparative Analysis of Alkaline Phosphatase and Protein Tyrosine Phosphatases. Biochemistry 53:6811-6819 (2014).
Brune et al. Direct, Real-Time Measurement of Rapid Inorganic Phosphate Release Using a Novel Fluorescent Probe and Its Application to Actomyosin Subfragment 1 ATPase. Biochemistry 33:8262-8271 (1994).
EP16753225.8 Extended European Search Report dated Jun. 21, 2018.
Fischlechner et al. Evolution of enzyme catalysts caged in biomimetic gel-shell beads. Nat Chem 6:791-796 (2014).
Huse et al. Application of a Filamentous Phage pVIII Fusion Protein System Suitable for Efficient Production, Screening and Mutagenesis of F(ab) Antibody Fragments. J. Immunol 149:3914-3920 (1992).
Wolf et al. Quantitative Analysis of Digital Microscope Images. Methods Cell Biol 114:337-367 (2007).
Yang et al. Rational Engineering of Enzyme Allosteric Regulation through Sequence Evolution Analysis. PLoS Comput Biol 8:e1002612 (2012).
Steinberg et al. Early Keratinocyte Differentiation on Micropillar Interfaces.Nano Letters 7(2):287-294 (2007).
Thompson et al. Polymeric microbead arrays for microfluidic applications. J Micromech Microeng 20:1-8 (2010).
U.S. Appl. No. 13/791,967 Notice of Allowance dated Feb. 13, 2017.
U.S. Appl. No. 13/791,967 Notice of Allowance dated Jan. 10, 2017.
U.S. Appl. No. 13/791,967 Office Action dated Dec. 9, 2015.
U.S. Appl. No. 13/791,967 Office Action dated May 24, 2016.
U.S. Appl. No. 15/050,130 Office Action dated Jun. 11, 2018.
U.S. Appl. No. 15/050,142 Office Action dated Dec. 14, 2017.
U.S. Appl. No. 15/050,142 Office Action dated May 15, 2018.
U.S. Appl. No. 15/050,130Office Action dated Nov. 1, 2017.
Van Deventer, et al., Yeast Surface Display for Antibody Isolation: Library Construction, Library Screening, and Affinity Maturation, Monoclonal Antibodies: Methods and Protocols, Methods in Molecular Biology, Springer Science, Business Media New York 2014 1131:151-81.
Xia et al. Combined microfluidic-micromagnetic separation of living cells in continuous flow. Biomed Microdevices 8:299-308 (2006).
Zaytseva et al. Development of a microfluidic biosensor module for pathogen detection. Lab Chip 5:805-811 (2005).
Zinchenko et al. One in a Million: Flow Cytometric Sorting of Single Cell-Lysate Assays in Monodisperse Picolitre Double Emulsion Droplets for Directed Evolution. Anal. Chem. 86:2526-2533 (2014).

* cited by examiner

METHODS AND APPARATUSES FOR SORTING TARGET PARTICLES

CROSS-REFERENCE

This application is a continuation application of International Patent Application No. PCT/US2017/061414, filed on Nov. 13, 2017, which application claims priority to U.S. Provisional Application 62/421,979, filed on Nov. 14, 2016, the content of each of which is incorporated herein by reference.

BACKGROUND OF THE INVENTION

Through conventional technologies, biological material may be screened for biological components, such as cells, antibodies, proteins, peptides, and nucleic acids. However, a number of challenges in the identification, isolation and characterization of biological components still remain. For example, some devices and methods require multiple, time-consuming selection steps. Additionally, some devices and methods fail to prevent sample contamination, fail to accurately detect multiple positive signals, fail to isolate viable cells, fail to detect cells, and fail to differentiate a single cell from multiple cells. Some devices and methods are also limited in the number of cells that can be screened with reasonable expediency.

Accordingly, there is a current need in the art for new methods and apparatuses for identifying, isolating, sorting and characterizing biological material, in particular cellular material. The present disclosure addresses this deficiency with new methods and apparatuses for sorting viable cellular material as well as other target particles.

SUMMARY OF THE INVENTION

The present disclosure provides new methods and apparatuses for sorting target particles, including viable cellular material, and the products thereof.

In some aspects, the disclosure provides a cassette for detecting and sorting target particles, the cassette comprising a substrate with a first surface and a second surface and a plurality of microchannels extending from the first surface to the second surface, a first housing configured to receive the substrate wherein the first housing comprises an internal surface to receive a target particle released from the substrate, a second housing coupled to the first housing in a manner wherein the first and second housing together encapsulate the substrate and wherein the first or second housing further comprises a first fill port, and a transmissive portion located in one or each of the first housing and the second housing, wherein the transmissive portion permits transmission of electromagnetic radiation from outside of the cassette to the substrate.

In certain embodiments, the transmissive portion is at least partially transparent to a wavelength in the range of about 250 nm to 1600 nm. In certain embodiments, the transmissive portion is located in the first housing. In some embodiments, the transmissive portion is located in the second housing.

In certain embodiments, the first fill port is configured to receive a sample material mixture into the cassette. In certain embodiments, the first housing comprises the first fill port. In some embodiments, the second housing comprises the first fill port.

In certain embodiments, the first or second housing further comprises a release port. In certain embodiments, the release port is in fluid communication with the internal surface to permit transfer of the target particles out of the release port in the cassette. In certain embodiments, the first housing comprises the release port. In some embodiments, the second housing comprises the release port.

In certain embodiments, the second housing is positioned on top of the first housing. In certain embodiments, the first housing is positioned in a substantially parallel plane relative to the second housing.

In some aspects, the disclosure provides a cassette for detecting and sorting target particles, the cassette comprising a substrate with a first surface and a second surface and a plurality of microchannels extending from the first surface to the second surface, a first housing configured to receive the substrate wherein the first housing comprises an internal surface to receive a target particle released from the substrate, a second housing coupled to the first housing in a manner wherein the first and second housing together encapsulate the substrate, and wherein the first or second housing further comprises a first fill port for introducing a target particle mixture into the cassette and wherein the first or second housing further comprises a release port for releasing target particles from the cassette.

In certain embodiments, the first housing comprises the first fill port. In some embodiments, the second housing comprises the first fill port.

In certain embodiments, the first housing comprises the release port. In some embodiments, the second housing comprises the release port.

In certain embodiments, the cassette further comprises a transmissive portion located in one or each of the first housing and the second housing, wherein the transmissive portion permits transmission of electromagnetic radiation from outside of the cassette to the substrate. In certain embodiments, the transmissive portion is at least partially transparent to a wavelength in the range of about 250 nm to 1600 nm.

In certain embodiments, the second housing is positioned on top of the first housing. In certain embodiments, the first housing is positioned in a substantially parallel plane relative to the second housing. In various embodiments, the first housing and second housing are coupled irreversibly as a single housing unit. In some embodiments, the first and second housing are coupled to one another in a reversible manner.

In certain embodiments, the substrate comprises glass. In certain embodiments, the plurality of microchannels is positioned substantially in parallel to each other. In certain embodiments, the plurality of microchannels is from about 1 million to about 100 billion microchannels. In certain embodiments, the plurality of microchannels has an average internal diameter of about 50 nm to about 500 µm. In certain embodiments, the distance from the first surface to the second surface of the substrate is on average from about 10 µm to about 1 mm. In certain embodiments, the substrate further comprises border elements which extend vertically from the perimeter of the first surface of the substrate and permit containment of fluid on the first surface of the substrate.

In certain embodiments, the cassette further comprises a sample well in fluid communication with the first fill port, wherein the sample well is configured to load a sample material mixture into the microchannels of the substrate. The sample well may be in contact with the first surface of the substrate. The sample well may be movable across the first surface of the substrate. In certain embodiments, the sample well is movable manually, mechanically, or electronically.

In certain embodiments, the first or second housing further comprise a second fill port. The first or second fill port may be in fluid communication with the internal surface of the first housing. In certain embodiments, the first or second housing further comprise a third fill port. In certain embodiments, the cassette further comprises a hydration membrane positioned to contact the substrate or positioned adjacent to the substrate. The first, second, or third fill port may be in fluid communication with the hydration membrane. In certain embodiments, the first and second housing prevent contaminant entry into the cassette. In certain embodiments, the internal surface further comprises a collection well. The collection well may be in fluid communication with the release port.

In certain embodiments, the first or second housing further comprises a metal frame which is affixed to the first or second housing and the first or second surface of the substrate and applies tension across the surface of the substrate. In certain embodiments, the substrate comprises a first end, a second end and a middle portion, wherein the first end, the second end and the middle portion are all substantially within the same plane.

In certain embodiments, the target particles comprise cells. In certain embodiments, the cassette is sterilized before use.

In certain embodiments, the substrate has dimensions of 3 mm×3 mm×0.3 mm to 5000 mm×15000 mm×1000 mm. In certain embodiments, the substrate has dimensions of 3 mm×3 mm×0.3 mm to 10000 mm×10000 mm×100 mm.

In certain embodiments, the cassette further comprises a contact transducer in contact with one or more components of the cassette.

In some aspects, the disclosure provides a substrate comprising a first surface and a second surface and a plurality of microchannels extending from the first surface to the second surface, wherein the microchannels comprise target particles and opaque material wherein at least about 50% of the target particles are separated from the opaque material by at least about 1 µm by a spacer comprising a transparent gel or transparent solid or combination thereof. In certain embodiments, at least about 50% of the target particles are separated from the opaque material by at least about 1 µm by a spacer comprising a transparent gel or transparent solid, such as agarose, collagen, matrigel, alginate, and combinations thereof.

In some aspects, the disclosure provides a kit comprising a cassette of the present disclosure and instructions for use thereof in the detection and sorting of target particles.

In some aspects, the disclosure provides a method of detecting and sorting target particles, the method comprising adding a sample material mixture into the cassette of the present disclosure, loading the sample material mixture into the microchannels of the substrate, scanning the contents of the microchannels to detect microchannels containing one or more target particles, and releasing the target particles from the substrate to the internal surface.

In certain embodiments, the sample material mixture is added into the cassette through the first fill port. The sample material mixture may be added to the sample well. In some embodiments, the sample material mixture is added to the substrate. In certain embodiments, the sample material mixture comprises a cellular suspension. The sample material mixture comprises about $1 \times 10^6$ to about $100 \times 10^9$ cells. The sample well may load an approximately equivalent amount of the sample material mixture in each microchannel of the substrate.

In certain embodiments, scanning the microchannels comprise illumination of a microchannel with a first wavelength and detection of a second wavelength from the microchannel, wherein the second wavelength corresponds with the target particles. Scanning the contents of the microchannels may comprise illumination of a microchannel with a plurality of different wavelengths and detecting an emission from the microchannel wherein the emission corresponds with one or more target particles. In certain embodiments, the scanning the contents of the microchannels comprise illumination of a microchannel with a single wavelength and detection of a plurality of emissions from the microchannel, wherein the plurality of emissions correspond with one or more target particles. In some embodiments, the scanning the contents of the microchannels comprises illumination of a microchannel with a plurality of different wavelengths and detection of a plurality of emissions from the microchannel, wherein one or more of the emissions correspond with one or more target particles. In certain embodiments, the first and second wavelengths are independently selected from about 200 nm to about 1.5 mm.

In certain embodiments, the target particle is released from the substrate to the internal surface with an energy from a third wavelength. In certain embodiments, the third wavelength is selected from about 200 nm to about 1.5 mm, such as from about 350 nm to about 1200 nm. In certain embodiments, the target particle is a cell.

In certain embodiments, following the release step, the method further comprises a step of transferring the target particle from the internal surface to the release port. In certain embodiments, transferring the target particle from the internal surface to the release port comprises adding a solution to the first or second fill port to transfer the target particle to the release port. The solution may be a buffer solution.

In certain embodiments, the method further comprises a step of sonicating the substrate, wherein the sonication step occurs prior to the scanning step. The sonication step may occur prior to, concurrent with, or subsequent to the loading step or a combination thereof. In certain embodiments, the sonication step comprises contacting the substrate with a contact transducer.

In some aspects, the disclosure provides a method of loading a mixture into a microchannel of substrate comprising a plurality of microchannels, the method comprising adding a first mixture to microchannels of a substrate, wherein the first mixture comprises a transparent solution and a plurality of opaque particles, and adding a second mixture to microchannels of a substrate, wherein the second mixture comprises a sample component and an aqueous solution.

In certain embodiments, the transparent solution comprises a gelling agent, such as natural gums, starches, pectins, agar-agar, gelatin, or a combination thereof. In certain embodiments, the method further comprises allowing the first mixture to solidify prior to the addition of the second mixture. In certain embodiments, the method further comprises a step of adding a reagent to remove a portion of the first mixture from the microchannels following the addition of the first mixture to the microchannels and prior to addition of the second mixture to the microchannels.

In certain embodiments, the sample component is a cell. In certain embodiments, the plurality of opaque particles absorb radiation at a fourth wavelength. In certain embodiments, the fourth wavelength is selected from about 250 nm to about 1.5 mm. In certain embodiments, 90% or more of the plurality of opaque particles are not in contact with the sample component in the microchannels. In certain embodiments, the plurality of opaque particles are separated from the sample component by a distance of at least about 1 µm or more in the microchannels.

In some aspects, the disclosure provide a method of loading a mixture into a microchannel of substrate comprising a plurality of microchannels, the method comprising adding a sample component and a particle to the microchannel of the substrate, wherein the particle comprises an opaque core and a shell surrounding the core.

In certain embodiments, the shell comprises a transparent material, such as a gel. In certain embodiments, the sample component comprises a cell. In certain embodiments, the sample component and particle are sequentially added to the microchannel of the substrate. In some embodiments, the sample component and particle are added simultaneously to the microchannel of the substrate. In certain embodiments, the opaque core comprises a magnetic bead.

In some aspects, the disclosure provides a method of loading a mixture into a microchannel of substrate comprising a plurality of microchannels, the method comprising first adding to a microchannel a sample component and a plurality of first particles that do not absorb a wavelength $X_1$, and second, adding to the microchannel a plurality of second particles which absorb a wavelength $X_1$ to the microchannel. In certain embodiments, the plurality of second opaque particles comprise magnetic beads.

In some aspects, the disclosure provides a method of loading a sample mixture into a microchannel of substrate comprising a plurality of microchannels, the method comprising adding to a microchannel a sample material mixture comprising a target particle, a plurality of magnetic particles and a plurality of non-magnetic particles, and applying a magnetic force above or below the plurality of microchannels to attract the magnetic particles to form a layer above or below the non-magnetic particles.

In certain embodiments, after applying the magnetic force, 50% or more of the magnetic particles are not in contact with the target particle. In certain embodiments, after applying the magnetic force, 50% or more of the magnetic particles are separated from the sample component by at least about 1 µm or more.

In certain embodiments, the non-magnetic particles are selected from particles comprising silica, agarose, polystyrene or a combination thereof. In certain embodiments, the target particles comprise intact or lysed cells. In certain embodiments, the weight ratio of magnetic particles to the non-magnetic particles in the sample material mixture is from about 1:0.5 to about 1:10. In certain embodiments, the concentration of magnetic particles in the sample material mixture is about 1 mg/mL to about 30 mg/mL. In certain embodiments, the concentration of non-magnetic particles in the sample material mixture is about 1 mg/mL to about 100 mg/mL.

In some aspects, the disclosure provides a method of quantifying the number of target particles in a microchannel of a substrate, the method comprising first adding a sample mixture into a microchannel of a substrate, subsequent to adding the sample mixture, adding particles labeled with a fluorescent material to the microchannels of the substrate, and quantifying the number of target particles in the microchannels.

In certain embodiments, quantifying the number of target particles in the microchannels is performed using microscopy. In certain embodiments, the particles are opaque beads. The opaque beads may be selected from Dynabead, Agarose, and ProMag. In certain embodiments, the particles are added about 5 minutes or more after the sample mixture is added to the microchannels. In certain embodiments, the target particles comprise a cell.

In some aspects, the disclosure provides a method of quantifying the number of target particles in a microchannel of a substrate, the method comprising adding a sample mixture comprising target particles into a microchannel of a substrate, adding a fluorescent material to the microchannels of the substrate, and quantifying the number of target particles in the microchannels by detecting the fluorescence emitted from the microchannels, wherein the intensity of fluorescence emitted is correlated to target particle count.

In certain embodiments, the fluorescent material is in solution. In certain embodiments, the sample mixture and fluorescent material are added concurrently to the microchannels. The fluorescent material may be associated with the target particles. In certain embodiments, high emitted fluorescence is correlated with low target particle count or no target particle count and low emitted fluorescence is correlated with high target particle count. In certain embodiments, the target particle is a cell.

In some aspects, the disclosure provides a cassette for detecting and sorting target particles, the cassette comprising a substrate with a first surface and a second surface, wherein the second surface is configured to adhere a sample material mixture to the second surface, a first housing configured to receive the substrate wherein the first housing comprises an internal surface to receive a target particle released from the substrate, a second housing coupled to the first housing in a manner wherein the first and second housing together encapsulate the substrate and wherein the first or second housing further comprises a first fill port, and a transmissive portion located in one or each of the first housing and the second housing, wherein the transmissive portion permits transmission of electromagnetic radiation from outside of the cassette to the substrate.

In certain embodiments, the second surface of the substrate is at least partially coated to increase sample material mixture adhesion to the second surface. In certain embodiments, the second surface of the substrate is at least partially coated to increase target particle adhesion to the second surface. In certain embodiments, the substrate comprises glass.

In some aspects, the disclosure provides an apparatus to sort target particles, the apparatus comprising an excitation light source to emit an excitation beam to generate fluorescence light from target particles located on a surface or in a plurality of channels, a detector to receive fluorescence light from the target particles, an extraction laser to provide an extraction beam to remove target particles from the surface or a plurality of channels, a scanner coupled to the extraction beam to scan the excitation beam and the extraction beam to the surface or plurality of channels, and circuitry coupled to the detector and the extraction beam to selectively remove target particles in response to fluorescence detected from the surface or channels, wherein the apparatus is configured to process the surface or plurality of channels at a rate within a range from about 5,000 to about 100,000,000 target particles per second.

In certain embodiments, the apparatus comprising an excitation light source to emit an excitation beam to generate fluorescence light from target particles located on a surface, a detector to receive fluorescence light from the target particles, an extraction laser to provide an extraction beam to remove target particles from the surface, a scanner coupled to the extraction beam to scan the excitation beam and the extraction beam to the surface, and circuitry coupled to the detector and the extraction beam to selectively remove target particles in response to fluorescence detected from the surface, wherein the apparatus is configured to process the surface at a rate within a range from about 5,000 to about 100,000,000 target particles per second.

In certain embodiments, the apparatus comprising an excitation light source to emit an excitation beam to generate fluorescence light from target particles located in a plurality of channels, a detector to receive fluorescence light from the target particles, an extraction laser to provide an extraction beam to remove target particles from a plurality of channels, a scanner coupled to the extraction beam to scan the excitation beam and the extraction beam to plurality of channels, and circuitry coupled to the detector and the extraction beam to selectively remove target particles in response to fluorescence detected from the channels, wherein the apparatus is configured to process the plurality of channels at a rate within a range from about 5,000 to about 100,000,000 target particles per second.

In certain embodiments, the circuity, the extraction laser and the detector are configured to process the surface or plurality of channels at a rate within the range from about 25,000 to about 20,000,000 target particles per second. The scanner may be optically coupled to the excitation beam and the extraction beam to scan the excitation beam and the extraction beam together along the surface or plurality of channels.

In certain embodiments, the scanner, the excitation beam, and the extraction beam are arranged with optics to scan the excitation beam and the extraction beam to the surface or plurality of channels with the excitation beam separated from the extraction beam. In some embodiments, the scanner, and a plurality of extraction beams are arranged with optics to scan the extraction beams to the surface or plurality of channels with the extraction beams separated from each other and independently modulated. In certain embodiments, the optics are configured to simultaneously focus the excitation beam to a first location on the surface or a first channel of the plurality of channels and the extraction beam to a second location on the surface or a second channel of the plurality of channels, wherein the first location is separated from the second location by a distance within a range from about 100 µm to about 5 mm and optionally wherein the distance is within a range from about 250 µm to about 1 mm. In certain embodiments, wherein the optics, the scanner, the excitation beam, and the extraction beam are arranged to simultaneously focus the excitation beam to a first location on the surface or a first channel of the plurality of channels and the extraction beam to a second location on the surface or a second channel of the plurality of channels, wherein the first location is separated from the second location by a distance within a range from about 100 µm to about 1 mm.

In certain embodiments, the scanner comprises one or more substantially flat mirror surfaces, and wherein the excitation beam and the extraction beam are arranged to reflect together from each of the plurality of substantially flat mirror surfaces.

In certain embodiments, the scanner comprises a first scanner to reflect and scan the excitation beam and a second scanner to reflect and scan the extraction beam, wherein the circuitry is configured to coordinate scanning of the excitation beam with the first scanner and scanning of the extraction beam with the second scanner along the array to selectively remove target particles from the surface or plurality of channels.

In certain embodiments, the first scanner and the second scanner are located on one side of a substrate defining the surface or the plurality of channels. In some embodiments, the first scanner and the second scanner are located on opposite sides of a support defining the surface or the plurality of channels. In certain embodiments, the first scanner and the second scanner are independently selected from the group consisting of a polygonal scanner, a galvanometer scanner, an acousto optic modulator, digital light processing system (DLPS) and a resonant scanner. In certain embodiments, the scanner is selected from the group consisting of a polygonal scanner, a galvanometer scanner and an acousto optic modulator.

In certain embodiments, the circuitry and the detector are configured to detect fluorescence of a target particle above a threshold amount in each location of the surface or each channel of the plurality of channels and, based on the fluorescence response, to selectively irradiate each location of the surface or each channel the plurality of channels, wherein the length of time elapsing between the fluorescence and the irradiation lies within a range from about 10 ns to about 100 µs, optionally within a range from about 100 ns to about 10 µs. In certain embodiments, the excitation light source, the extraction laser, and the circuitry are synchronized to a shared clock. In certain embodiments, the excitation light source is configured to emit a plurality of wavelengths, each of the plurality of wavelengths comprising a peak separated from other peaks of the plurality of wavelengths. The excitation light source may be selected from the group consisting of LEDs and lasers. In certain embodiments, the optics comprise an objective lens and wherein the excitation source, the objective lens, and the detector are arranged in a confocal configuration.

In certain embodiments, the objective lens comprises an F-theta optic. In certain embodiments, the scanner comprises a mirror and the optics are arranged to focus the excitation beam to a location of the surface through the objective lens with the mirror at a first angle and to transmit first fluorescent light from a first target particle in the location of the surface to the detector through the objective lens with the mirror at the first angle and wherein the optics are arranged to focus the excitation beam to a second location of the surface through the objective lens with the mirror at a second angle and to transmit fluorescent light from a second target particle at the second location of the surface to the detector through the objective lens with the mirror at the second angle, in order to scan the excitation beam to a plurality of locations on the surface and measure fluorescence from the plurality of locations on the surface with the confocal configuration.

In certain embodiments, the scanner comprises a mirror and wherein the optics are arranged to focus the excitation beam to a first channel of the plurality of channels through the objective lens with the mirror at a first angle and to transmit first fluorescent light from a first target particle in the first channel of the plurality of channels to the detector through the objective lens with the mirror at the first angle and wherein the optics are arranged to focus the excitation beam to a second channel of the plurality of channels through the objective lens with the mirror at a second angle and to transmit fluorescent light from a second target particle in the second channel of the plurality of channels to the detector through the objective lens with the mirror at the second angle, in order to scan the excitation beam to a plurality of channels and measure fluorescence from the plurality of channels with the confocal configuration.

In certain embodiments, the optics are arranged to transmit the excitation beam coaxially with a field of view of the detector through the objective lens. In certain embodiments, a field of view of the detector is no more than about 100 mm along a surface of a substrate defining the surface or the plurality of channels when the excitation beam is focused on a location of the surface or a channel of the plurality of channels and optionally wherein the beam is configured to utilize diffuse infinite conjugate excitation light. In certain embodiments, the detector comprises a field of view at the surface or the plurality of channels, and wherein a full width half maximum cross-sectional size of the beam at the surface or the plurality of channels is no more than the field of view at the surface or the plurality of channels and optionally wherein the full width half maximum cross-sectional size is no more than about half of the field of view. In certain embodiments, the field of view of the detector is defined with an optical structure selected from the group consisting of an aperture, a dimension across the aperture, a pinhole, mirror, and a maximum dimension across a reflective surface across a mirror.

In certain embodiments, the detector comprises a plurality of detectors and wherein a field of view of each of the plurality of detectors is arranged in the confocal configuration with the excitation beam. In certain embodiments, the excitation beam comprises a plurality of overlapping excitation beams and wherein each of the plurality of excitation beams is arranged in the confocal configuration with the detector. In certain embodiments, the excitation beam comprises a first excitation beam and a second excitation beam and wherein a first field of view of a first detector is confocal with the first excitation beam and a second field of view of a second detector is confocal with the second excitation beam.

In certain embodiments, a maximum cross-sectional dimension of each of the plurality of channels is within a range from about 10 µm to about 100 µm in order to contain a single target particle. In certain embodiments, the circuitry is configured to pulse the extraction beam in response to fluorescence of a target particle with an amount of energy sufficient to extract the target particle from the surface or the channel and allow the target particle to survive and optionally wherein an amount of energy to extract the target particle within a range from about 0.1 µJ to about 1000 µJ. In certain embodiments, the circuitry is configured to generate a plurality of pulses to extract a plurality of target particles, and wherein an amount of extraction energy to each extracted target particle is within a range from about 1 µJ to about 50 µJ and wherein a duration of the extraction energy to the each extracted target particle is within a range from about 0.1 ns to about 1000 ns and wherein a peak extraction power to the each of the plurality of extracted target particles is within a range from about 0.1 W to about $10^7$ W.

In some aspects, the disclosure provides an apparatus to sort target particles, the apparatus comprising an objective lens to direct light onto a plurality of channels sized to contain the target particles, a light source to generate an excitation beam, the light source optically coupled to the objective lens to generate fluorescence from the target particles contained in the plurality of channels, a two dimensional array detector optically coupled to the objective lens to receive fluorescence light from the target particles, a laser to generate an extraction beam to remove target particles from the plurality of channels, and a scanner optically coupled to the extraction beam to scan the extraction beam to the plurality of channels.

In certain embodiments, the objective lens defines a first optical path on a first side of the lens toward the surface or the plurality of channels and a second optical path on a second side of the objective lens away from the surface or the plurality of channels and wherein the extraction beam, the excitation beam, and the two dimensional array detector are optically coupled to the objective lens along at least a portion of the second optical path. In certain embodiments, the apparatus further comprising a first beam splitter to couple the extraction beam to the objective lens and a second beam splitter to couple the excitation beam to the objective lens and the two dimensional array detector to the objective lens. In certain embodiments, the first beam splitter comprises a dichroic coating to reflect the extraction beam toward the objective lens, the dichroic coating located on a surface of the first beam splitter oriented toward the objective lens and wherein the second beam splitter comprises a dichroic beam splitter configured to reflect the excitation beam toward the objective lens and transmit the fluorescence from the target particles passing through the objective lens to the two dimensional array detector.

In certain embodiments, the apparatus further comprising an F-theta relay lens to couple the extraction beam from the scanner to the objective lens. In certain embodiments, the apparatus further comprising an F-theta relay lens pair to couple the extraction beam from the scanner to the objective lens.

In certain embodiments, the apparatus further comprises a wavelength selector coupled to the excitation beam to filter the excitation beam between a beam splitter and the excitation light source and optionally wherein the wavelength selector is selected from the group consisting of filter wheel comprising a plurality of filters, a prism and a grating.

In some aspects, the disclosure provides a method of detecting and sorting target particles, the method comprising providing a substrate with a plurality of microchannels, wherein the microchannels comprise a sample material mixture comprising a plurality of target particles, scanning the contents of the microchannels with an excitation beam, detecting a fluorescence signal emitted from the microchannels wherein the fluorescence signal indicates the presence of the target particle in a microchannel, and extracting the target particles from microchannels with an extraction beam, wherein said length of time elapsing between said detecting fluorescence and extracting said target particles from a single microchannel is from about 10 ns to about 100 µs.

In some aspects, the disclosure provides a method of detecting and sorting target particles, the method comprising providing a substrate with a plurality of microchannels, wherein the microchannels comprise a sample material mixture comprising a plurality of target particles, scanning the contents of the microchannels with an excitation beam, detecting a fluorescence signal emitted from the microchannels wherein the fluorescence signal indicates the presence of the target particle in a microchannel, and extracting the target particles from microchannels with an extraction beam, wherein scanning said microchannels with an excitation beam occurs at a rate greater than 1,000,000 microchannels per second, greater than 2,000,000 microchannels per second, or greater than 3,000,000 microchannels per second.

In some aspects, the disclosure provides a method of detecting and sorting target particles, the method comprising providing a substrate with a plurality of microchannels, wherein the microchannels comprise a sample material mixture comprising a plurality of target particles, scanning the contents of the microchannels with an excitation beam, detecting a fluorescence signal emitted from the microchannels wherein the fluorescence signal indicates the presence of the target particle in a microchannel, and extracting the target particles from microchannels with an extraction beam, wherein extracting the target particles from said microchannels with an extraction beam occurs at a rate greater than 500,000 microchannels per second, 600,000 microchannels per second, 700,000 microchannels per second, 800,000 microchannels per second, 900,000 microchannels per second, or 1,000,000 microchannels per second.

In some aspects, the disclosure provides a method of detecting and sorting target particles, the method comprising providing a substrate with a plurality of microchannels, wherein the microchannels comprise a sample material mixture comprising a plurality of target particles, scanning the contents of the microchannels with an excitation beam, detecting a fluorescence signal emitted from the microchannels wherein the fluorescence signal indicates the presence of the target particle in a microchannel, and extracting the target particles from microchannels with an extraction beam, wherein extracting the target particles from said microchannels results in a collection of particles with a purity greater than 90%, greater than 95%, or greater than 99%.

In some aspects, the disclosure provides a fluorescence microscope comprising: a fluorescence excitation light source configured to direct fluorescence excitation light to a sample and to induce the emission of emitted fluorescence light from the sample; an objective lens configured to receive emitted fluorescence light from the sample; and a light detector configured to detect emitted fluorescence light received by the objective lens. The fluorescence excitation light source may be configured to direct the fluorescence excitation light to the sample such that the fluorescence excitation light does not pass through the objective lens. Directing the fluorescence excitation light to the sample such that the fluorescence excitation light does not pass through the objective lens may reduce background fluorescence detected by the light detector. Directing the fluorescence excitation light to the sample such that the fluorescence excitation light does not pass through the objective lens may reduce speckle noise detected by the light detector.

The disclosure provides a method of sorting cells, comprising screening cellular material to identify cells with a desired phenotype, wherein the cellular material is screened at a rate of 100,000 cells per second or greater. In certain embodiments, the cellular material is screened at a rate 500,000 cells per second or greater, such as at a rate of 1,000,000 cells per second or greater. In certain embodiments, the method further comprises extracting said cells of a desired phenotype from said cellular material at a rate of 100,000 cells per second or greater, such as at a rate of 300,000 cells per second or greater. Said cellular material may be screened in an array with through-holes and said cells of a desired phenotype may be extracted from said array. In certain embodiments, the extracting comprises releasing said cells of a desired phenotype using electromagnetic radiation. In certain embodiments, each through-hole of said array comprises from 0 to about 5 cells and at least 30% of the through-holes of the array comprise at least one cell.

In certain embodiments, the cellular material of said method is obtained from a human subject and/or comprises less than 5% of HSCs and HSPCs. In certain embodiments, greater than 95% of the extracted cells are HSCs and/or HSPCs. In certain embodiments, greater that 95% of the extracted cells are cells of said desired phenotype. In certain embodiments, greater than 95% of the extracted cells are viable as determined by evaluating the cells within 5 hours from said extracting. In certain embodiments, the extracted cells are suitable for therapeutic use without the need for additional sterilization steps. The extracted cells may be essentially free of pathogens. The extracted cells may comprise less than 0.1% of pathogens. In certain embodiments, the disclosure provides extracted cells obtained by any of the methods herein and pharmaceutical composition thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
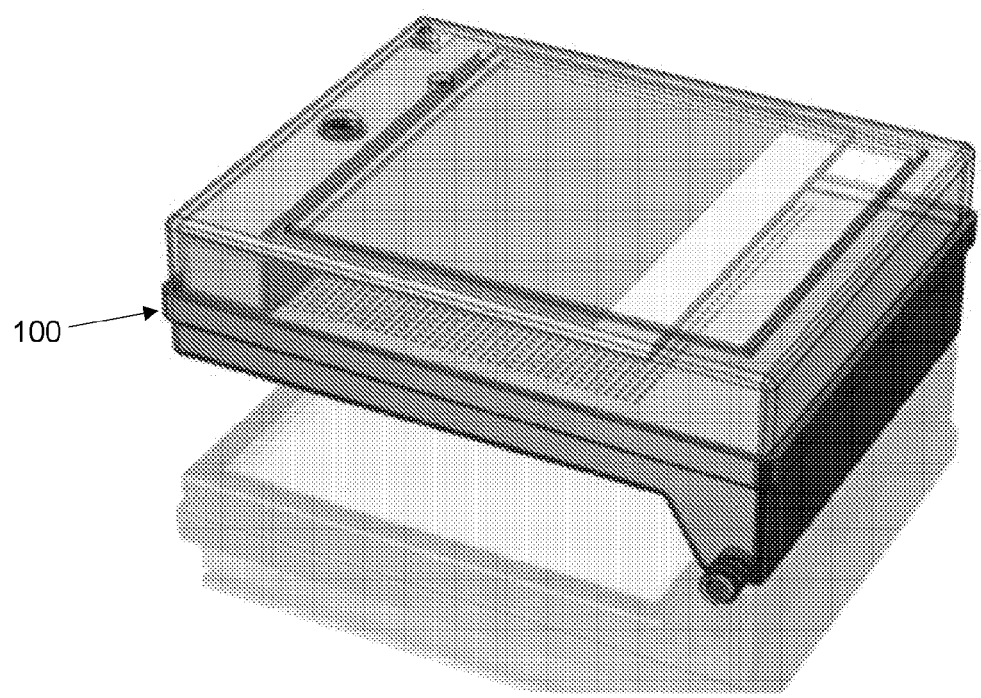
FIG. 1 is a cassette for sorting target particles according to an illustrative embodiment of the invention.

In a brief overview, the embodiments of the present disclosure provide methods and apparatuses for sorting target particles. In various embodiments, the present disclosure provides methods and apparatuses that screen, extract, and sort target particles in a simple, rapid, efficient and cost-effective manner. Additionally, in various embodiments, the present disclosure provides methods and apparatuses that screen, extract, and sort target particles under sterile conditions. In an exemplary embodiment, the present disclosure provides methods and apparatuses for sorting viable cellular material.

The present disclosure envisions target particles to include a wide range of particles, such organic and inorganic particles, natural and synthetic particles, and combinations thereof. The target particles presented herein are exemplary embodiments of target particles and are not limited to the particles described herein. In various embodiments, target particles may include any particle that weighs about 20 daltons to about 200 kilodaltons. In some embodiments, target particles may be identifiable through fluorescence. In some embodiments, target particles may include inorganic particles, such as metal beads and silica beads. For instance, metal beads may include beads containing alumina (e.g., gamma alumina). In some embodiments, target particles may include silica beads. Target particles may include polymers, such as polystyrene, polyethylene, poly(vinylpyrrolidone), acrylamidopropyl-PEG and derivatives thereof. In certain embodiments, the target particles comprise a Merrifield resin, hydroxymethyl resin, Wang resin, aminomethyl resin, SASRIN resin, TentaGel S AC resin, TentaGel PHB resin, TentaGel S $NH_2$ resin or combinations thereof. Target particles may also comprise carbon nanotubes and fullerenes. In certain embodiments, target particles comprise particles that are used in split-pool synthesis. In some embodiments, target particles comprise cellular material, such as whole cells, lysed cells, cellular components, extracellular matrix, biological tissue, and portions thereof. In some embodiments, target particles comprise biomolecules such as proteins, peptides, antibodies, carbohydrates, lipids, nucleic acids, nucleotides, primary metabolites, secondary metabolites, and natural products. Target particles may also include small molecules, both synthetic and natural small molecules, for example, molecules which weigh less than 1000 daltons. In some embodiments, target particles may include viruses.

In certain embodiments, the target particles comprise cellular material, such as whole cells or lysed cells. Cells may be any cell derived from an organism, which include human, animal, fungal, microbial, insect, and modified cells thereof. In certain embodiments, the target particles are identified in a cellular material mixture. In certain embodiments, a cellular material mixture comprises cellular material, an aqueous solution and optionally opaque particles. Examples of an aqueous solution include media, buffer, and water. In certain embodiments, the disclosure provides systems and methods to isolate target cells from a cellular material mixture, wherein said target cells express or produce particular proteins, carbohydrates, enzymes, peptides, hormones, receptors, or combinations thereof. In certain embodiments, the disclosure provides systems and methods to isolate target cells from a cellular material mixture that that produce particular antibodies. In certain embodiments, the disclosure provides systems and methods to isolate target cells from a cellular mixture that are particular genetically engineered cells or activated cells.

The term "opaque," as described herein, refers to a material that absorbs at least a portion of the electromagnetic spectrum. An opaque material may not permit, at least partially, the passage of visible light through the material. An opaque material may not permit the passage of one or more wavelengths ranging from about 390 nm to about 700 nm. For example, such materials will not permit the passage of one or more wavelengths ranging from about 450 nm to about 495 nm.

In one aspect, the present disclosure is directed to a cassette for sorting target particles. In some embodiments, the cassette is an enclosed system that permits the sorting of target particles under sterilized conditions. The cassette may be sterilized prior to use. The cassette may contain one or more fill ports that allow the user to introduce a sample material mixture and optionally other solutions into the cassette without compromising sample integrity, e.g., exposing the sample to pyrogens or other contaminants. In some embodiments, the cassette may be intended for only a single use, e.g., disposable after use. For example, the cassette may be used for sorting cellular material from a single patient sample, and disposed of after use. Additionally, the cassette may be configured to be received by various apparatuses and machines to facilitate sorting of target particles. In another embodiment, the cassette may be available with instructional information on how to use the cassette.

In another aspect, the disclosure provides a method for sorting target particles using the cassette of the disclosure. In various embodiments, a sample material mixture may be loaded into the microchannels of a substrate of a cassette for scanning and extraction of target particles. In an exemplary embodiment, a cellular material mixture may be loaded into the microchannels of a substrate of a cassette for scanning and extraction of cellular material. In certain embodiments, the sample material mixture may be loaded onto the first surface of the substrate for scanning and extraction. In certain embodiments, one or more types of cells, e.g., cells with certain cell surface markers, may be extracted from a cellular material mixture. In certain embodiments, one or more types of cells that are secreting certain proteins or other biomolecules of interest may be extracted from a cellular material mixture. In certain embodiments, one or more types of cells that are expressing certain intracellular proteins or other biomolecules of interest may be extracted from a cellular material mixture. In certain embodiments, one or more types of cells that are expressing certain proteins or other biomolecules of interest targeted to a specific organelle or other subcellular localization may be extracted from a cellular material mixture. In certain embodiments, one or more types of cells that are expressing a combination of the aforementioned attributes may be extracted from a cellular material mixture. In certain embodiments, the extraction of one or more types of cells may be performed under sterile conditions.

In certain embodiments, the microchannels of the substrate may comprise opaque particles. The opaque particles may be involved in a process in which the opaque particles absorb electromagnetic radiation and, vaporize a portion of the aqueous media, which thereby causes the cellular material in the microchannel to be released from the microchannel. In certain embodiments, the energy released from said process may damage the cellular viability of the cellular material. To protect the viability of the cellular material, the opaque particles may be added to the microchannels in a manner that protects and preserves cellular viability of the cellular material from said process. In certain embodiments, the viability of the cellular material is maintained by spacing the opaque particles a distance away from cells in the microchannels. In one embodiment, the method involves the addition of two mixture layers to the microchannel of substrate, wherein the first mixture layer contains opaque particles in a transparent solution, e.g., suspended in a gel, and the second mixture layer contains cellular material in an aqueous solution. In certain embodiments, the method of loading microchannels of a substrate involves the addition of particles comprising an opaque core and an insulating outer shell of a transparent material, which prevents contact or close approach of a cell with the opaque core. In certain embodiments, the method of loading microchannels of a substrate involves the addition of opaque microparticles and transparent microparticles, in which the transparent microparticles prevent contact or close approach of the cell with the opaque microparticles.

Additionally, the disclosure provides a method to position cells closer to the opening of the microchannel than the opaque particles. In some embodiments, cells are observed through one opening of the microchannel, and it is advantageous over existing methods to position the opaque particles distal to the cell from the plane of observation. Such positioning of the opaque particles may permit the observation of a greater number of cells relative to the number of cells loaded onto the microchannel. In certain embodiments, the method of loading microchannels of a substrate involves the addition of a cellular material mixture and opaque particles in a sequential manner.

Additionally, the disclosure provides a method to control the position the cells and opaque material within the microchannel. In some embodiments, cells are assisted towards one end of the microchannel using sonication or ultra-sonication. In some embodiments the opaque material is assisted towards one end of the microchannel using sonication or ultra-sonication. In some embodiments, these processes are performed sequentially. In certain embodiments, a cassette of the disclosure further comprises a contact transducer or similar device, wherein the contact transducer may be located at any functional position on the cassette, e.g., in contact with the substrate within the housing or on the external surface of the housing. In certain embodiments, the contact transducer may be in contact with one or more components of a cassette described herein.

Additionally, the disclosure provides a method to discriminate one cell from multiple cells deposited in microchannels of a substrate. In certain embodiments, the method involves the use of fluorescent material positioned distal to the cell or cells from the plane of observation. The fluorescent light of the fluorescent material may be subsequently measured. In certain embodiments, the method involves the distribution of fluorescent material amongst the cellular material and the displacement of fluorescent material in the presence or absence of cells is used to quantify cellular material.

Additionally, the disclosure provides optical apparatuses for laser scanning cell sorting.

In one embodiment, the disclosure provides an optical apparatus utilizing a rotating polygon mirror. In a further embodiment, said apparatus is combined with a linear stage, X-Y stage, or galvanometers.

In another embodiment, the disclosure provides an optical apparatus utilizing two rotating polygon mirrors. In a further embodiment, said apparatus is combined with one or more linear stages, X-Y stages, galvanometers, digital light processing systems, or resonant scanners.

In another embodiment, the disclosure provides an optical apparatus utilizing two rotating polygon mirrors and a confocal detection technique. In a further embodiment, said apparatus is combined with a linear stage, X-Y stage, or galvanometers.

In another embodiment, the disclosure provides an optical apparatus utilizing a galvanometer scanning mechanism. In a further embodiment, said apparatus is combined with a linear stage, X-Y stage, or galvanometers.

In some aspects, the methods of the disclosure enable the preparation of pharmaceutical compositions of hematopoietic stem cells (HSCs) and/or hematopoietic stem progenitor cells (HSPCs) with unprecedented sterility, purity, and viability. In particular, the disclosure provides methods of sorting cells, e.g., cells obtained from a subject, wherein the method comprises one or more of the following: (a) screening cellular material at a rate of 100,000 cells per second or more, such as 200,000 cells per second or more, such as 300,000 cells per second or more; (b) scanning cells wherein less than 10% of the original cellular material comprises HSCs and/or HSPCs (c) extracting cells of a desired phenotype or phenotypes at a rate of 100,000 cells per second or more, such as 200,000 cells per second or more, such as 300,000 cells per second or more; (d) extracting cells thereby producing a cell extract wherein 95% or more of said cell extract cells are HSCs and/or HSPCs; (e) extracting cells thereby producing a cell extract wherein 95% or more, such as 95% or more or even 98% or more of the extracted HSCs and/or HSPCs have the desired phenotype or phenotypes; (f) extracting cells thereby producing a cell extract wherein the cell extract has a viability of greater than 95%; and (g) extracting cells thereby producing a cell extract wherein HSCs and/or HSPCs of the cell extract are suitable for clinical use without the need for further purification or sterilization.

In some aspects, the disclosure provides pharmaceutical compositions of HSCs and/or HSPCs with one or more of the following characteristics: (a) the composition comprises less than approximately 1% of pathogens and other contaminants, such as a negligible amount of pathogens and other contaminants; (b) 95% or more, such as 95% or more or even 98% or more of the HSCs and/or HSPCs of the composition have a desired phenotype or phenotypes; (c) 95% or more of the cells of the composition are viable; (d) the composition comprises less than 0.01% of naïve T cells; and (e) the composition is suitable for therapeutic use.

Definitions

It is to be understood that the terminology used herein is for the purpose of describing particular embodiments only and is not intended to be limiting.

Unless otherwise defined, the technical and scientific terms used herein have the same meaning as commonly understood by one of ordinary skill in the art. Expansion and clarification of some terms are provided herein. All publications, patent applications, patents and other references mentioned herein, if not otherwise indicated, are explicitly incorporated by reference.

As used herein, the singular forms "a," "an," and "the" include plural referents unless the context clearly dictates otherwise.

The term "hydration" and "hydrate" as used herein refers to restoring or maintaining fluid balance.

The term "sterile" and "sterilized" as used herein refers to reduce the presence of contaminants, bacteria, pathogens or other unwanted living organisms.

In the figures presented herein, like numbered elements refer to like components.

Cassette

Figure 2:
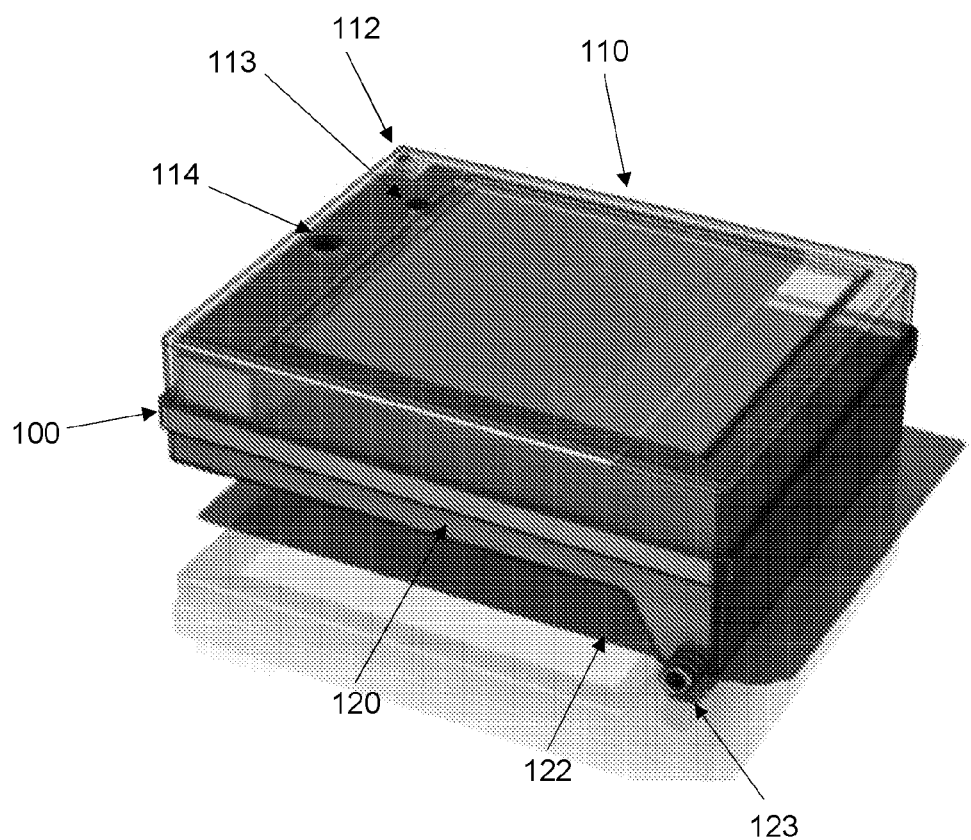
FIG. 2 represents an external view of a cassette for sorting target particles.

In an exemplary embodiment, FIG. 1 illustrates a cassette for sorting target particles. The present disclosure envisions target particles to include a wide range of particles, such organic and inorganic particles, natural and synthetic particles, and combinations thereof. The target particles presented herein are exemplary embodiments of target particles and are not limited by the exemplary embodiments. In various embodiments, target particles may include any particle that weighs about 20 daltons to about 200 kilodaltons. In some embodiments, target particles may be identifiable through fluorescence. In some embodiments, target particles may include inorganic particles, such as metal beads and silica beads. For instance, metal beads may include beads containing alumina (e.g., gamma alumina). In some embodiments, target particles may include silica beads. Target particles may include polymers, such as polystyrene, polyethylene, poly(vinylpyrrolidone), acrylamidopropyl-PEG and derivatives thereof. For example, the polymers may be a Merrifield resin, hydroxymethyl resin, Wang resin, aminomethyl resin, SASRIN resin, TentaGel S AC resin, TentaGel PHB resin or TentaGel S $NH_2$ resin. Target particles may also include carbon nanotubes and fullerenes. Such target particles may include particles that are used in split-pool synthesis. Additionally, in some embodiments, target particles may include cellular material. Cellular material may include whole cells, lysed cells, cellular components, extracellular matrix, biological tissue, and portions thereof. In some embodiments, target particles may also include biomolecules, which include proteins, peptides, antibodies, carbohydrates, lipids, nucleic acids, nucleotides, primary metabolites, secondary metabolites, and natural products. Target particles may also include small molecules, both synthetic and natural small molecules, which weigh less than 1000 daltons. In some embodiments, target particles may include viruses. Cellular material may comprise a cell suspension. Cells may be any cell derived from an organism, which include human, animal, fungal, microbial, insect, and modified cells thereof. A cellular material mixture comprises cellular material, opaque particles, and an aqueous solution. Examples of an aqueous solution include media, buffer, and water. The device of the present disclosure may be used to isolate cells that differentially express or produce proteins, carbohydrates, enzymes, peptides, hormones, receptors, and additionally cells that produce antibodies, genetically engineered cells, and activated cells. In an exemplary embodiment, according to FIGS. 2 and 3, the cassette 100 comprises a top cover 110, a bottom cover 120, a substrate 130, a sample well 140, and a frame 150. As depicted in FIG. 2, the top cover 110 is positioned above the bottom cover 120 and is positioned in a substantially parallel plane with the bottom cover 120. The cassette 100 may be an enclosed system.

In one embodiment of a cassette for sorting target particles, as depicted in FIG. 2, the top cover 110 may comprise one or more fill ports for receiving solutions into the cassette 100. In some embodiments, the top cover may comprise one or more outlet ports for draining solutions from the cassette. The one or more fill ports may be configured to introduce solutions into the cassette 100. Such solutions may be introduced in order to hydrate the membrane, receive a sample material mixture for loading a sample material mixture onto the substrate, receive a sample material mixture into the sample well, and/or receive buffer solution to drain target particles, such as cellular material, out of the cassette.

In certain embodiments, the top cover comprises one fill port configured to receive solutions into the cassette. In an exemplary embodiment, as depicted in FIG. 2, the fill ports of the top cover 110 comprise an accessory material port 112, a hydrate port 113, and a sample port 114. The accessory material port 112, the hydrate port 113, and the sample port 114 may be configured to receive solutions. The sample port 114 may be configured to receive a sample material mixture for loading into a sample well 140. The sample port 114 may be in fluid communication with the sample well 140. In another embodiment, the sample port may be configured to receive sample material mixture for direct loading onto the substrate and into the microchannels of the substrate. In some embodiments, about $1 \times 10^6$ to $100 \times 10^9$ cells are loaded into the cassette 100. The hydrate port 113 may be configured to receive solutions for hydrating the hydration membrane 151. The hydrate port 113 may be in fluid communication with the hydration membrane 151. The accessory material port 112 may be configured to receive an aqueous solution for collecting target particles from the cassette 100. In some embodiments, the aqueous solution is a buffer. The accessory material port 112 may be in fluid communication with the internal surface of the bottom cover 120, the collection well 122, and/or the receiving port 123. Additionally, the collection well 122 may be in fluid communication with the receiving port 123. In certain embodiments, the method of loading microchannels of any substrate described herein, may be accompanied by a sonication step. The sonication step may allow the target particles, opaque particles or other components of the sample material mixture to settle into the microchannels. In certain embodiments, the sonication step may occur prior to the scanning of the microchannels. For example, the sonication step may occur prior to, concurrent with, or subsequent to said loading step or a combination thereof. In certain embodiments, the sonication step occurs prior to and concurrent with the loading of the microchannels. In certain embodiments, the sonication step occurs concurrent with and subsequent to the loading of the microchannels.

In certain embodiments, the bottom cover may comprise one or more fill ports for receiving solutions into the cassette. In some embodiments, the bottom cover may comprise one or more outlet ports for draining solutions from the cassette. The one or more fill ports may be configured to introduce solutions into the cassette. Such solutions may be introduced in order to hydrate the membrane, receive a sample material mixture for loading a sample material mixture onto the substrate, receive a sample material mixture for loading a sample material mixture into the sample well, and/or receive buffer solution to drain target particles, such as cellular material, out of the cassette. In certain embodiments, the bottom cover comprises one fill port configured to receive solutions into the cassette. In another embodiment, the fill ports of the bottom cover comprise an accessory material port, a hydrate port, and a sample port. The sample port may be configured to receive a sample material mixture for loading into a sample well. The sample port may be in fluid communication with the sample well. In another embodiment, the sample port may be configured to receive a sample material mixture for direct loading onto the substrate and into the microchannels of the substrate. In some embodiments, about $1 \times 10^6$ to $100 \times 10^9$ cells are loaded into the cassette. The hydrate port may be configured to receive solutions for hydrating the hydration membrane. The hydrate port may be in fluid communication with the hydration membrane. The accessory material port may be configured to receive an aqueous solution for collecting target particles from the cassette. In some embodiments, the aqueous solution is a buffer. The accessory material port may be in fluid communication with the internal surface of the bottom cover, the collection well, and/or the receiving port. Additionally, the collection well may be in fluid communication with the receiving port.

Figure 3:
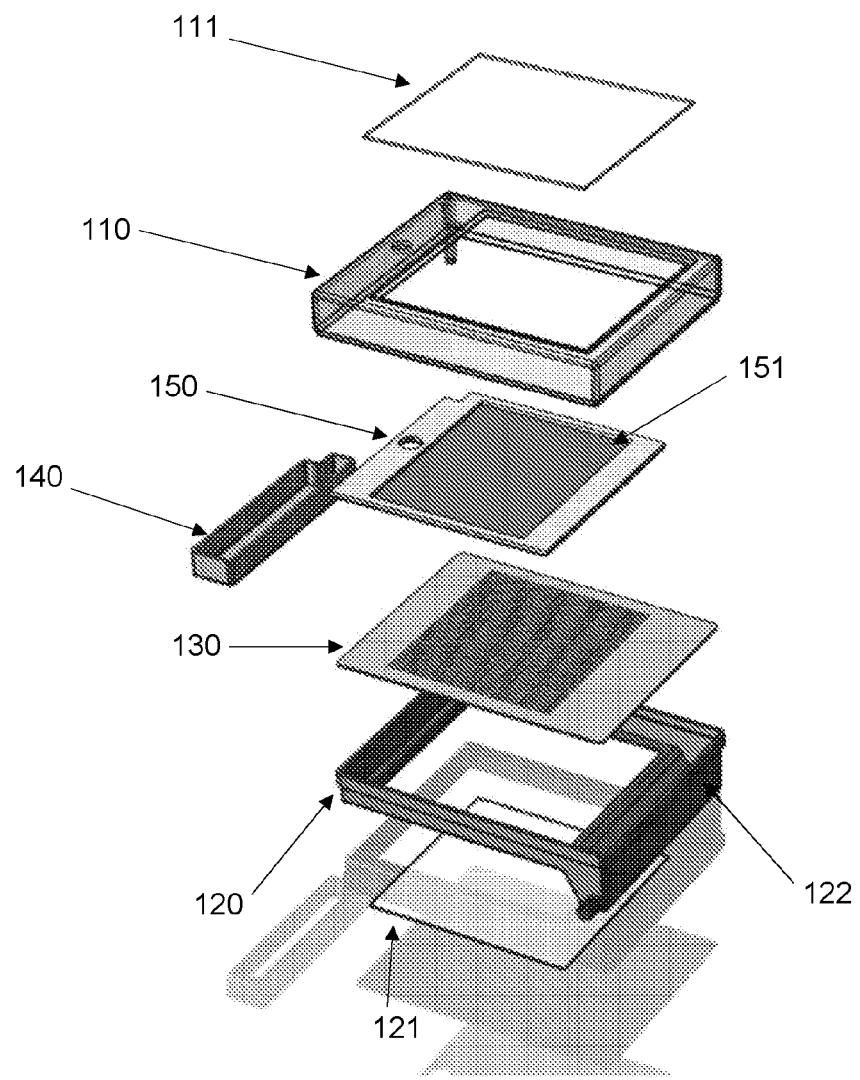
FIG. 3 represents several external and internal components of a cassette for sorting target particles.

In various embodiments, the cassette may contain a transmissive portion that is at least partially transparent to certain wavelengths of electromagnetic radiation. In an embodiment, the transmissive portion is at least partially transparent to wavelengths in the range of 250 nm to 1600 nm. A transmissive portion contains a material that at least partially permits the transfer of one or more electromagnetic waves from one location to another. For example, a transmissive portion may include, but is not limited to, glass, quartz, plastics, or combinations thereof. In various embodiments, the transmissive portion is a transmissive window. In some embodiments, as depicted in FIG. 3, the top cover may comprise a top window 111. The top window 111 may be a transmissive window. In another embodiment, the top window 111 may be a non-transmissive window. A non-transmissive window contains a material that does not permit the transfer of electromagnetic radiation from one location to another. In an exemplary embodiment of a cassette for sorting target particles, as depicted in FIG. 3, the bottom cover 120 may comprise a bottom window 121. In another embodiment, the bottom window 121 may be a transmissive window. The bottom window 121 may be a non-transmissive window. In certain embodiments, the top window 111 can be a non-transmissive window and the bottom window can be a transmissive window.

In an embodiment of a cassette for sorting target particles, as represented by FIG. 3, the cassette 100 is configured to receive a substrate 130 within the cassette 100. The substrate is located between the top cover 110 and the bottom cover 120. As shown in FIG. 1, the substrate is encapsulated by the housing units of the cassette 100. The substrate is protected from contamination during the sorting of the target particles.

In certain embodiments, the cassette comprises a first housing and a second housing that are coupled to each other in any manner known in the art. For example, the first housing and second housing may be two separate components that are coupled to each other through a hinge that permits opening of the housing to expose the inside of the cassette. In certain embodiments, the first and second housing are two separate components that are coupled to one another in a reversible manner such as interlocked together with complementary adjoining elements, e.g., the interface of the first housing comprises a receiving element, such as a concave portion, and the interface of the second housing comprises a donating element, such as a convex portion, wherein the concave and convex elements reversibly interlock with one another. In certain embodiments, the first housing and second housing are attached to one another in a permanent manner such as with an adhesive or melded together. In certain embodiments, the first housing and second housing are coupled in a manner that they a single housing, such as where the first housing and second housing are not formed from the attachment of multiple components or are molded or formed by the stacking of layers, e.g., 3D printing, and are irreversibly coupled, e.g., do not comprise seems or hinges to separate the first housing from the second housing.

Encapsulate or encapsulation of the substrate as described herein, refers to the positioning of the entirety of the substrate within the housing of the cassette.

In certain embodiments, the substrate contains a first surface and a second surface. The substrate may have dimensions of about 3 mm×3 mm×0.3 mm to about 5000 mm×15000 mm×1000 mm. The distance from the first surface to the second surface of the substrate is from about 10 µm to about 1000 mm. In some embodiments, the substrate may be rectangular, octagonal, or circular in shape. In some embodiments, the substrate may be a glass plate.

In certain embodiments, the first surface of the substrate is coupled to the first surface of an absorbent material. The first surface of the substrate may be modified to enhance the adhesive properties of the substrate. For example, the first surface of the substrate may be coated with one or more diaminopropyl silane groups. The absorbent material may comprise opaque particles. The absorbent material may comprise a metal. In some embodiments, the second surface of the absorbent material may be coupled to the first surface of a transparent layer. The transparent layer may comprise agarose, collagen, matrigel, alginate and combinations thereof. In some embodiments, a sample material mixture may be coupled to the second surface of the transparent layer. In some embodiments, the substrate may be coupled to a channel that is configured to receive extracted target particles. For example, the channel may be a flow cell tube.

In certain embodiments, the disclosure provides a substrate such as those previously described herein with a plurality of microchannels, wherein microchannels of the substrate comprise target particles and opaque material wherein said target particles and opaque material are separated with a spacer comprising a transparent gel or transparent solid. In certain embodiments, the opaque material comprises a particle or a coating. In certain embodiments, the opaque material is separated from the target particles by at least about 1 µm or more.

In various embodiments, the substrate may be a glass micropore array. In certain embodiments, the substrate further comprises a plurality of microchannels that extend from the first surface and second surface. The microchannels of the substrates described herein may be positioned substantially in parallel to each other. The substrate may contain about 1 million to about 300 billion microchannels. In certain embodiments, microchannels of a substrate described herein have an average internal diameter of about 50 nm to about 500 µm. In certain embodiments, microchannels of a substrate described herein have an average internal diameter of about 50 nm to about 10 microns. In certain embodiments, microchannels of a substrate herein have an average internal diameter of about 50 microns to about 500 microns.

In certain embodiments, a microchannel of the substrate described herein is capped or covered at one of the openings. In certain embodiments, microchannels of the substrate do not have an opening on one of the surfaces of the substrate such as on the first surface or second surface of the substrate. A microchannel of the substrate may be capped or covered with a material. For example, such material may be agarose-based, glass-based, metal-based, gelatin-based, and/or plastic-based.

In certain embodiments, the microchannels of the substrate are configured to receive a sample material mixture from the sample port. In another embodiment, the microchannels of the substrate 130 are configured to receive a sample material mixture from the sample well. The contents in the microchannels may be held in place by hydrostatic forces.

In an embodiment of a cassette for sorting target particles, as depicted in FIG. 2, the cassette 100 is configured to receive a frame 150 within the cassette 100. In certain embodiments, the frame 150 may further include a hydration membrane 151 within the frame 150. The frame 150 containing the hydration membrane 151 may be placed on top of the substrate 130 following the adding or loading of a cellular material mixture to the substrate 130. The hydration membrane 151 may seal the top surface of the substrate 130 in order to maintain the water content or certain concentrations of dissolved solids in the microchannel. One or more substantially gas permeable and/or impermeable hydration membranes may be used to seal the surfaces of the substrate 130 following the addition of cellular material to the substrate 130. The hydration membrane 151 can be a solid capable of retaining moisture. For example, the hydration membrane 151 may be a paper towel, Kimwipes®, agarose, nitrocellulose or plastics, such as polyvinylidene fluoride (PVDF). In some embodiments, a hydration layer made out of an aqueous solution may be used instead of or in conjunction with a hydration membrane. In an embodiment, the hydration membrane allows water from a reservoir to equilibrate with the top liquid layer of the liquid in the microchannel, which can help mitigate the water lost from evaporation. For example, a hydration membrane 151 placed in contact with the top surface of the substrate 130, with water placed on top of the film, would trap the contents of the microchannel within each individual microchannel, but would allow water or media to flow into the microchannel. The hydration membrane may be nitrocellulose and NAFION® membranes. A similar arrangement could be obtained with a porous form of a polytetrafluoroethylene membrane (e.g., GORE-TEX® fabrics) having very small holes (e.g., 10-100 nm) that would trap any cells in the microchannel but allow water, media and other reagents to pass into the microchannels.

Figure 4A:
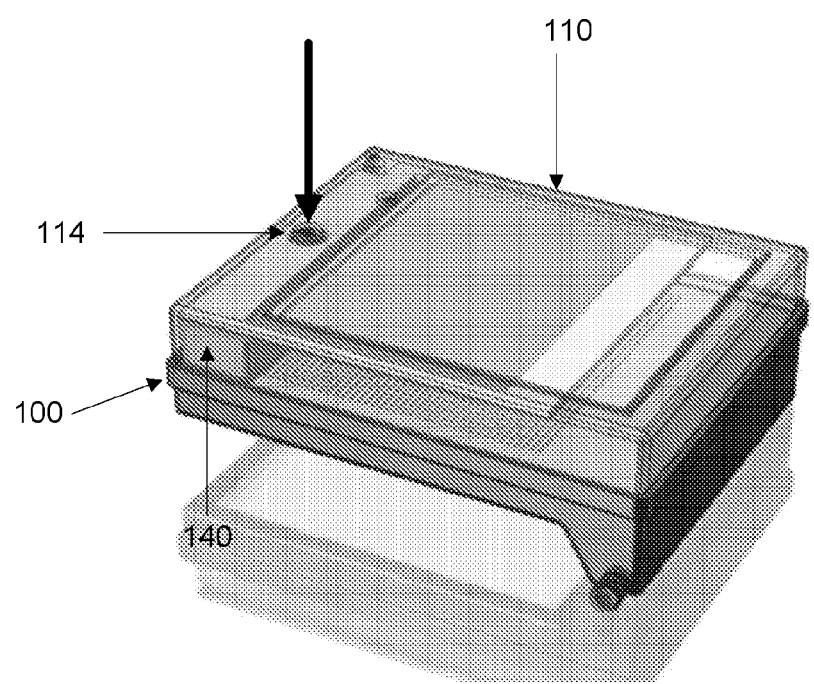
FIG. 4A illustrates one embodiment of adding or loading a sample material mixture to a sample well.
Figure 4B:
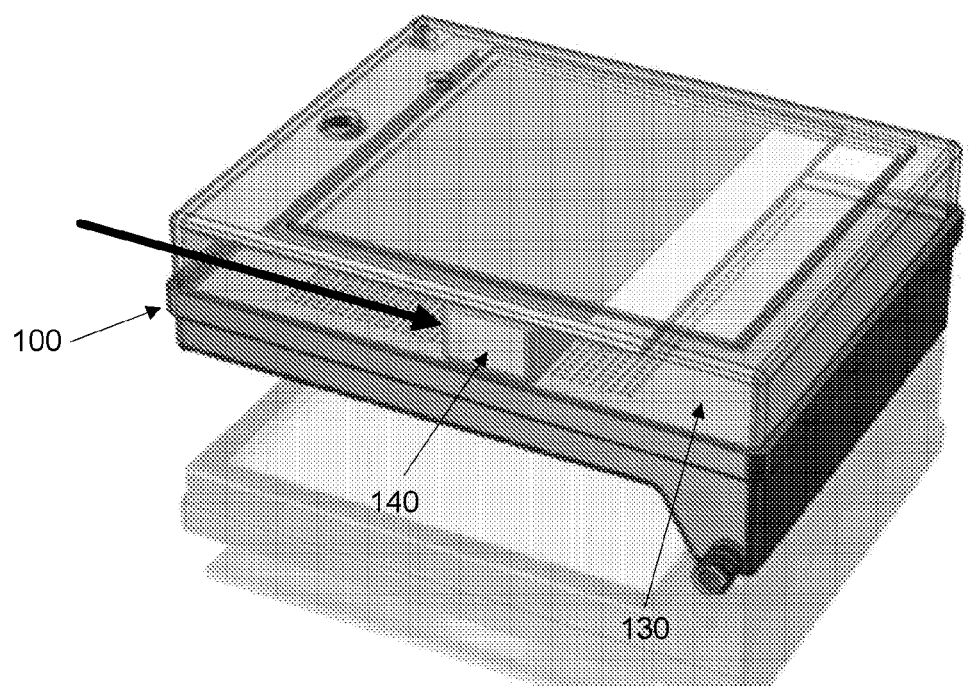
FIG. 4B illustrates one embodiment of adding or loading a sample material mixture from a sample well to a substrate comprising a plurality of microchannels. The sample well moves parallel to the substrate to add or load sample material mixture to the substrate. The sample well may move from the first end of the substrate the second end of the substrate to add or load sample material mixture to the substrate.
Figure 4C:
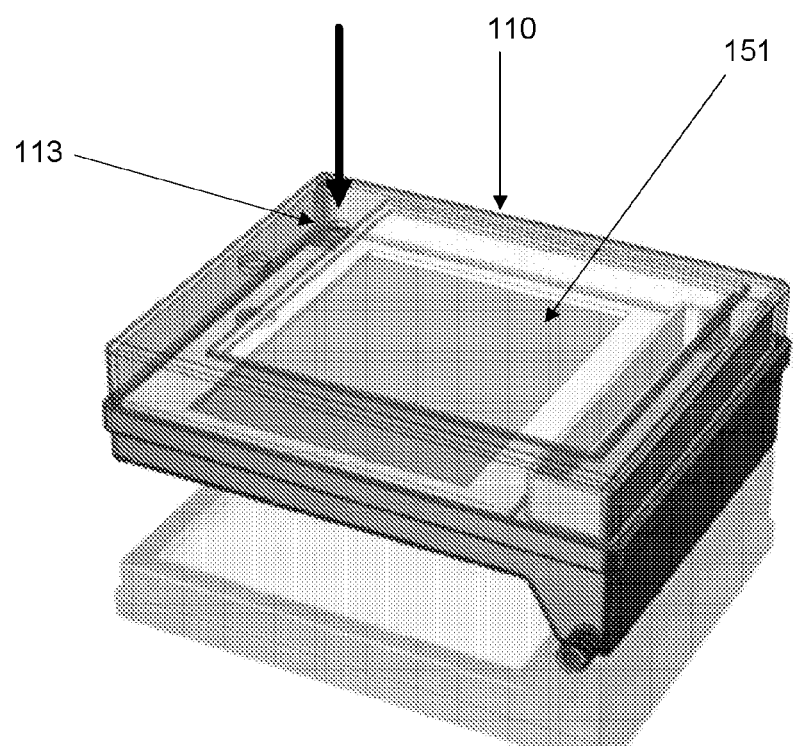
FIG. 4C illustrates one embodiment of adding or loading a solution to the hydration membrane of the cassette through the hydrate port on the top cover of the cassette.
Figure 4D:
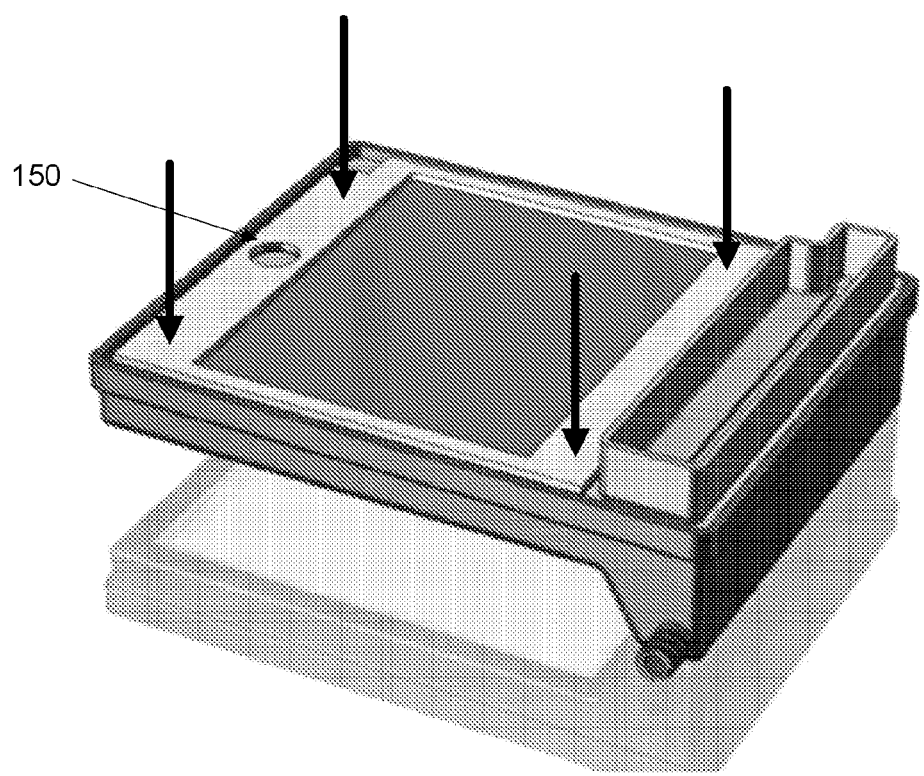
FIG. 4D illustrates one embodiment of placing a frame containing a hydration membrane on the surface of a substrate through an external magnetic force.

In an embodiment of a cassette for sorting target particles, depicted in FIG. 2, the cassette contains a sample well 140. The sample well 140 is configured to receive solutions from one or more fill ports. As depicted in FIG. 4A, in one embodiment, the sample well 140 is configured to receive a sample material mixture from the sample port 114. The sample well may comprise, contain, or be connected to materials that may be magnetized. Such materials include iron, nickel, cobalt, some alloys of rare metals, some naturally occurring minerals, and compositions thereof. In one embodiment, as depicted in FIG. 4B, the sample well 140 may be configured to be in contact with a surface of the substrate 130. In certain embodiments, the sample well 140 may be configured to move across a surface of a substrate 130. The sample well 140 may be configured to move manually, mechanically, or electronically. In some embodiments, the sample well may be connected to wheels or other ball bearing which are, in turn, in contact with a smooth track attached to the top cover. In various embodiments, the sample well may be connected to gears, which are in turn connected to groves that are connected to the top cover. When force is applied in parallel to the track, the sample well is guided in the direction of the tracks. Force may be applied by a tensile force of attached cables which are connected to a motor. The motor may be internal or external to the cassette and powered manually with a crank or electronically with a battery or other voltage source. In certain embodiments, the movement of the sample well may be controlled magnetically. The sample well may be externally controlled by magnetic forces located outside of the cassette, e.g., within the particle sorting apparatus of the disclosure. In certain embodiments, magnets are attached to the sample well in proximity to the inner wall of the top cover. Magnetic fields external to the cassette are then manipulated into close contact with the internal magnets on the sample well. Movement of the external magnetic field generates a force on the magnets on the interior of the cassette and moves the sample well along a track on the interior of the top cover. Magnets may be rare earth magnets like neodymium or electromagnets. In certain embodiments, as depicted in FIG. 4B, the sample well 140 may be moved while the top cover 110 remains attached to the bottom cover 120. In one embodiment, the sample well may be configured to add or load cellular material into the microchannels of a substrate. In one embodiment, the sample well further includes a spreading implement located at the bottom surface of the sample well. The spreading implement may be in contact with the substrate to distribute cellular material into the microchannels. The spreading instrument may resemble a squeegee, foil, or policeman. The spreading instrument may be made out of rubber, plastic, metal or other liquid impermeable, bio-compatible material.

Figure 5A:
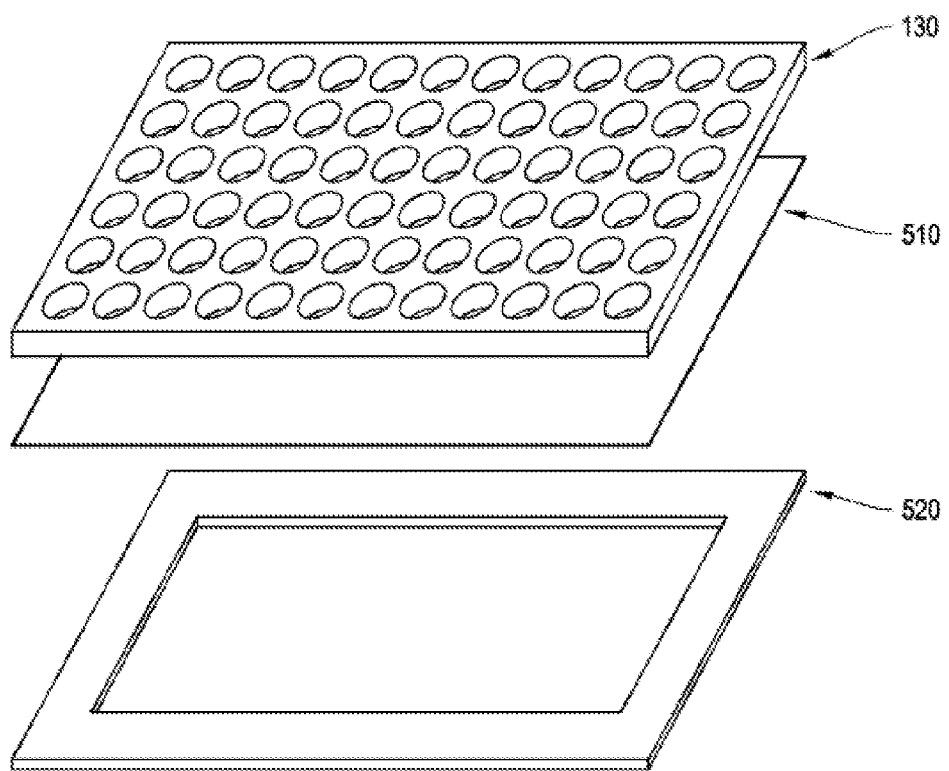
FIG. 5A represents several internal components of a cassette that include a substrate, a seal, and a metal frame.
Figure 5B:
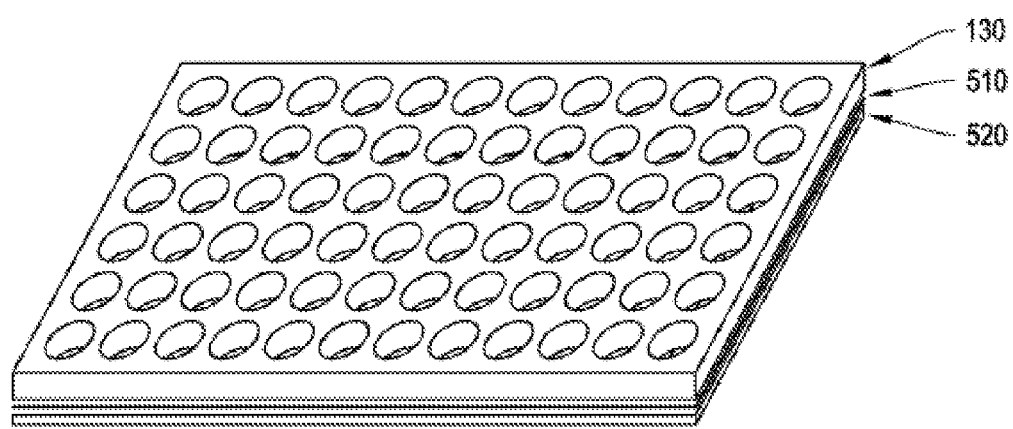
FIG. 5B represents the substrate affixed to the metal frame through a seal, which reduces sagging of the substrate under heated conditions.

The embodiment of FIG. 1 further includes a seal 510 and a metal frame 520, as depicted in FIG. 5A and FIG. 5B. As depicted in FIG. 5A and FIG. 5B, in one embodiment, the seal 510 is placed between the substrate 130 and the metal frame 520. The seal 510 may be an adhesive material. For example, the seal 510 may be an epoxy adhesive, including polyurethane, acrylic, and cyanoacrylate, which can be used as an adhesive for wood, metal, glass, stone, and plastics. The epoxy adhesive can be made flexible or rigid, transparent or opaque, fast-setting or slow setting. As depicted in FIG. 5B, the substrate 130 and the metal frame 520 are in contact with the seal 510. In one embodiment, the substrate 130, the seal 510, and the metal frame 520 may be assembled at a temperature of 15° C. or less. For example, the substrate 130, the seal 510, and the metal frame 520 may be assembled at a temperature of 5° C. As represented in FIG. 5B, the substrate 130, the seal 510, and the metal frame 520 are assembled when in operation. The temperature of the substrate 130, the seal 510, and the metal frame 520 may be increased during the operation of the cassette 100. At increased temperatures, the substrate 130, the seal 510, and the metal frame 520 may expand. In some embodiments, at increased temperatures, the expansion of the metal frame exceeds the expansion of the substrate, thereby causing a tension to be applied across the surface of the substrate. Such tension across the surface of the substrate may reduce sagging of the substrate and thereby maintain planarity of the substrate. In some embodiments, the substrate comprises of a first end, a second end, and a middle portion, and the first end, the second end, and the middle portion are substantially on the same plane.

In an embodiment of a cassette for sorting target particles, depicted in FIG. 2, the bottom cover 120 may also comprise an internal surface for collecting target particles. In one embodiment, the internal surface may include a capture surface. The capture surface may be removable or affixed to the cassette. For example, the capture surface may be a dish, a plate, a curved surface, or a flat surface. In some embodiments, as depicted in FIG. 2, the internal surface of the bottom cover 120 may comprise a collection well 122, and a receiving port 123. The internal surface of the bottom cover 120 may be configured to receive solutions from one or more fill ports from the top cover 110. The bottom cover may comprise one or more outlet ports for draining target particles and aqueous solutions. In an embodiment of the disclosure, as depicted in FIG. 4F, the internal surface of the bottom cover 120 is configured to receive an aqueous solution from the accessory material port 112. The aqueous solution may assist in transporting target particles from the internal surface of the bottom cover 120 to the collection well 122. The aqueous solution may also assist in transporting target particles from the collection well 122 to the receiving port 123. In one embodiment, the target particles may be recovered from the receiving port 123.

In another embodiment, the internal surface of the bottom cover is configured to receive solutions from one or more fill ports from the bottom cover. The bottom cover may comprise one or more outlet ports for draining target particles and aqueous solutions. In one embodiment, the internal surface of the bottom cover is configured to receive an aqueous solution from a fill port. The aqueous solution may assist in transporting target particles from the internal surface of the bottom cover to the collection well. The aqueous solution may also assist in transporting target particles from the collection well to the receiving port. In certain embodiments, target particles may be recovered from the receiving port.

In an embodiment of a cassette for sorting target particles, depicted in FIG. 1, the top cover 110 may attach to the bottom cover 120. As discussed earlier, the cassette 100 may be an enclosed system. The enclosed system protects the cellular material from contaminants. The cassette may be sterilized prior to adding or loading of cellular material onto the substrate 130. The interior portions of the cassette 100 may be sterilized separately and the cassette 100 assembled under sterile conditions. The top cover 110 and the bottom cover 120 may prevent contaminant entry into the cassette 100. The top cover 110 and the bottom cover 120 may protect the target particles from contamination, which include bacteria, molds, yeasts, viruses, and mycoplasma. The closed nature of the cassette 100 also protects the operator from any potential pathogens in the sorting material, and protects each sample from contamination from another sample.

Method of Sorting Target Particles

In various embodiments, the present disclosure provides a method for sorting target particles. In various embodiments of a method for sorting target particles, as depicted in FIGS. 4A and 4B, a sample material mixture is added or loaded into the cassette 100 through a sample port 114 located on the top cover 110. In some embodiments, about $1 \times 10^6$ to $100 \times 10^9$ cells are loaded into the cassette 100. In various embodiments, the sample material mixture is directly added or loaded onto the substrate. In some embodiments, the substrate may be flooded with the sample material mixture. The sample material mixture may move into the microchannels of the substrate through capillary action. In some embodiments, the substrate may be flooded with the sample material mixture when the diameter of the microchannels ranges from about 10 nm to about 100 μm. In certain embodiments, any substrate described herein may further comprise border elements, wherein said border elements extend vertically from the perimeter of the top surface of the substrate and permit containment of fluid on the top surface of said substrate. In certain embodiments, wherein said substrate is flooded with a volume of sample material mixture, said border elements contain said sample material mixture and prevent said mixture from contaminating other portions of said cassette. In certain embodiments, the substrate may comprise border elements with vertical dimensions from about 10 microns to about 10 cm. In certain embodiments, the average diameter of the microchannels of the substrate are proportional to the height of the border elements, such that a substrate with microchannels of narrow average diameters, e.g., about 50 nm to about 10 microns, has border elements with vertical dimensions from about 100 microns to about 3 mm and a substrate with microchannels of wider average diameter, e.g., about 50 microns to about 500 micron, has border elements with vertical dimensions from about 1 mm to about 10 cm.

In another embodiment, the microchannels of the substrate may be filled with the sample material mixture by placing a hanging drop from the top cover to a position above the microchannel. In some embodiments, the hanging drop may be in contact with the microchannel. In some embodiments, the hanging drop may range in volume from about 10 μL to about 900 mL. The sample material mixture may move into the microchannels through capillary action. In another embodiment, the sample material mixture may be received by the sample well 140. In an exemplary embodiment, as depicted in FIG. 4B, the sample well 140 may move across the top surface of the substrate 130 from one end to the opposite end of the substrate. The sample well 140 may load or add sample material mixture to the substrate 130 and the microchannels of the substrate. The sample well 140 may load an approximately equivalent amount of sample material mixture into each microchannel of the substrate. In some embodiments, the sample material mixture may be loaded with a sample well when the diameter of the microchannels ranges from about 100 μm to about 500 μm. In some embodiments, the sample well 140 may contain a spreading implement at the bottom of the sample well 140. The spreading implement, may be in contact with the substrate 130 to distribute sample material mixture into the microchannels and off of the surface of the substrate. The spreading instrument may move across one end to the opposite end of the substrate 130 to distribute sample material mixture into the microchannels of the substrate. In one embodiment, the method of the present disclosure contemplates a distribution of cellular material that may be 1 to 1000 cells, 1 to 500 cells, 1 to 100 cells, 1 to 50 cells or about 1 to 5 cells in a microchannel of the substrate.

In another embodiment, a sample material mixture is added or loaded into the cassette through a fill port located on the bottom cover. In some embodiments, about $1 \times 10^6$ to $100 \times 10^9$ cells are loaded into the cassette. In various embodiments, the sample material mixture is directly added or loaded onto the substrate. In some embodiments, the substrate may be flooded with the sample material mixture. The sample material mixture may move into the microchannels of the substrate through capillary action. In some embodiments, the substrate may be flooded with the sample material mixture when the diameter of the microchannels ranges from about 10 nm to about 100 μm. In another embodiment, the microchannels of the substrate may be filled with the sample material mixture by placing a hanging drop from the bottom cover to a position above the microchannel. In some embodiments, the hanging drop may be in contact with the microchannel. In some embodiments, the hanging drop may range in volume from about 10 μL to about 900 mL. The sample material mixture may move into the microchannels through capillary action. In another embodiment, the sample material mixture may be received by the sample well. The sample well may move across the top surface of the substrate from one end to the opposite end of the substrate. The sample well may load or add sample material mixture to the substrate and the microchannels of the substrate. The sample well can load an approximately equivalent amount of sample material mixture into each microchannel of the substrate. In some embodiments, the sample material mixture may be loaded with a sample well when the diameter of the microchannels ranges from about 100 μm to about 500 μm. In some embodiments, the sample well may contain a spreading implement at the bottom of the sample well. The spreading implement, may be in contact with the substrate to distribute sample material into the microchannels. The spreading instrument may move across one end to the opposite end of the substrate to distribute sample material mixture into the microchannels of the substrate and off of the surface of the substrate. In certain embodiments, the method of the present disclosure contemplates a distribution of cellular material that may be 1 to 1000 cells, 1 to 500 cells, 1 to 100 cells, 1 to 50 cells, and about 1 to 5 cells in at least one of the microchannels of the substrate.

Figure 4E:
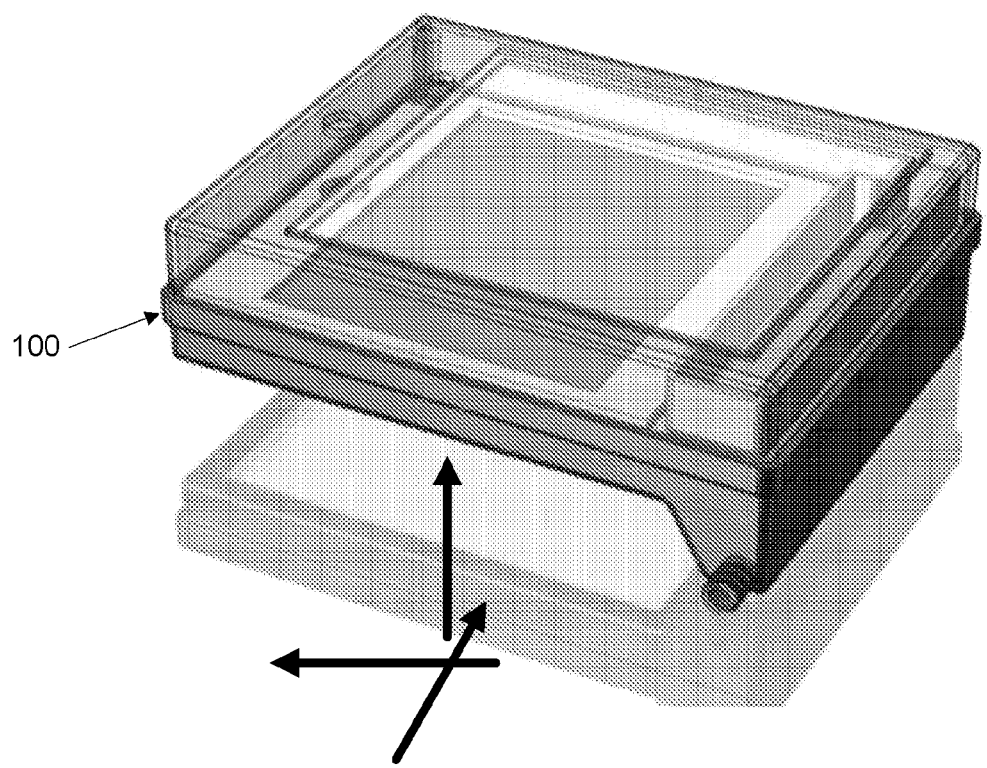
FIG. 4E illustrates one embodiment of scanning target particles through the bottom window of the bottom cover of the cassette.
Figure 4F:
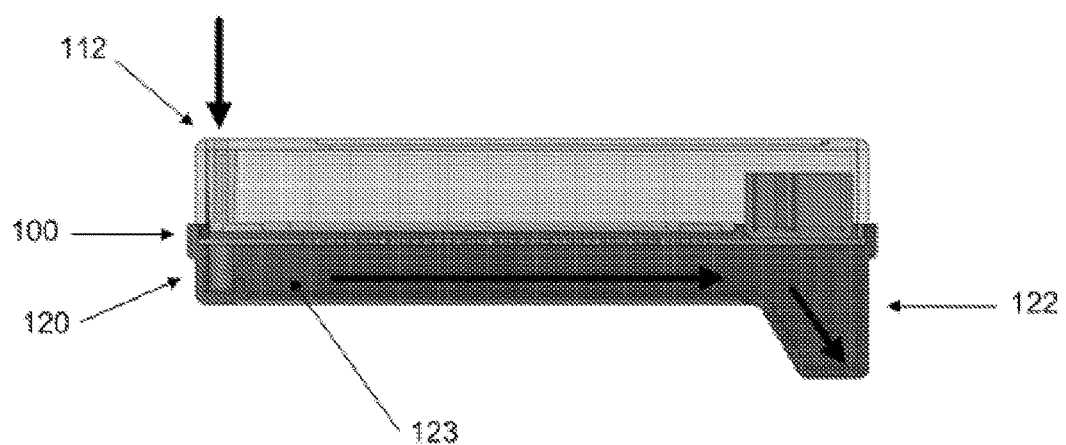
FIG. 4F illustrates one embodiment of flushing the extracted target particles from the internal surface of the bottom cover to the collection well.

After the sample material mixture is loaded into the microchannels of the substrate 100 or loaded onto the first surface of the substrate, the microchannels and the first surface of the substrate are scanned, as depicted in FIG. 4E, to detect one or more target particles. Scanning includes illuminating the microchannels with a specific wavelength (first wavelength) or a set of specific wavelengths, and detecting the target particles with a specific wavelength (second wavelength) or a set of specific wavelengths. For example, the specific wavelengths include wavelengths ranging from about 200 nm to about 1.5 mm. The specific wavelengths for illuminating and detecting may be the same or different. Any wavelength referred to herein, e.g., first wavelength, second wavelength, third wavelength, fourth wavelength, and wavelength $X_1$, may be independently selected from at least one wavelength within a range of the electromagnetic spectrum extending from the ultraviolet to the far infrared. The first, second, third, and fourth wavelengths and wavelength $X_1$ are independently selected from one or more wavelengths ranging from about 200 nm to about 1.5 mm. In some embodiments, the first, second, third, and fourth wavelengths and wavelength $X_1$ are independently selected from wavelengths ranging from about 400 nm to about 700 nm. For example, illuminating wavelengths may include 350 nm to 400 nm to illuminate 4',6-diamidino-2-phenylindole (DAPI); 400 nm to 450 nm to excite dyes such as BV421™, cyan fluorescent protein (CFP), AmCyan, and Pacific Blue™; 450 nm to 500 nm to excite dyes such as green fluorescent protein (GFP), Peridinin Chlorophyll Protein Complex (PerCP), and PerCP-Cy™ 5.5; 500 nm to 600 nm to illuminate dyes such as R-phycoerythrin (PE), PE-Texas Red®, Texas Red®, 7-aminoactinomycin D (7-AAD), PE-Cy™ 5, PE-Cy™ 5.5, PE-Cy™ 7, and PE-Dazzle™; 600 nm to 700 nm to excite dyes such as allophycocyanin (APC), Alexa Fluor® 647, Alexa Fluor® 700, Alexa Fluor® 780, and APC-Cy™ 7; and 800 nm to 1200 nm to illuminate $AG_2SE$ Quantum dots or single-walled carbon nanotubes (SWNT). Detection wavelengths may include 350 nm to 400 nm and 400-500 nm to detect a dye such as BV421™; 500 nm to 600 nm to detect dyes such as green fluorescent protein (GFP) and Peridinin Chlorophyll Protein Complex (PerCP); 600 nm to 700 nm, 800 nm to 900 nm, 900 nm to 1100 nm, and 1100 nm to 1300 nm to detect single-walled carbon nanotubes (SWNT) and $AG_2SE$ Quantum dots; and 1300 nm to 1500 nm to detect $AG_2SE$ Quantum dots and single-walled carbon nanotubes (SWNT). In addition, the electromagnetic radiation source may illuminate one wavelength as in a laser source or a band of wavelength as in LED light sources. The electromagnetic radiation source may be used alone, or a light path may be generated containing multiple wavelengths or multiple powers simultaneously. Different wavelengths or powers may also be temporally isolated, meaning only one wavelength or power occupies the optical train at a given time, but multiple different wavelengths or powers can be swapped. Illumination times can range from 10 femto-sec to 5 sec. Source light may also be spatially separated, meaning that light of a different wavelength or power may enter the cassette at the same time but at different locations. Light sources may also be spatially and temporally separated. The source may be capable of emitting multiple wavelengths in order to accommodate different absorption properties of varying materials and labels. In certain embodiments, the desired specificity will be a single cell per microchannel. In some embodiments, electromagnetic radiation is transmitted from the source to the substrate through a transmissive portion in a cassette. The signals from each microchannel are scanned to locate the microchannels of interest. In a one embodiment, a microchannel is screened by detecting an electromagnetic signal emitted from a label in each cavity.

The target particles may be identified by a unique emission profile. In some embodiments, illuminating a microchannel with a plurality of different wavelengths and detecting an emission from the microchannel corresponds with emissions from one or more target particles. In another embodiment, illuminating a microchannel with a single wavelength and detecting a plurality of emissions from the microchannel corresponds with emissions from one or more target particles. In another embodiment, illuminating a microchannel with a plurality of wavelengths and detecting a plurality of emissions from the microchannel corresponds with emissions from one or more target particles.

Upon detecting the particle of interest, the particle of interest may be extracted, as depicted in FIG. 4E, from the substrate 130. Individual microchannels containing the particle of interest can be extracted using a variety of methods. In one embodiment, the method includes pressure ejection. For example, a substrate is covered by a plastic film. The method further provides a laser capable of making a hole through the plastic film, thereby exposing the spatially addressed microchannel. Subsequently, exposure to pressure source (e.g., air pressure) expels the contents from the spatially addressed microchannel. In another embodiment, the method of extraction involves focusing electromagnetic radiation at the microchannel of the substrate to be absorbed by opaque material. The energy of incident radiation converts into the heat of vaporization of a portion of the aqueous solution to generate an expansion of the target particles or evaporation that expels at least part of the target particles from the microchannel of the substrate.

In certain embodiments, extraction from the microchannels of the substrate is accomplished by excitation of one or more particles, e.g., opaque particles, in the microchannels of the substrate, wherein excitation energy is focused on the particles. Accordingly, some embodiments employ energy absorbing particles in the cavities and an electromagnetic radiation source capable of delivering electromagnetic radiation of the particles in each microchannel of the substrate. Excitation of the particles in a microchannel may result in a release of energy that disrupts and releases the solution or mixture from the microchannel. In certain embodiments, energy is transferred to the particles with minimal or no increase in the temperature of the solution or mixture within the microchannel. In certain aspects, a sequence of pulses repeatedly agitates magnetic beads in a microchannel to disrupt a meniscus, which expels target cellular material from the substrate. In certain aspects, the extracted cellular material is expelled onto the internal surface of the bottom cover.

The target particles are extracted from the microchannel with a specific wavelength (third wavelength) that may be selected wavelengths ranging from 200 nm to about 1.5 mm. In some embodiments, the target particles are extracted from the microchannel with a specific wavelength (third wavelength) that may be selected wavelengths ranging from about 350 nm to about 1200 nm. The specific wavelength for extraction may be the same or different from the wavelengths used for illuminating and detecting the target particles. The first, second, and third wavelengths referred to herein are independently selected from wavelengths ranging from about 200 nm to about 1.5 mm. In addition, the electromagnetic radiation source may be the same or different from the source used for illuminating and detecting the target particles. The source may be capable of emitting multiple wavelengths in order to accommodate different absorption spectra of varying materials and labels. In addition, the electromagnetic radiation source used for illuminating, detecting, and extraction may be the same or different from each other.

Figure 4G:
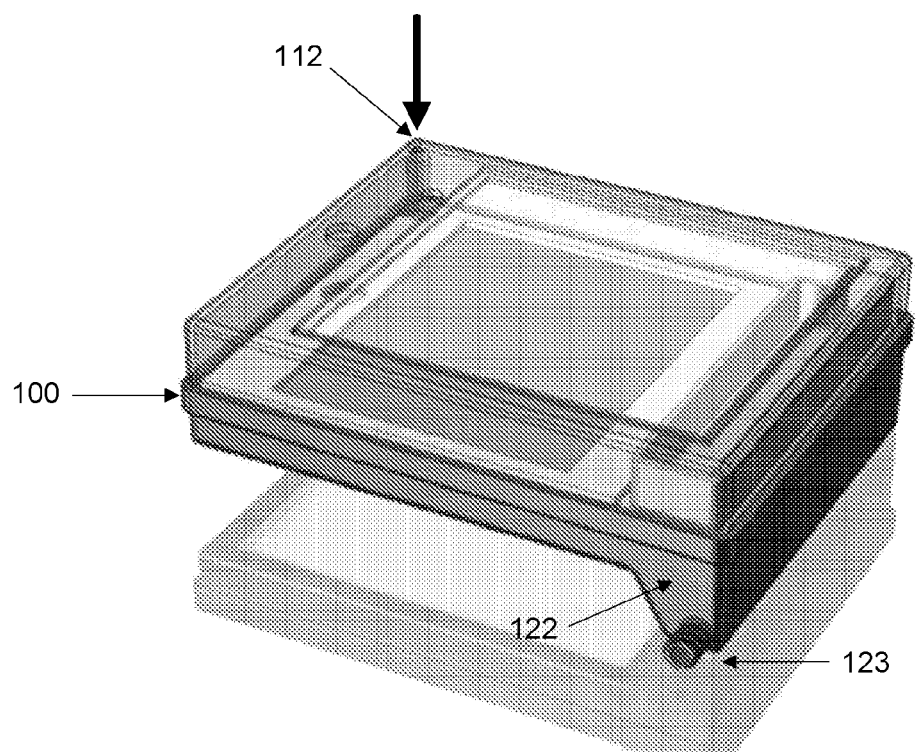
FIG. 4G illustrates one embodiment of flushing and recovering the extracted target particles from the release port.

As previously discussed, the extracted target particles may collect on the internal surface of the bottom cover 120. As depicted in FIG. 4F, a solution may be added to the cassette 100 through a fill port located on the top cover. In another embodiment, an aqueous solution may be added to the cassette 100 through a fill port located on the bottom cover. In one embodiment, the solution is buffer. In one embodiment, buffer may be added to the accessory material port 112 located on the top cover 110. As depicted in FIG. 4F, the buffer may move the extracted target particles from the internal surface of the bottom cover to the collection well 122. Additionally, as depicted in FIG. 4G, the extracted target particles may be removed from the cassette 100 through the receiving port 123. The extracted target particles may be retrieved into a previously sterilized container. The extracted target particles may be retrieved under sterile conditions. The extracted target particles may be free from contaminants.

Pharmaceutical Compositions and Preparations Thereof

In some aspects, the devices and methods of the disclosure enable the preparation of pharmaceutical compositions of cells, e.g., hematopoietic stem cells (HSCs) and/or hematopoietic stem progenitor cells (HSPCs), with unprecedented sterility, purity, and viability. The pharmaceutical compositions of the present disclosure may be prepared by screening cellular material and extracting cells with desired phenotype or phenotypes.

In particular, the disclosure provides methods of sorting cellular material, e.g., cells obtained from a subject. In some embodiments, the methods comprise screening cellular material, e.g., with the scanner systems and methods described herein, at a rate of approximately 100,000 cells per second or more. The methods may comprise screening cellular material to identify cells with a desired phenotype at a rate of approximately 150,000 cells per second or more, approximately 200,000 cells per second or more, approximately 250,000 cells per second or more, approximately 300,000 cells per second or more, approximately 350,000 cells per second or more, approximately 400,000 cells per second or more, approximately 450,000 cells per second or more, approximately 500,000 cells per second or more, approximately 550,000 cells per second or more, approximately 600,000 cells per second or more, approximately 650,000 cells per second or more, approximately 700,000 cells per second or more, approximately 750,000 cells per second or more, approximately 800,000 cells per second or more, approximately 850,000 cells per second or more, approximately 900,000 cells per second or more, or approximately 950,000 cells per second or more. In certain embodiments, the methods comprise screening cellular material to identify cells of a desired phenotype at a rate of approximately 1,000,000 cells per second or more, approximately 1,500,000 cells per second or more, approximately 2,000,000 cells per second or more, approximately 2,500,000 cells per second or more, approximately 3,000,000 cells per second or more, approximately 3,500,000 cells per second or more, approximately 4,000,000 cells per second or more, approximately 4,500,000 cells per second or more, or approximately 5,000,000 cells per second or more. In certain embodiments, the methods comprise screening cellular material to identify cells of a desired phenotype at a rate of approximately 100,000 cells per second to about 2,000,000 cells per second.

The present disclosure provides methods for screening cellar material, e.g., with the scanner systems and methods described herein, to identify HSCs and/or HSPCs with a desired phenotype. In some embodiments, the methods comprise screening cellular material wherein less than 10% of the original cellular material comprises HSCs and/or HSPCs, such as less than 9%, less than 8%, less than 7%, less than 6%, less than 5%, less than 4%, less than 3%, less than 2% or even less than 1% of the original cellular material comprises HSCs and/or HSPCs.

In some aspects, the present disclosure provides methods for extracting cells from the original cellular material, e.g., cells obtained from a human subject, wherein the extracted cells are of a desired phenotype at a rate of 100,000 cells per second or more. The methods may comprise extracting cells of a desired phenotype or phenotypes from the cellular material at a rate of approximately 150,000 cells per second or more, approximately 200,000 cells per second or more, approximately 250,000 cells per second or more, approximately 300,000 cells per second or more, approximately 350,000 cells per second or more, approximately 400,000 cells per second or more, approximately 450,000 cells per second or more, approximately 500,000 cells per second or more, approximately 550,000 cells per second or more, approximately 600,000 cells per second or more, approximately 650,000 cells per second or more, approximately 700,000 cells per second or more, approximately 750,000 cells per second or more, approximately 800,000 cells per second or more, approximately 850,000 cells per second or more, approximately 900,000 cells per second or more, or approximately 950,000 cells per second or more. In certain embodiments, the methods comprise extracting cells of a desired phenotype or phenotypes at a rate of approximately 1,000,000 cells per second or more, approximately 1,500,000 cells per second or more, approximately 2,000,000 cells per second or more, approximately 2,500,000 cells per second or more, approximately 3,000,000 cells per second or more, approximately 3,500,000 cells per second or more, approximately 4,000,000 cells per second or more, approximately 4,500,000 cells per second or more, or approximately 5,000,000 cells per second or more. The methods may comprise extracting cells of a desired phenotype or phenotypes from the cellular material at a rate of approximately 150,000 cells per second to about 2,000,000 cells per second. In certain embodiments, greater than 90%, greater than 92%, greater than 95%, greater than 98%, or greater than 99% of the extracted cells are HSCs and/or HSPCs.

In some embodiments, the methods comprise extracting cells of a desired phenotype wherein the resulting extract has very high purity for said desired phenotype. Extracting cells may produce a cell extract wherein approximately 95% or more of the cell extract are cells of a desired phenotype. The methods may comprise extracting cells wherein approximately 96% or more of the cell extract, approximately 97% or more of the cell extract, approximately 98% or more of the cell extract, approximately 99% or more of the cell extract, are cells of a desired phenotype. The extracted cells, such as extracted HSCs and/or HSPCs, may comprise cells with a desired phenotype or phenotypes, e.g., 95% or more of the cell extract has the desired phenotype or phenotypes. In certain embodiments, 96% or more of the cell extract, 97% or more of the cell extract, 98% or more of the cell extract, or 99% or more of the cell extract are cells of the desired phenotype or phenotypes.

In some embodiments, the methods comprise extracting cells of a desired phenotype, wherein the cell extract has high viability. Viability of the cells may be measure in terms of cell survival subsequent to extracting the cells. Subsequent to extracting the cells may include measuring the survival of the cells approximately 1 minute after to about 5 hours after extracting the cells. In some embodiments, the methods comprise extracting cells thereby producing a cell extract wherein the cell extract has a viability of approximately greater than 95%. In certain embodiments, the cell extract has a viability of greater than 96%, greater than 97%, greater than 98%, greater than 99%. The methods of the present disclosure may result in extracting cells of a desired phenotype, wherein the cell extract has sterility suitable for therapeutic use without the need for additional sterilization procedures. The cell extract may be essentially free of pathogens and other contaminants, e.g., the cell extract has less than 1% pathogens, less than 0.05% of pathogens, less than 0.01% of pathogens, or less than 0.005% of pathogens. In certain embodiments, methods of the disclosure enable the preparation of cell extracts with improved therapeutic properties, e.g., negligible graft versus host disease.

In some aspects, the present disclosure provides pharmaceutical compositions comprising cell extracts with one or more of the following characteristics: (a) greater than 90%, greater than 95%, or greater than 99% of the cells of the cell extract are HSCs and/or HSPCs; (b) the cell extract is essentially free of pathogens, e.g., less than 1%, less than 0.5%, less than 0.05%, or less than 0.01% of pathogens; (c) the cell extract has a purity for cells of the desired phenotypes of greater than 95%, greater than 96%, greater than 97%, greater than 98%, or greater than 99% of the cells in the extract; (d) the extract is suitable for therapeutic use without additional sterilization procedures; and (e) greater than 90% of the cell extract is viable as determined following extraction, e.g., viability measured within 2 hours of extraction.

The present disclosure provides a therapeutic composition comprising cells, wherein greater than 95% of the cells of the compositions are HSCs and/or HSPCs, and greater than 95% of the cells are of a desired phenotype or phenotypes. The present disclosure provides a therapeutic composition comprising cells, wherein greater than 95% of the cells of the compositions are HSCs and/or HSPCs, greater than 95% of the cells are of a desired phenotype or phenotypes, and the composition comprises a negligible amount of pathogens, e.g., less than 0.1%, less than 0.05%, or less than 0.001% of pathogens. The present disclosure provides a therapeutic composition comprising cells, wherein greater than 95% of the cells of the compositions are HSCs and/or HSPCs, greater than 95% of the cells are of a desired phenotype or phenotypes, and less than 0.009%, less than 0.008%, less than 0.007%, less than 0.006%, less than 0.005%, less than 0.004%, less than 0.003%, less than 0.002%, or less than 0.001% of the cells are naïve T cells. The present disclosure provides a therapeutic composition comprising cells, wherein greater than 95% of the cells of the compositions are HSCs and or HSPCs, greater than 95% of the cells are of a desired phenotype, and 96% or more, 97% or more, 98% or more, or 99% or more of the cells are viable.

Kits

In another aspect, the present disclosure is directed to kits for sorting target particles. In one embodiment, the kits include a cassette for sorting target particles. In certain embodiments, the cassette contains an enclosed housing unit, a transmissive portion, a substrate encapsulated in the enclosed housing unit, and one or more fill ports. In certain embodiments, the cassette is sterilized prior to the addition of a sample material mixture.

In one embodiment, the kits may also include instructional materials containing directions (i.e., protocols) providing for the use of the cassette for sorting target particles. While the instructional materials typically include written or printed materials, they are not limited to such. Any medium capable of storing such instructions and communicating them to an end user is contemplated by this disclosure. Such media include, but are not limited to electronic storage media (e.g., magnetic discs, tapes, cartridges, chips), optical media (e.g., CD ROM), and the like. Such media may include addresses to internet sites that provide such instructional materials.

Macro-Gel Isolation

The microchannels 610 of the substrate 130 are loaded in a specific way to maintain the integrity of the target particles. In one embodiment, as depicted in FIG. 6, the microchannel 610 of a substrate 130 is loaded with a particle mixture and a sample component mixture.

Figure 6:
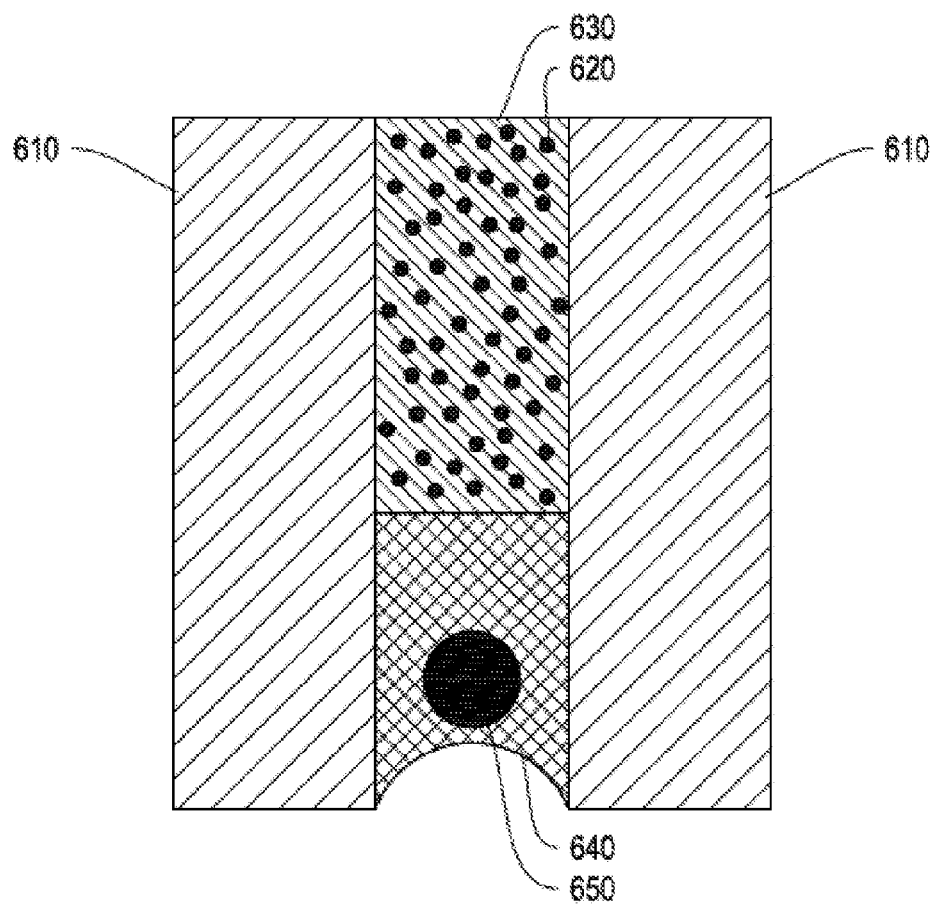
FIG. 6 illustrates one embodiment of loading a sample material mixture into a microchannel of a substrate. The microchannel comprises a first mixture and a second mixture. The first mixture comprises a transparent solution and a plurality of opaque particles. The second mixture comprises of a cellular component and an aqueous solution.

As depicted in FIG. 6, the particle mixture may contain a heterogeneous mixture of opaque particles 620 and a transparent solution 630. In some embodiments, the transparent solution separates the opaque particles from the sample component. In one embodiment, the opaque particles and the sample component are separated by an average distance of 1 µm or more. The transparent solution provides protection to the sample component from energy released from the opaque particles. The opaque particles at least partially absorb electromagnetic radiation and at least partially transfer the energy to the transparent solution. In some embodiments, the transfer of energy to the transparent solution causes vaporization of the surrounding transparent solution. In one embodiment, the opaque particles are not in contact with the sample component. In some embodiments, the transparent solution is also a viscous solution. For example, the transparent solution may be agarose, collagen, matrigel, or alginate. In some embodiments, the opaque particles may have light-scattering properties. The opaque particles may protect the sample component from electromagnetic radiation during extraction. The opaque particles may absorb electromagnetic radiation a specific wavelength. For example, the specific wavelengths include wavelengths ranging from about 200 nm to about 1.5 mm. As depicted in FIG. 6, the sample component mixture contains a sample component 650 and an aqueous solution 640. The sample component may comprise a cell. The aqueous solution may include water, buffer, media, and serum. In some embodiments, the particles mixture and the sample component mixture are in separate layers.

In various embodiments, particles mixture is cast in the microchannel prior to the addition of the sample component mixture. The particles mixture may solidify prior to the addition of the sample component mixture. In some embodiments, the particles mixture is added to microchannel of the substrate, and then the sample component mixture is subsequently added to the microchannel of the substrate. In certain embodiments, an etching solution is added to the microchannel prior to the addition of the sample component mixture. The etching solution may at least partially dissolve the particles mixture. The etching solution may include hydrofluoric acid, a strong acid such as hydrochloric acid, nitric acid, or sulfuric acid, a strong base such as sodium hydroxide or potassium hydroxide, or any other etchant as known to one having skill in the art. The sample component remains viable after scanning and extracting with electromagnetic radiation.

Micro-Gel Isolation

Figure 7A:
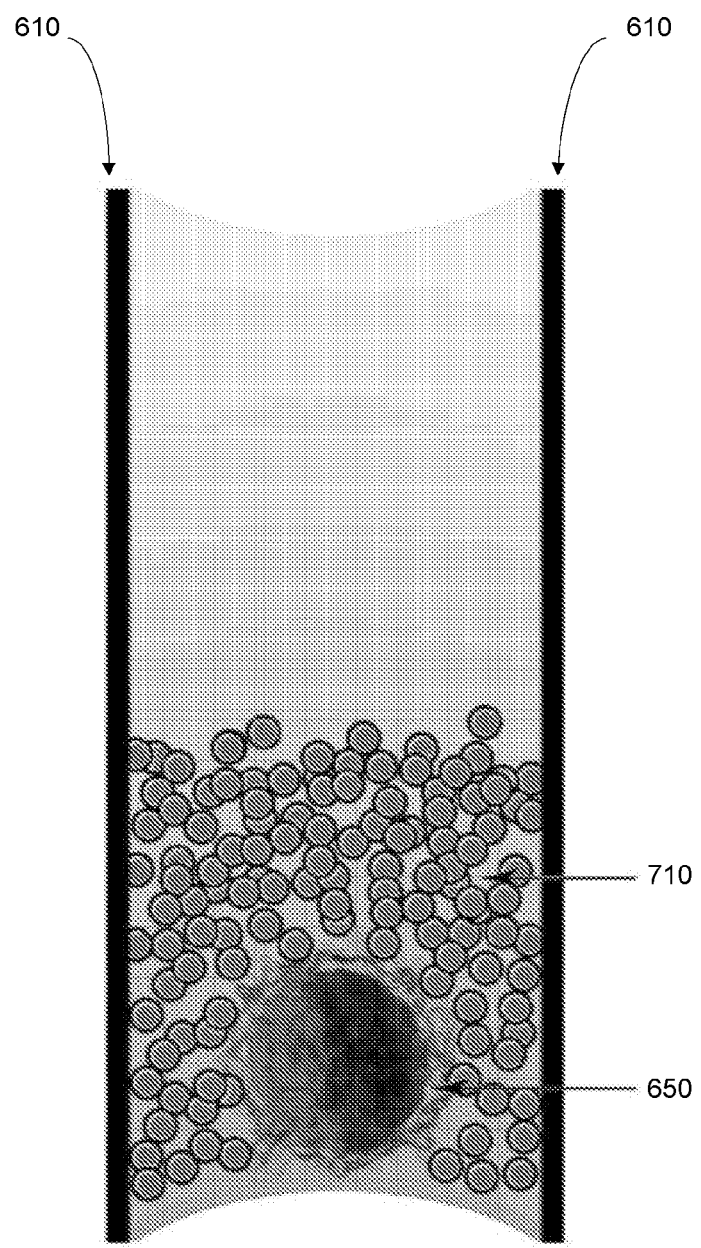
FIG. 7A represents a microchannel of a substrate that is loaded with a cellular component and a plurality of opaque particles.
Figure 7B:
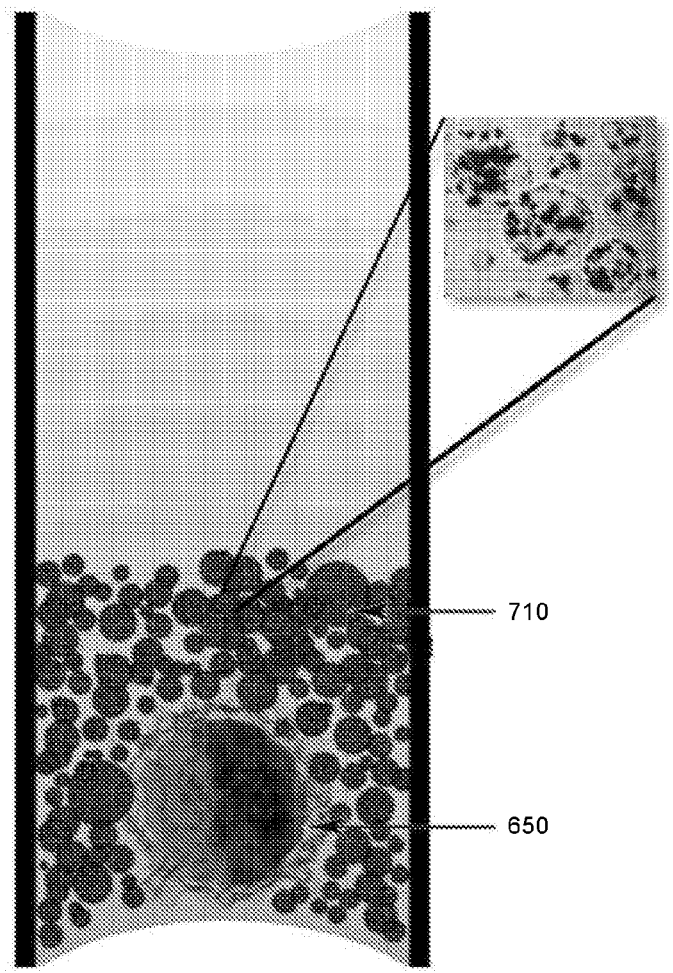
FIG. 7B represents a microchannel of a substrate that is loaded with a cellular component and a plurality of particles comprising an opaque core and a shell surrounding the core.
Figure 7C:
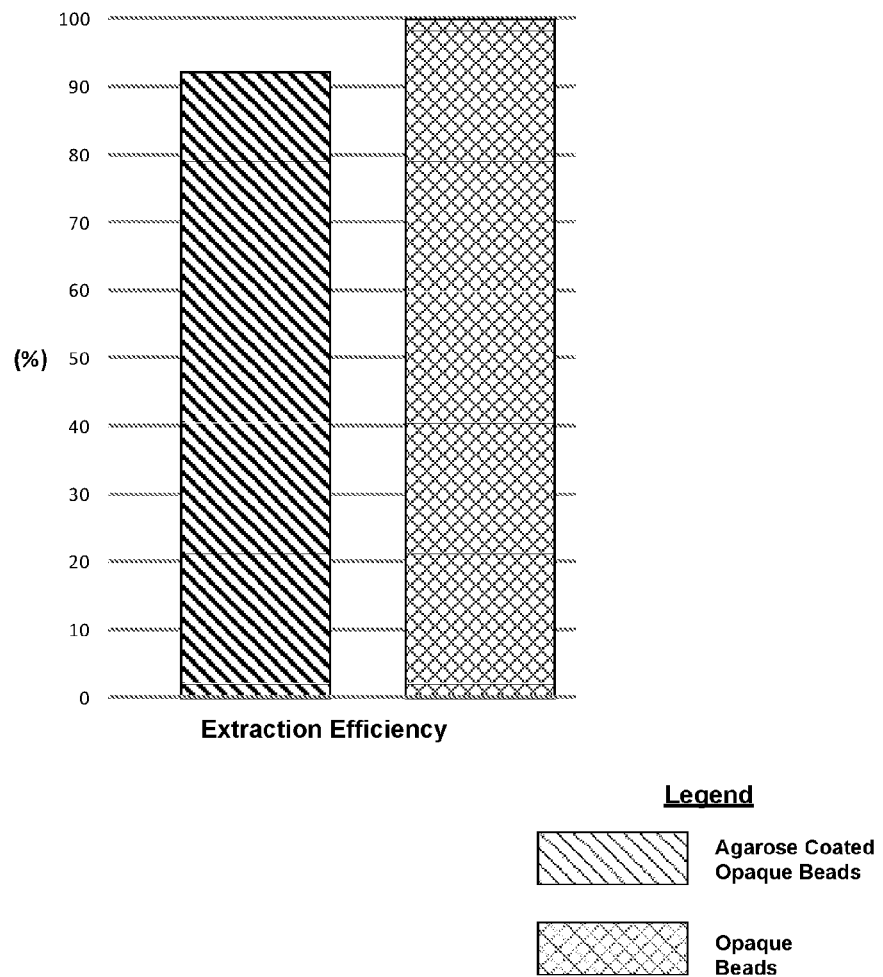
FIG. 7C is a graphical representation of extraction efficiency of cells that were independently loaded with either opaque particles or particles comprising an opaque core and a shell surrounding the core. The graphical representation illustrates that the cells containing opaque particles were extracted with less efficiency than the cells containing particles comprising an opaque core and a shell surrounding the core.
Figure 7D:
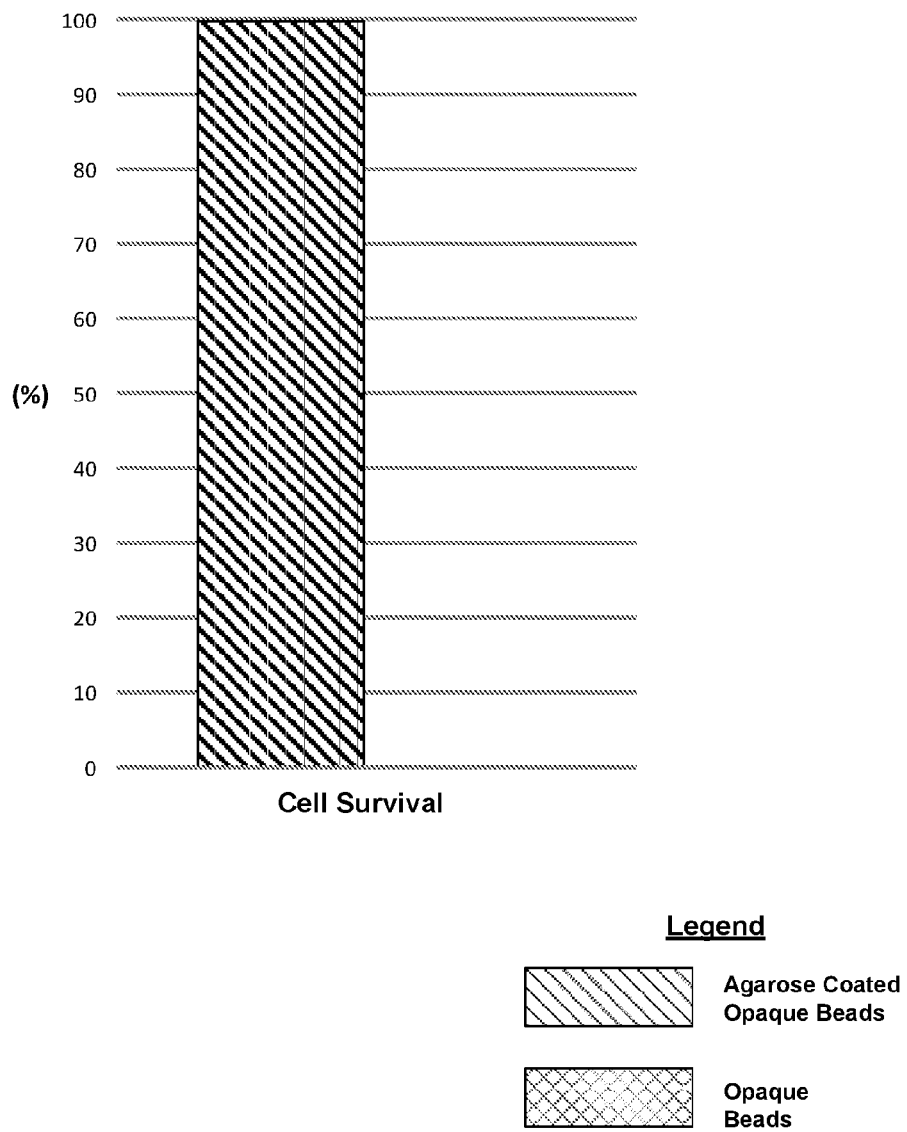
FIG. 7D is a graphical representation of cell survival of cells that were independently loaded with either opaque particles or particles comprising an opaque core and a shell surrounding the core. The graphical representation illustrates that the cells containing opaque particles were less viable than the cells containing particles comprising an opaque core and a shell surrounding the core.

In some embodiments, as depicted in FIG. 7B, sample material and particles containing a shell 710 are simultaneously loaded into the microchannels of the substrate. The particles may comprise an opaque core. An opaque core may comprise of a magnetic bead or a non-magnetic bead. In one embodiment, the opaque core is a magnetic bead. In another aspect, the shell comprises a transparent material. The transparent material may be agarose, collagen, extracellular matrix, alginate, fluid filled biological membranes, micelle, fluid filled lipid, or fatty acid vesicles. In certain embodiments, the particles not containing a shell may be about 20 nm to about 200 µm in diameter. In certain embodiments, the particles containing a shell may be about 520 nm to about 400 µm in diameter. The sample material may be a cell. In these embodiments, the sample material may maintain viability after scanning and extracting with electromagnetic radiation. In some embodiments, the sample material is at least 10% viable. For example, the cells loaded with particles containing a shell were extracted with above 90% extraction efficiency, as depicted in FIG. 7C, and 100% cell survival, as depicted in FIG. 7D.

In another embodiment, sample material and particles containing a shell are sequentially loaded into the microchannels of the substrate. In one embodiment, the sample material is first loaded and then, the particles containing the shell are load. The particles may comprise an opaque core. An opaque core may comprise of a magnetic bead or a non-magnetic bead. In one embodiment, the opaque core is a non-magnetic bead. In another aspect, the shell comprises a transparent material. The transparent material may be agarose, collagen, extracellular matrix, alginate, fluid filled biological membranes, micelle, fluid filled lipid, or fatty acid vesicles. In certain embodiments, the particles not containing a shell may be about 20 nm to about 200 µm in diameter. In certain embodiments, the particles containing a shell may be about 520 nm to about 400 µm in diameter. The sample material may be a cell. In these embodiments, the cellular material may maintain viability after scanning and extracting with electromagnetic radiation. In some embodiments, the sample material is at least 10% viable.

In contrast, sample material loaded with particles without a shell may not maintain viability. In some embodiments, viability of the sample material loaded with particles without a shell may be about 9% or lower. For example, for cells that were loaded with particles without a shell, as depicted in FIG. 7A, although the extraction efficiency was 100%, as shown in FIG. 7C, the cell survival rate was 0%, as shown in FIG. 7D.

In-Pore Spacer

Figure 8A:
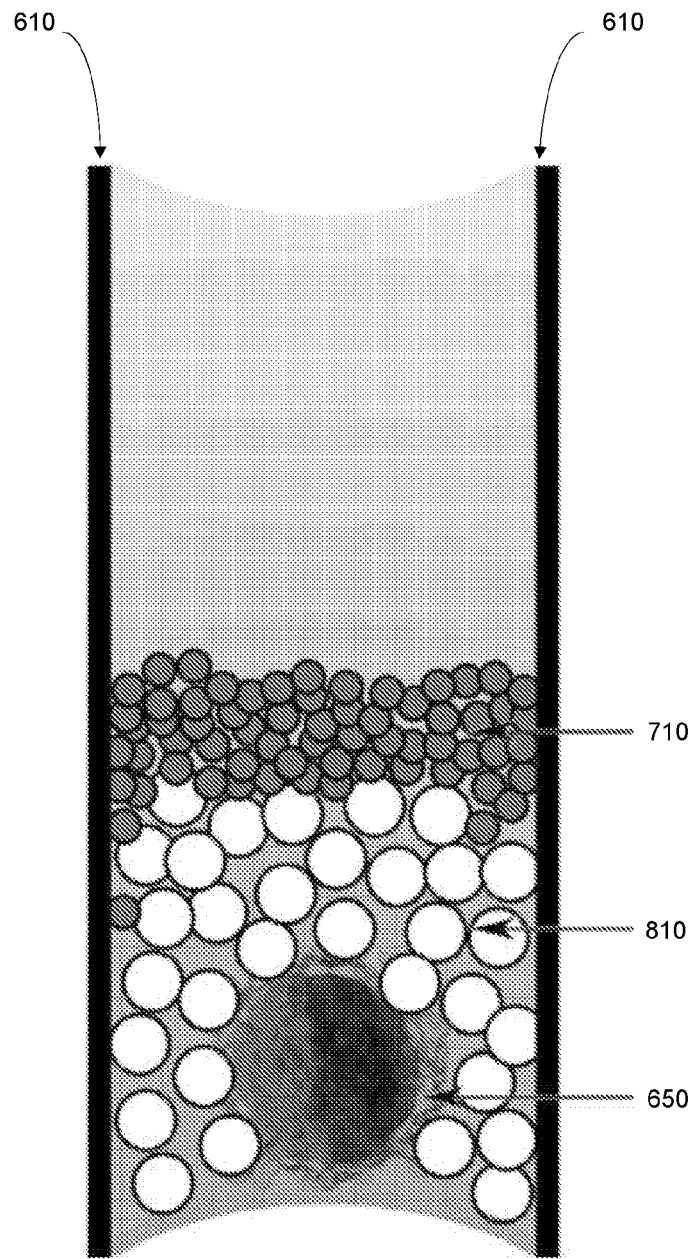
FIG. 8A represents a microchannel of a substrate that is loaded with a mixture comprising a cellular component, a plurality of magnetic particles, and a plurality of non-magnetic particles.

The microchannels 610 of the substrate 130 are loaded in a specific way to maintain the integrity of the sample component. In some embodiments, as depicted in FIG. 8A, the sample component may be loaded with magnetic particles 710 and non-magnetic particles 810. In some embodiments, the mixture consists of magnetic particles 710 and the non-magnetic particles at a weight ratio of about 1:0.5 to 1:10. In one embodiment, the magnetic particles in the microchannel are in a concentration of about 1 mg/mL or about 30 mg/mL. The non-magnetic particles in the microchannel are in a concentration of about 1 mg/mL to about 100 mg/mL. In some embodiments, the sample component is an intact or lysed cell. The non-magnetic particles 810 comprise a material that does not damage cells when excited with electromagnetic radiation. For example, the non-magnetic particles may comprise silica, plastic, agarose, or alginate. In some embodiments, a magnetic force is applied above the microchannel to attract the magnetic particles 710 to form a layer above the non-magnetic particles 810, as depicted in FIG. 8A. The magnetic particles 710 are located above the non-magnetic particles 810. In another embodiment, a magnetic force is applied below to microchannel to attract the magnetic particles to form a layer below the non-magnetic particles. The magnetic particles 710 are separated from the sample material, by at least 1 µm or more.

Figure 8B:
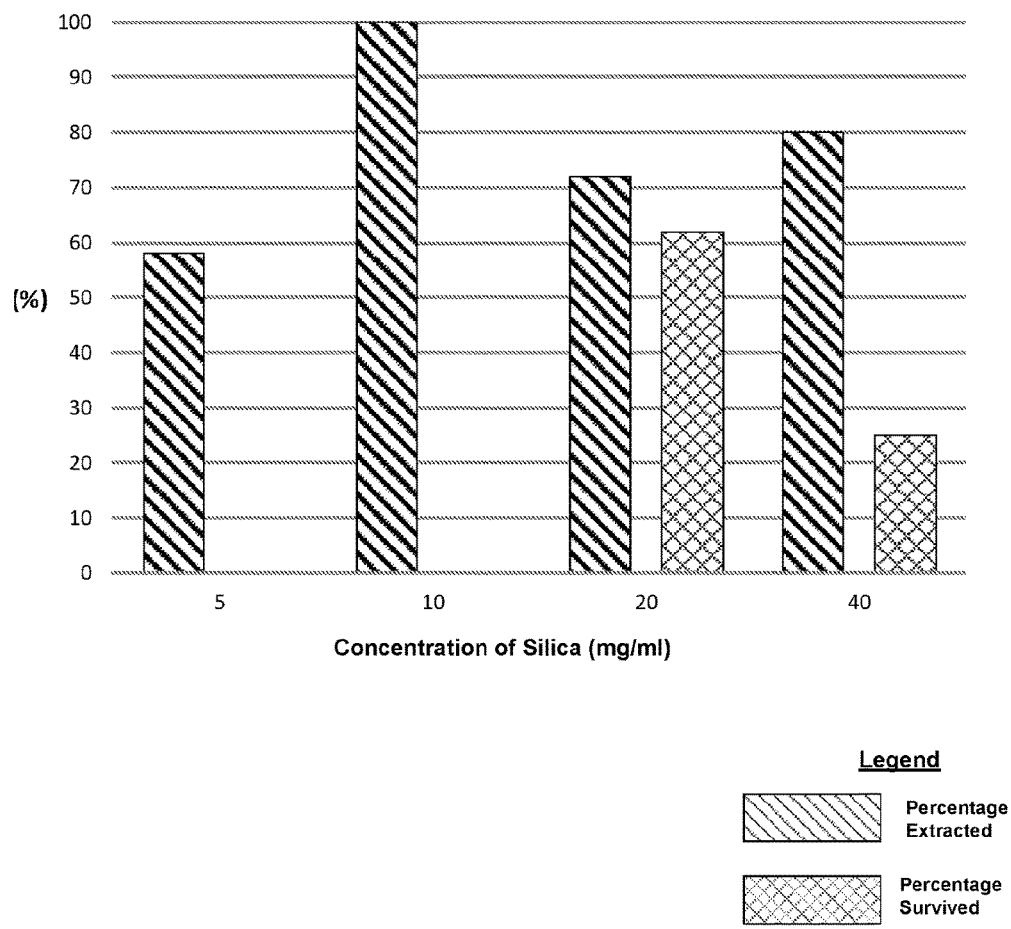
FIG. 8B is a graphical representation of extraction efficiency and rate of survival of cells that were loaded with varying amounts of non-magnetic particles, and a set amount of magnetic particles.

The ratio of magnetic particles 710 to non-magnetic particles 810 plays a role in extraction efficiency and cell viability of the cellular material. For example, as depicted in FIG. 8B, when the magnetic particles 710 are held constant at 15 mg/mL, the extraction efficiency and cell survival rate varied depending on the concentration of non-magnetic particles. In particular, at 5 mg/mL of non-magnetic particles, the extraction efficiency was about 57% and cell survival was 0%; at 10 mg/mL of non-magnetic particles, the extraction efficiency was about 100% and cell survival was 0%; at 20 mg/mL of non-magnetic particles, the extraction efficiency was about 73% and cell survival was about 63%; and at 40 mg/mL of non-magnetic particles, the extraction efficiency was about 80% and cell survival was about 25%.

In another aspect, the sample component may be loaded with opaque particles in a sequential manner. First, the sample component and a plurality of opaque particles that do not absorb a specific wavelength are loaded to the microchannel of the substrate. The specific wavelengths include wavelengths ranging from about 200 nm to about 1.5 mm. Then, opaque particles which absorb a specific wavelength are loaded to the microchannel. In one embodiment, the opaque particles comprise of magnetic and non-magnetic particles. In one embodiment, the opaque particles comprise of magnetic particles.

Sequential Loading

Figure 9A:
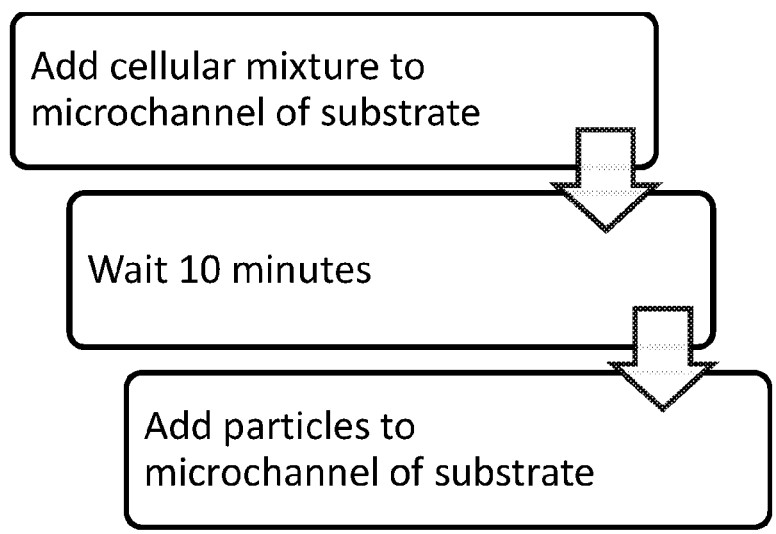
FIG. 9A represents an illustrative embodiment of the sequential loading method.
Figure 9B:
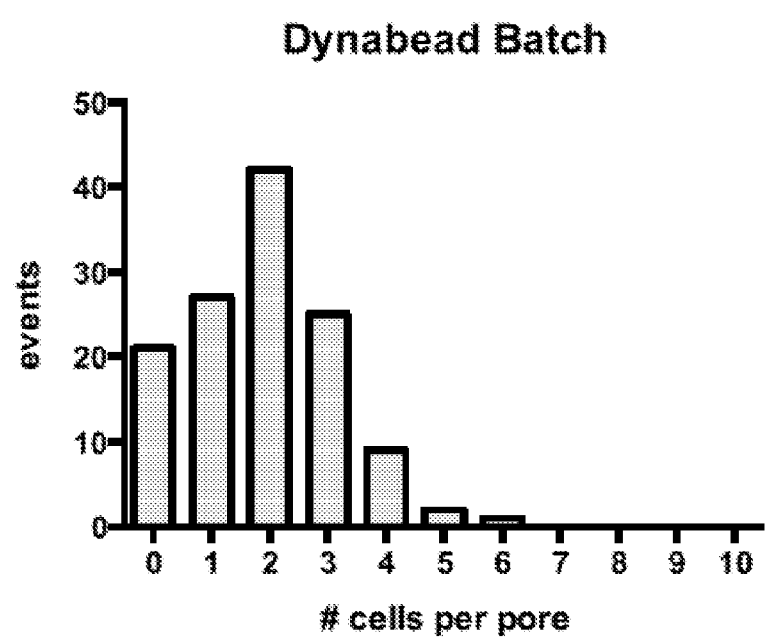
FIG. 9B is a graphical representation of the number of cells per microchannel of the substrate. The cells were loaded onto the substrate comprising a plurality of microchannels with Dynabeads® in a mixed batch.
Figure 9C:
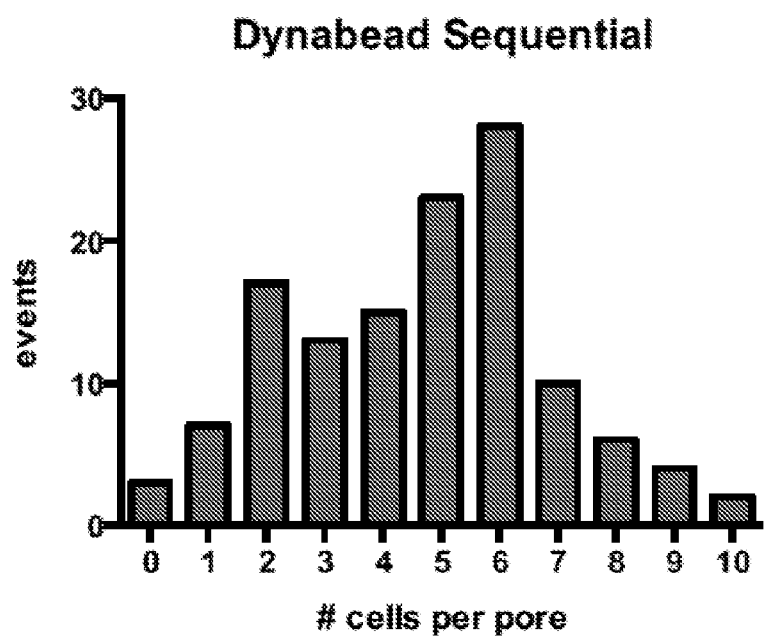
FIG. 9C is a graphical representation of the number of cells per microchannel of the substrate. The cells were loaded onto the substrate comprising a plurality of microchannels with Dynabeads® in a sequential manner.
Figure 9D:
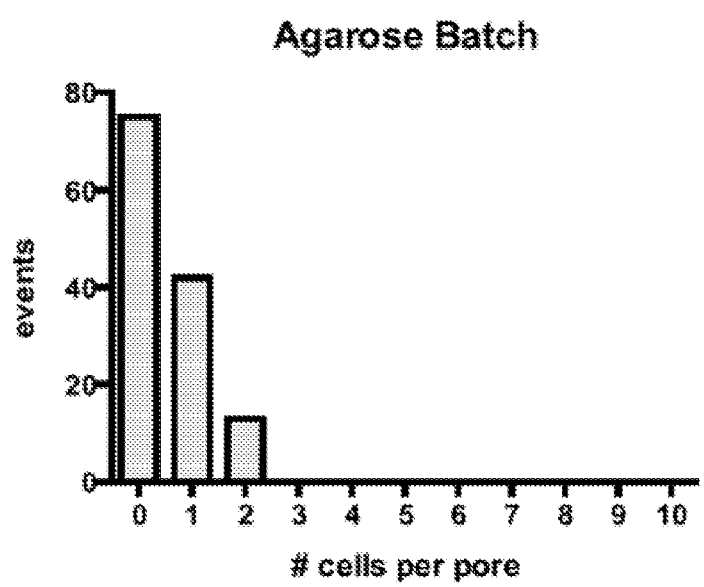
FIG. 9D is a graphical representation of the number of cells per microchannel of the substrate. The cells were loaded onto the substrate comprising a plurality of microchannels with agarose in a mixed batch.
Figure 9E:
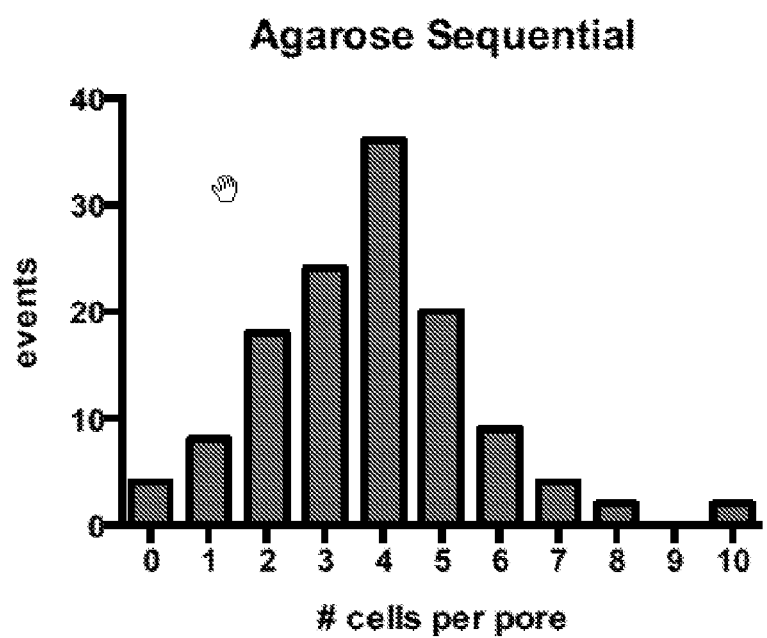
FIG. 9E is a graphical representation of the number of cells per microchannel of the substrate. The cells were loaded onto the substrate comprising a plurality of microchannels with agarose in a sequential manner.
Figure 9F:
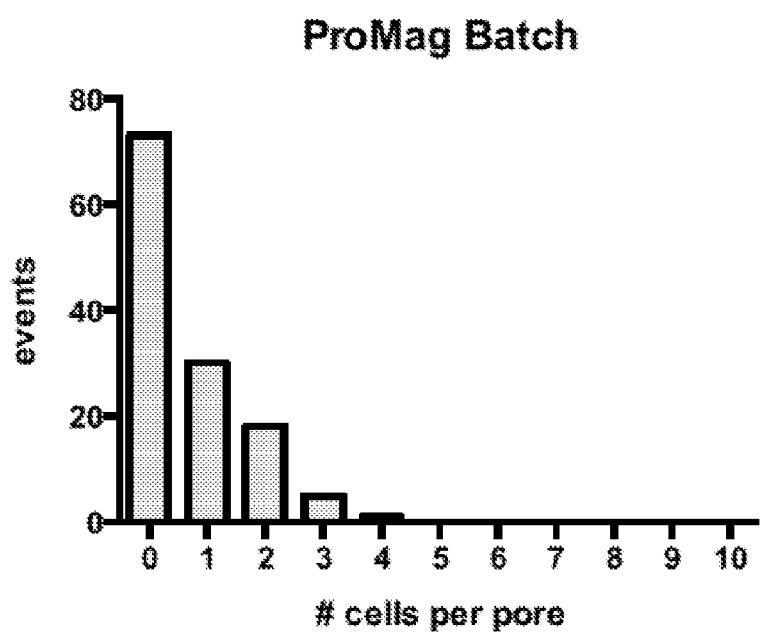
FIG. 9F is a graphical representation of the number of cells per microchannel of the substrate. The cells were loaded onto the substrate comprising a plurality of microchannels with ProMag® in a mixed batch.
Figure 9G:
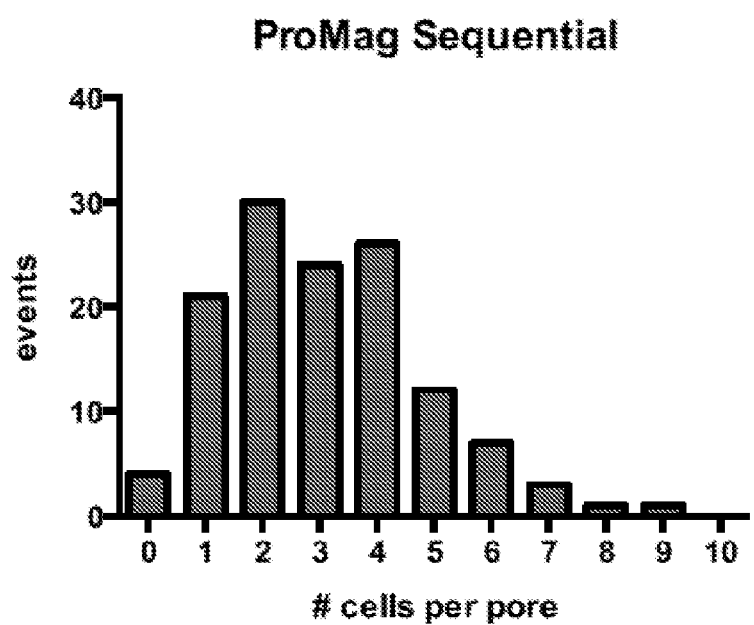
FIG. 9G is a graphical representation of the number of cells per microchannel of the substrate. The cells were loaded onto the substrate comprising a plurality of microchannels with ProMag® in a sequential manner.
Figure 9H:
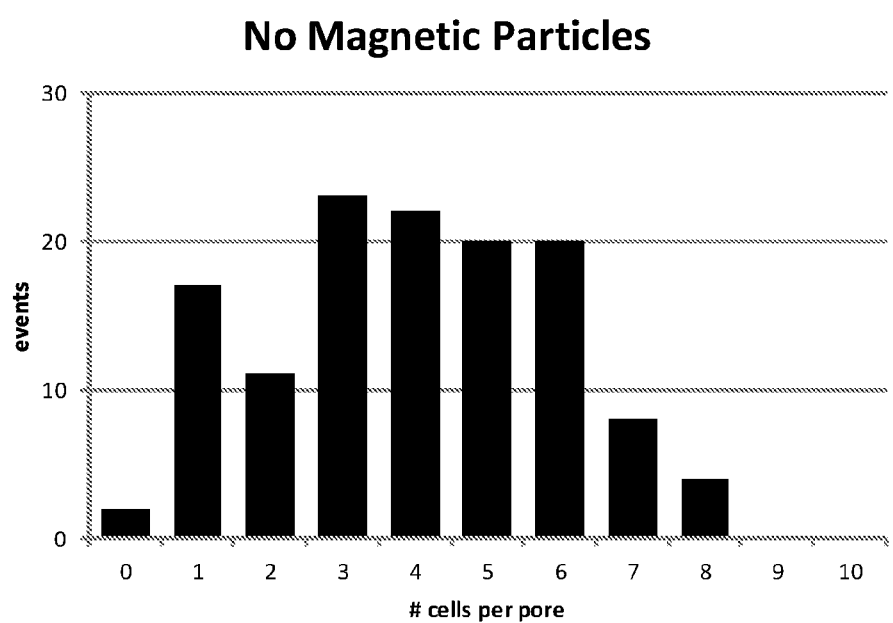
FIG. 9H is a graphical representation of the number of cells per microchannel of the substrate. The cells were loaded onto the substrate comprising a plurality of microchannels with no opaque particles.

In various embodiments of a method of quantifying the number of sample material in a microchannel of a substrate, the microchannels 610 of the substrate 130 may be sequentially loaded to enhance sample visibility. In certain embodiments, sample material may comprise a cell. In an exemplary embodiment, as depicted in FIG. 9A, the sample mixture is first added to the microchannels of the substrate, and then, the particles are subsequently added to the microchannels of the substrate. Then, the number of sample material in the microchannels may be quantified. In various embodiments, the particles are opaque beads. For example, opaque beads include Dynabead®, agarose, and ProMag®. In some embodiments, the particles are added to the microchannels of the substrate after about 5 mins or more after the addition of sample mixture. In certain embodiments, the particles are added to the microchannels of the substrate after about 10 mins after the addition of sample mixture. In one embodiment, the amount of sample material may be quantified by microscopy. In certain embodiments, the amount of cells may be quantified by microscopy. In some embodiments, such sequential loading prevent the cells from being obscured from view by the beads. For example, as depicted in FIG. 9B to 9G, three types of particles (i.e., Dynabead®, agarose, and ProMag®) were applied to the microchannels of a substrate in both a sequential manner and in a mixed batch with cellular material. Dynabead® was used in FIGS. 9B and 9C, agarose was used in FIGS. 9D and 9E, and ProMag® was used in FIGS. 9F and 9G. Additionally, FIG. 9H shows a graphical representation of the control that contained no particles. The accuracy of the cell count in each microchannel utilizing the sequential loading method and the mixed batch method was compared to the control in FIG. 9H. As shown in FIG. 9B to 9G, the microchannels that were loaded with the sequential loading method (FIGS. 9C, 9E, and 9G) more closely resembled the cell count in the control (FIG. 9H) than the microchannels that were loaded with the mixed batch method (FIGS. 9B, 9D, and 9F).

Fluorescence Displacement

Figure 10A:
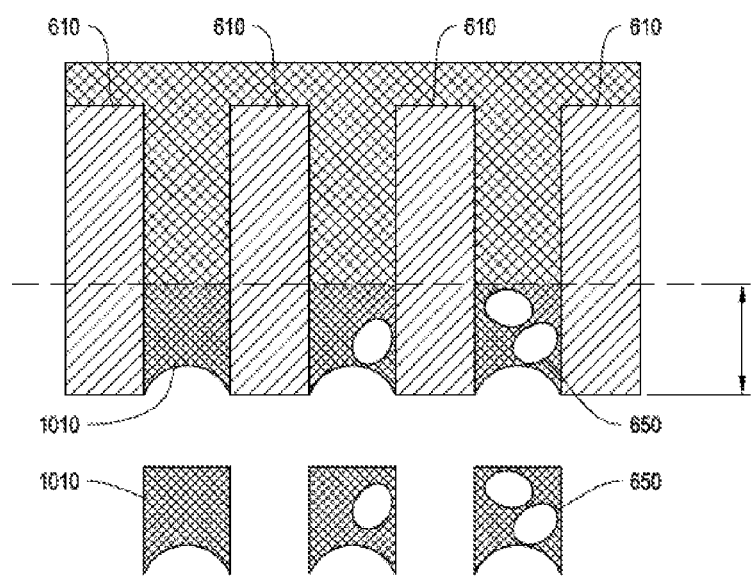
FIG. 10A illustrates the microchannels of a substrate loaded with fluorescent material and cells. The fluorescent material is displaced in the presence of cells. The number of cells in the microchannel is quantified by the amount of fluorescent displacement. The fluorescence signal is more intense in channels with a low cell count or is less intense in channels with a high cell count.
Figure 10B:
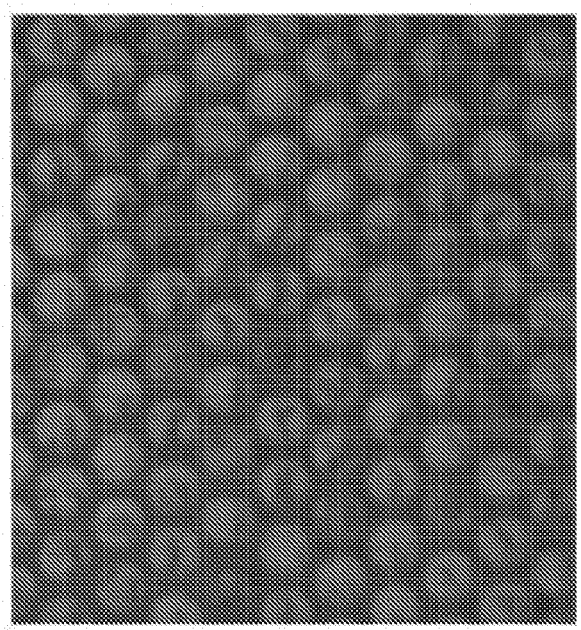
FIG. 10B shows the different fluorescent intensity levels that are detected or visualized by the presence or absence of cells. The microchannels of the substrate contain fluorescent material in the fluorescein isothiocyanate (FITC) channel. The relatively darkened regions indicate the presence of one or more cells in the microchannel of the substrate. The relatively bright regions indicate the absence of cells in the microchannel of the substrate.
Figure 10C:
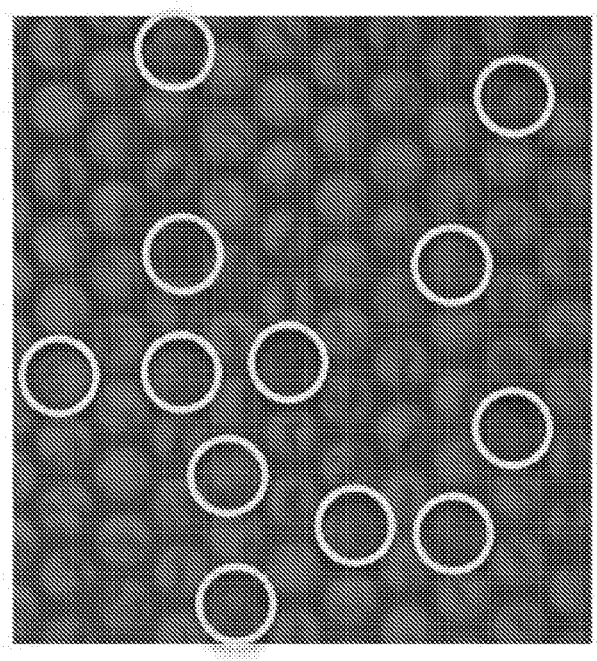
FIG. 10C shows the different fluorescent intensity levels that are detected or visualized by the presence or absence of cells. The microchannels of the substrate contain fluorescent material in the fluorescein isothiocyanate (FITC) channel. The relatively darkened regions indicate the presence of one or more cells in the microchannel of the substrate. The relatively bright regions indicate the absence of cells in the microchannel of the substrate. The regions containing cells are circled.
Figure 10D:
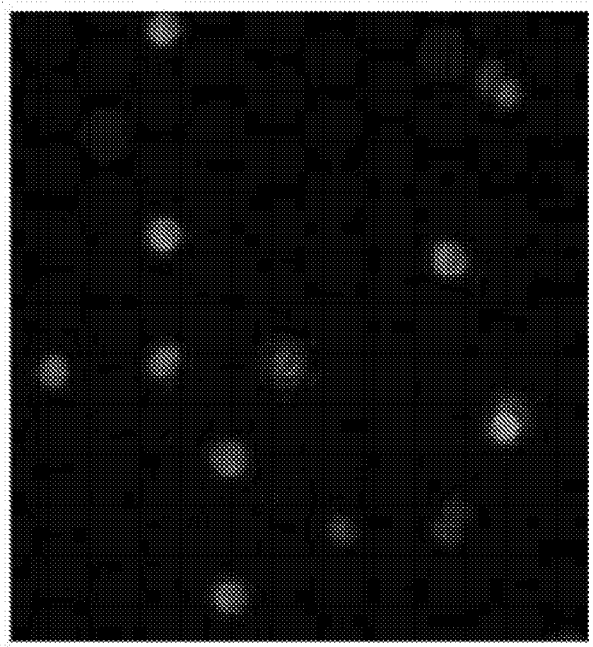
FIG. 10D identifies the regions that contain cells stained with cell tracker far red dye in the microchannel of the substrate. The microchannels containing the dye fluorescence correspond to relatively bright regions.
Figure 10E:
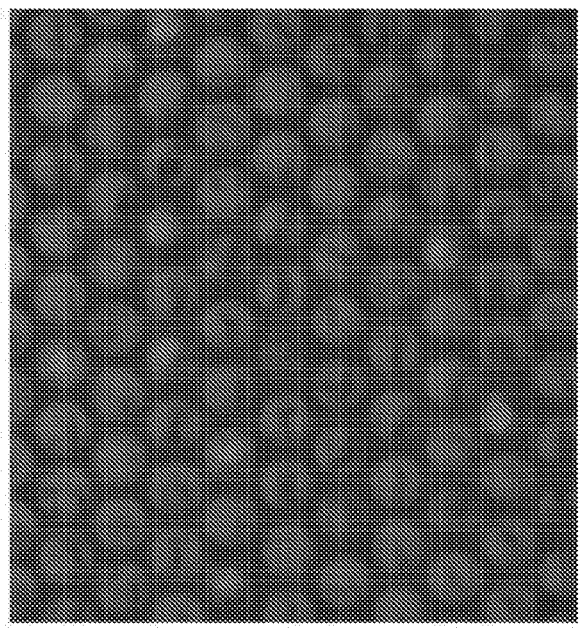
FIG. 10E identifies the regions that contain cells stained with the cell far red in the microchannel of the substrate. The microchannels containing cell tracker far red correspond to relatively bright regions. The remaining regions correspond to microchannels containing fluorescent material, but no cells.
Figure 10F:
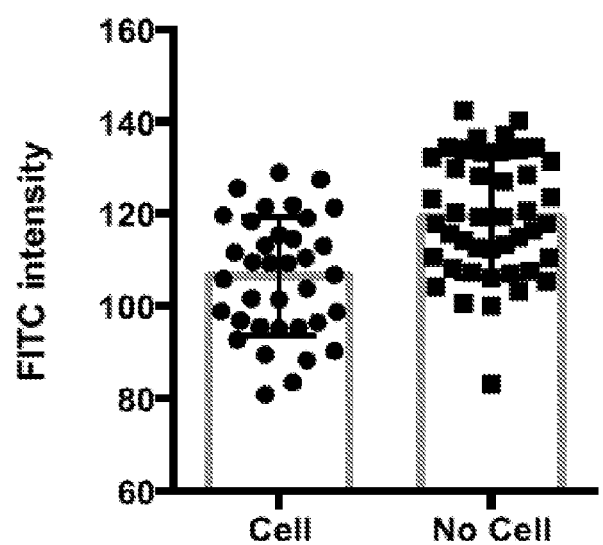
FIG. 10F is a graphical representation of fluorescent intensity in the presence of cells and absence of cells. The average fluorescent intensity was lower in the presence of a cell than in its absence.

In certain embodiments, the microchannels 610 of the substrate 130 are loaded with fluorescent material to enhance sample visibility. In an exemplary embodiment, as depicted in FIG. 10, sample material and fluorescent material are added to the microchannels, and later the sample material is quantified. In certain embodiments, sample material may comprise a cellular material. In certain embodiments, cellular material may comprise cells. Each microchannel of the substrate 130 is loaded near uniformly with fluorescent material. Fluorescent material may be in solution or attached to a solid, such as opaque beads. For example, fluorescent material may include fluorescein isothiocyanate, (FITC), Alexa Fluor®, Alexa Fluor® 594, Alexa Fluor® 647, Alexa Fluor® 700, Brilliant Violet™ 421, R-phycoerythrin (PE), PE-Cy® 5, allophycocyanin (APC), PE Texas Red®, green fluorescent protein (GFP), and yellow fluorescent protein (YFP). The presence of one or more cells lowers the fluorescent signal from the microchannel. The presence of a cell reduces the fluorescent intensity by at least 5% of the max value and no more than 95% of the max value. In this embodiment, high fluorescent intensity in the microchannel correlates with no cell count or a low cell count in the microchannel. Low fluorescent intensity correlates with a high cell count in the microchannel. For example, as seen in FIGS. 10C and 10D, the microchannels of the substrate that are loaded with fluorescent material and do not contain cells, those corresponding regions are brighter than the regions that contain cells. The regions that contain cells are circled in FIG. 10D. Additionally, FIGS. 10E and 10F show the regions that contain cells through the use of APC cells and its corresponding bright regions. FIG. 10G shows that the average fluorescent intensity of a microchannel with no cell is greater than the average fluorescent intensity of a microchannel with a cell.

Ultrafast Sorter

Figure 11:
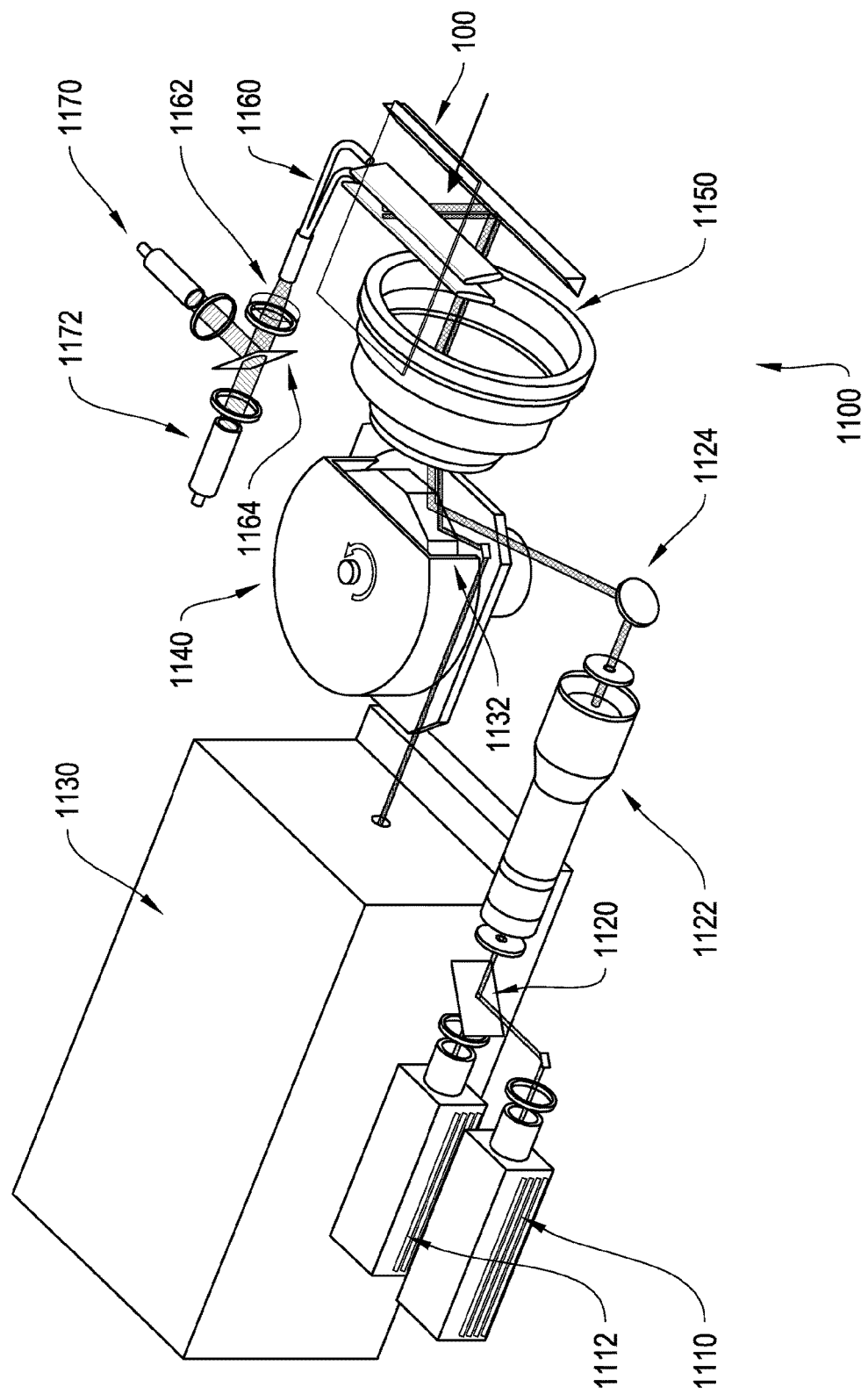
FIG. 11 is a schematic of an optical apparatus for laser scanning cell sorting utilizing a rotating polygon mirror.

In one embodiment of an optical apparatus for laser scanning cell sorting, FIG. 11 illustrates an optical apparatus utilizing a rotating polygon mirror. The apparatus 1100 comprises a first fluorescence excitation light source 1110 and a second fluorescence excitation light source 1112. In some cases, the apparatus may comprise a plurality of fluorescence excitation light sources. In some cases, the plurality of excitation light sources may overlap. In some cases, the plurality of excitation light sources may comprise 1, 2, 3, 4, 5, 6, 7, 8, 9, 10, 11, 12, or greater than 12 fluorescence excitation light sources. One or more of the plurality of fluorescence excitation light sources may comprise laser light sources. One or more of the excitation light sources may comprise light emitting diode (LED) light sources. In some cases, one or more of the plurality of fluorescence excitation light sources may emit light at a wavelength corresponding to the fluorescence excitation wavelength of a particular fluorophore. In some cases, one or more of the excitation light sources may be configured to emit a plurality of wavelengths of light. In some cases, one or more of the excitation light sources may be configured to emit a plurality of wavelengths of light, such that each of the plurality of wavelengths comprises a peak separated from others peaks of the plurality of wavelengths. One or more of the plurality of fluorescence excitation light sources may emit light at a wavelength corresponding to an excitation wavelength of a fluorophore that is endogenous to a cell to excite autofluorescence. For instance, one or more of the plurality of fluorescence excitation light sources may be tuned to the excitation wavelength of an autofluorescent molecule such as nicotinamide adenine dinucleotide phosphate (NADPH), chlorophyll, collagen, retinol, riboflavin, cholecalciferol, folic acid, pyridoxine, tyrosine, dityrosine, indolamine, lipofuscin, polyphenol, tryptophan, flavin, or melanin. One or more of the excitation light sources may emit light at a wavelength corresponding to an excitation wavelength of any autofluorescent molecule.

One or more of the plurality of fluorescence excitation light sources may emit light at a wavelength corresponding to an excitation wavelength of a fluorophore that is exogenous to a cell. For instance, one or more of the plurality of fluorescence excitation lights sources may be tuned to the excitation wavelength of hydroxycoumarin, methoxycoumarin, Alexa fluor, aminocoumarin, Cy2, carboxyfluorescein (FAM), Alexa fluor 488, fluorescein isothiocyanate (FITC), Alexa fluor 430, Alexa fluor 532, 6-carboxy-2,4,4, 5,7,7-hexachlorofluorescein (HEX), Cy3, tetramethylrhodamine (TRITC), Alexa fluor 546, Alexa fluor 555, R-phycoerythrin, Rhodamine Red-X, Tamara, Cy3.5 581, Rox, Alexa fluor 568, Red 613, Texas Red, Alexa fluor 594, Alexa fluor 633, allophycocyanin, Alexa fluor 647, Cy5, Alexa fluor 660, Cy5.5, TruRed, Alexa fluor 680, Cy7, or any other fluorophore as known to one having skill in the art.

Light from the fluorescence excitation light sources is directed to a dichroic mirror 1120 and passed to a beam expander 1122. In some cases, a plurality of dichroic mirrors are utilized to direct light from more than two excitation light sources to the beam expander. The apparatus may comprise 1, 2, 3, 4, 5, 6, 7, 8, 9, 10, 11, 12, or more than 12 dichroic mirrors. Upon expansion of the beams in the beam expander, light from the fluorescence excitation light sources is then directed to a mirror 1124. In some cases, the mirror 1124 comprises a galvanometer. The mirror directs the light to a rotating polygon mirror 1140. In some cases, the polygon mirror may be replaced by a resonant scanning mirror.

In certain embodiments, the polygon mirror may be substituted with a digital light processing system (DLPS). The DLPS may comprise a plurality of independently addressable micromirrors. The DLPS may be irradiated with a light source. Each of the plurality of micromirrors may be independently positioned to either direct light to a particular location or to prevent light from reaching a particular location. Each micromirror may be addressed electronically.

The rotating polygon mirror rapidly scans light from the fluorescence excitation light sources along a curved focal plane perpendicular to the axis of rotation of the polygon mirror. An F-theta lens 1150 produces a focal plane that is substantially flat. After reflection from a surface of the rotating polygon mirror and refraction through the F-theta lens, light from the excitation light sources is directed to the cassette 100. The F-theta lens may be configured to focus the plurality of excitation beams to a microchannel in the cassette. As the rotating polygon mirror rotates, light from the excitation light sources is scanned across a line of microchannels in the cassette. After a scan across a single line, the cassette may be moved to allow scanning of a new line. In some cases, the movement is timed to the scanning of a single line. The timing may be accomplished, for instance, by coordinating the movement of the cassette and the scanning of light through a synchronized clock signal.

Upon receiving light from the excitation light sources, one or more cells in a microchannel may fluoresce and emit light of a greater wavelength than the wavelength of the excitation light source that stimulated the fluorescence. The fluorescence may be due to the presence of endogenous fluorophores located within or on the cell. The fluorescence may be due to the presence of exogenous fluorophores. The emitted light is received and guided by a light guide 1160. The light guide may comprise an optical fiber. The light guide may comprise an optical fiber bundle. The light guide may comprise one or more mirrors. The one or more mirrors may comprise flat mirrors. The one or more mirrors may comprise flat dichroic mirrors. The one or more mirrors may comprise concave mirrors. The one or more mirrors may comprise spherical mirrors. The emitted light is directed to a set of coupling optics 1162 and to a beamsplitter 1164. The beamsplitter allows one wavelength of emitted light to pass to a first detector 1172 and redirects another wavelength of emitted light to a second detector 1174. In some cases, the apparatus may comprise a plurality of beamsplitters. In some cases, the apparatus may comprise a plurality of detectors. In some cases, the plurality of beamsplitters may comprise 1, 2, 3, 4, 5, 6, 7, 8, 9, 10, 11, 12, or greater than 12 beamsplitters. In some cases, the plurality of detectors may comprise 1, 2, 3, 4, 5, 6, 7, 8, 9, 10, 11, 12, or greater than 12 detectors. Each beamsplitter of the plurality of beamsplitters may allow one or more wavelengths of emitted light to pass and may redirect other wavelengths of emitted light. Each detector of the plurality of detectors may be a photodiode, a photomultiplier tube, or any other optical detector as known to one having skill in the art.

Each detector registers a signal corresponding to the intensity of emitted light having a particular wavelength. The light intensity at each detector is electronically sampled, digitized, and directed to electronic circuitry (not shown). The electronic circuitry processes the signals from each detector in order to make a determination as to whether a particular microchannel contains a cell that should be removed from the microchannel. In some cases, the electronic circuitry acts to determine whether the intensities of emitted light detected by each of the plurality of detectors exceeds a threshold value. In some cases, the electronic circuitry acts to determine whether the intensities of emitted light detected by each of the plurality of detectors falls within a range of values. In some cases, the range of values may be different for each detector. If the intensities of emitted light detected by each of the plurality of detectors lies within the range of values, the electronic circuitry sends a signal to remove the corresponding cell from the given microchannel. In some cases, the circuitry is implemented as firmware. In some cases, the circuitry is implemented as a field programmable gate array (FPGA).

In some instances, the range of values for each detector may be unknown at the outset of the scanning procedure. For instance, the range of values may depend on the cell type (e.g. red blood cell, white blood cell, etc). The range of values may depend on operating parameters of the system (e.g. age-related degradation of optical components). Thus, it may be beneficial to determine acceptable ranges of values upon receiving a new cassette in the system. For instance, such ranges may be determined by scanning the plurality of excitation light sources over a sample population of cells and determining the intensities at each detector for the population of cells. The population of cells may comprise more than 1,000, more than 10,000, more than 100,000, or more than 1,000,000 cells. The population of cells may lie in a range defined by any two of the preceding values. The range of values may be chosen such that only a subpopulation of the cells from the sample population gives rise to fluorescence intensities falling within the range of values. For instance, the range of values for each detector may be chosen such that less than 1%, less than 5%, less than 10%, less than 20%, or less than 50% of the cells give rise to fluorescence intensities at each detector that fall within the range of values. The range of values may be chosen to lie within a range defined by any two of the preceding values. These ranges of values may then be used to determine whether a given cell should be removed from a given microchannel during a scan of the entire cassette.

When the electronic circuitry makes a determination that a given cell in a given microchannel meets the criteria for removal from the microchannel, a signal may be sent to direct light from an extraction laser source 1130 to the microchannel. In some cases, the extraction laser and the circuitry may be synchronized to a shared clock. The extraction laser source may emit light at a wavelength that allows extraction of a cell from a microchannel. For instance, the extraction laser source may emit light at a wavelength that is absorbed by a particle in a microchannel, as described herein. The extraction laser source may emit light at a wavelength in the ultraviolet, visible, or near infrared region of the electromagnetic spectrum. The extraction laser source may emit light in a range of wavelengths from about 200 nm to about 2000 nm. The extraction laser source may comprise a continuous wave laser source. The extraction source may comprise a quasi-continuous wave laser source. The extraction laser source may comprise a pulsed laser source. The pulsed laser source may emit laser pulses having a duration shorter than 10 fs, shorter than 100 fs, shorter than 1 ps, shorter than 10 ps, shorter than 100 ps, shorter than 1 ns, shorter than 10 ns, shorter than 100 ns, shorter than 1 µs, shorter than 10 µs, shorter than 100 µs, or shorter than 1 ms. The pulsed laser source may emit laser pulses having a duration lying in a range defined by any two of the preceding values. In some cases, the pulsed laser source may emit laser pulses having a duration within the range from about 1 fs to about 100 µs. In some cases, the pulsed laser source may emit laser pulses having a duration within the range from about 100 ns to about 10 µs. The pulsed laser source may emit laser pulses having an adjustable duration.

The pulsed laser source may emit laser pulses with a repetition rate of less than 1 kHz, less than 10 kHz, less than 100 kHz, less than 1 MHz, less than 10 MHz, less than 100 MHz, or less than 1 GHz. The pulsed laser source may emit laser pulses with a repetition rate lying in a range defined by any two of the preceding values. In some cases, the pulsed laser source may emit pulses with a repetition rate within the range from about 10 KHz to about 1 MHz. In some cases, each pulse may produce less than 1 nJ, less than 10 nJ, less than 100 nJ, less than 1 µJ, less than 10 µJ, less than 100 µJ, or less than 1 mJ of energy. Each pulse may produce an energy lying in a range defined by any two of the preceding values. In some cases, each pulse may produce an energy lying in the range from about 1 µJ to about 50 µJ. The pulsed laser source may emit a peak power in the range from 0.1 W to $10^7$ W.

The pulsed laser source may be a fiber laser source. The pulsed laser source may be a pulse-on-demand fiber laser source. The pulsed laser source may be a master oscillator fiber amplifier (MOPA) laser source. The pulsed laser source may be a doped fiber laser source. The pulsed laser source may be a rare earth ion doped fiber laser source. The pulsed laser source may be a ytterbium doped fiber laser source. The pulsed laser source may be a laser utilizing a doped crystal gain medium. The pulsed laser source may be a laser utilizing a neodymium-doped crystal gain medium. The pulsed laser source may be a Nd:YAG laser. The pulsed laser source may be a Nd:YVO$_4$ laser. The pulsed laser source may be a semiconductor laser. The pulsed laser source may be a diode laser. The pulsed laser source may be a vertical cavity surface emitting laser (VCSEL). The pulsed laser source may be a VCSEL array. The pulsed laser source may be a gas laser. The pulsed laser source may be a CO$_2$ laser. The pulsed laser source may be an excimer laser. The pulsed laser source may employ Q-switching. The pulsed laser source may employ mode locking. The pulsed laser source may be any pulsed laser source as is known to one having skill in the art.

The pulsed laser source may direct a laser pulse to a microchannel in response to a signal from electronic circuitry in response to intensities of light detector at each of the plurality of detectors. The pulse may be directed to the microchannel using an acousto-optical modulator (AOM), electro-optic modular (EOM), or any modulation device as may be known to one having skill in the art. For instance, the modulation device may be configured to pass the zero-order diffracted beam only in response to a signal that the extraction laser should remove a cell from a microchannel; at all other times, the modulation device may be configured to pass the first-order diffracted beam or higher-order diffracted beam. In some cases, the pulsed laser may produce pulses only in response to a signal that the extraction laser should remove a cell from a microchannel. For instance, a doped fiber laser may be operated in a reverse-biased configuration until receiving a signal to direct a pulse to the microchannel; upon receiving the signal to direct a pulse to the microchannel, the doped fiber laser may be operated in the forward-biased configuration.

The extraction laser may be directed to the rotating polygon mirror by a mirror 1132. The rotating polygon mirror rapidly scans light from the extraction laser along a curved focal plane perpendicular to the axis of rotation of the polygon mirror. The F-theta lens produces a focal plane that is substantially flat. After reflection from a surface of the rotating polygon mirror and refraction through the F-theta lens, light from the extraction laser is directed to the cassette 100. The F-theta lens may be configured to focus the plurality of excitation beams to a microchannel in the cassette. When the extraction laser is directed to a microchannel, energy from the laser causes cavitation of the liquid sample in which a cell is suspended. This causes the removal of the cell from the microchannel.

The system may be configured to scan both the plurality of fluorescence excitation beams and the extraction beam. In some cases, the system may be configured to scan the extraction beam so that it is separated from the plurality of fluorescence excitation beams. In some cases, the system may be configured to focus the plurality of excitation light sources on a first microchannel and to simultaneously focus the extraction laser on a second microchannel. In some cases, the extraction beam may be separated from the plurality of fluorescence excitation beams by a distance of less than 1 μm, 5 μm, 10 μm, less than 50 μm, less than 100 μm, less than 500 μm, less than 1 mm, less than 5 mm, or less than 10 mm. In some cases, the extraction beam may be separated from the plurality of fluorescence excitation beams by a distance lying in a range defined by any two of the preceding values. In some cases, the extraction beam may be separated from the plurality of fluorescence excitations beams by a distance within a range from about 100 μm to about 5 mm. In some cases, the extraction beam may be separated from the plurality of fluorescence excitations beams by a distance within a range from about 100 μm to about 1 mm. In some cases, the extraction beam may be separated from the plurality of fluorescence excitations beams by a distance within a range from about 10 μm to about 1000 mm. The plurality of excitation light sources and the extraction beam may be located on the same side of the cassette. The plurality of excitation light sources and the extraction beam may be located on opposite sides of the cassette.

In some cases, the system may be configured to scan the microchannels at a rate of more than 10,000 channels per second, more than 50,000 channels per second, more than 100,000 channels per second, more than 500,000 channels per second, more than 1,000,000 channels per second, more than 5,000,000 channels per second, more than 10,000,000 channels per second, more than 50,000,000 channels per second, or more than 100,000,000 channels per second. The system may be configured to scan the microchannels at a rate lying in a range defined by any two of the preceding values. In some cases, the system may be configured to scan the microchannels at a rate within a range from about 3,000 to about 300,000,000 channels per second.

System 1100 may scan the substrate at a rate greater than 1,000,000 microchannels per second, greater than 2,000,000 microchannels per second, or greater than 3,000,000 microchannels per second. System 1100 may scan the substrate at a rate that is within a range defined by any two of the preceding values. System 1100 may extract target particles from the substrate at a rate greater than 500,000 microchannels per second, greater than 600,000 microchannels per second, greater than 700,000 microchannels per second, greater than 800,000 microchannels per second, greater than 900,000 microchannels per second, or greater than 1,000,000 microchannels per second. System 1100 may extract target particles at a rate that is within a range defined by any two of the preceding values. System 1100 may extract the target particles such that a collection of extracted target particles has a purity greater than 90%, greater than 95%, or greater than 99%. System 1100 may extract the target particles such that the collection of extracted target particles has a purity that is within a range defined by any two of the preceding values.

Though shown as forming a single device in FIG. 11, system 1100 may be configured such that the fluorescence subsystem (comprising elements 1110, 1112, 1120, 1122, 1124, 1140, 1150, 1160, 1162, 1164, 1170, and 1172) are arranged as a fluorescence device and the extraction subsystem (comprising elements 1130, 1132, 1140, and 1150) are arranged as an extraction device. In such an arrangement, the substrate 100 may be subjected to a fluorescence analysis as described herein using the fluorescence device. Following the fluorescence analysis, the substrate may be transferred to the extraction device for extraction of locations of interest on the substrate identified during the fluorescence analysis. Proper alignment of the substrate in each of the fluorescence device and the extraction device may be achieved by referring to one or more fiducial markers on the substrate. In some cases, arranging system 1100 on two devices may require duplication of one or more elements of system 1100. For instance, elements 1140 and 1150 may be required on both the fluorescence device and the extraction device.

Figure 12:
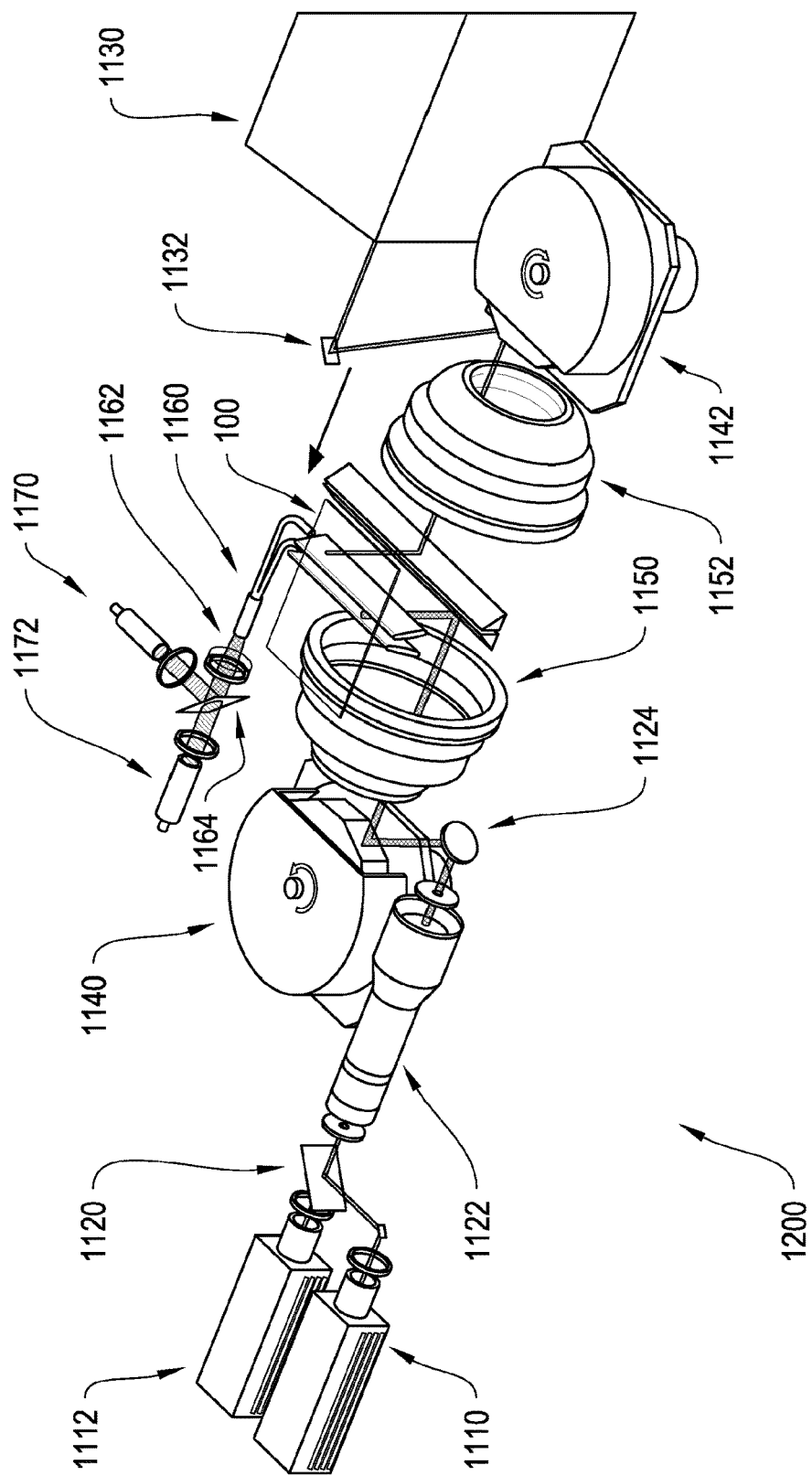
FIG. 12 is a schematic of an optical apparatus for laser scanning cell sorting utilizing two rotating polygon mirrors.

In another embodiment of an optical apparatus for laser scanning cell sorting, FIG. 12 illustrates an optical apparatus utilizing two rotating polygon mirrors. The apparatus 1200 comprises all of the elements of apparatus 1100 from FIG. 11. The apparatus comprises: a plurality of excitation light sources 1110 and 1112, a dichroic mirror 1120, a beam expander 1122, an excitation light mirror 1124, an extraction laser 1130, an extraction laser mirror 1132, a rotating polygon mirror 1140, an F-theta lens 1150, a light guide 1160, coupling optics 1162, a plurality of beamsplitters 1164, and a plurality of detectors 1170 and 1172.

Additionally, the apparatus 1200 comprises a second rotating polygon mirror 1142 and a second F-theta lens 1152. In some cases, the second polygon mirror may be replaced by a resonant scanning mirror. The system may be configured such that the plurality of excitation light sources are directed to the cassette 100 by the first rotating polygon mirror 1140 and the first F-theta lens 1150, while the extraction laser is directed to the cassette by the second rotating polygon mirror 1142 and the second F-theta lens 1152. The plurality of excitation light sources and the extraction beam may be located on the same side of the cassette. The plurality of excitation light sources and the extraction beam may be located on opposite sides of the cassette.

The first rotating polygon mirror rapidly scans light from the fluorescence excitation light sources along a curved focal plane perpendicular to the axis of rotation of the polygon mirror. The first F-theta lens produces a focal plane that is substantially flat. After reflection from a surface of the first rotating polygon mirror and refraction through the first F-theta lens, light from the excitation light sources is directed to the cassette 100. The first F-theta lens may be configured to focus the plurality of excitation beams to a microchannel in the cassette. As the first rotating polygon mirror rotates, light from the excitation light sources is scanned across a line of microchannels in the cassette.

The second rotating polygon mirror rapidly scans light from the excitation laser along a curved focal plane perpendicular to the axis of rotation of the polygon mirror. The second F-theta lens produces a focal plane that is substantially flat. After reflection from a surface of the second rotating polygon mirror and refraction through the second F-theta lens, light from the extraction laser is directed to the cassette 100. The second F-theta lens may be configured to focus the extraction laser to a microchannel in the cassette. As the second rotating polygon mirror rotates, light from the extraction laser is scanned across a line of microchannels in the cassette.

The system may be configured to scan both the plurality of fluorescence excitation beams, using the first rotating polygon mirror, and the extraction beam, using the second rotating polygon mirror. In some cases, the system may be configured to scan the extraction beam so that it is separated from the plurality of fluorescence excitation beams. In some cases, the system may be configured to focus the plurality of excitation light sources on a first microchannel and to simultaneously focus the extraction laser on a second microchannel. In some cases, the extraction beam may be separated from the plurality of fluorescence excitation beams by a distance of less than 1 µm, 5 µm, 10 µm, less than 50 µm, less than 100 µm, less than 500 µm, less than 1 mm, less than 5 mm, or less than 10 mm. In some cases, the extraction beam may be separated from the plurality of fluorescence excitation beams by a distance lying in a range defined by any two of the preceding values. In some cases, the extraction beam may be separated from the plurality of fluorescence excitations beams by a distance within a range from about 100 µm to about 5 mm. In some cases, the extraction beam may be separated from the plurality of fluorescence excitations beams by a distance within a range from about 100 µm to about 1 mm. In some cases, the extraction beam may be separated from the plurality of fluorescence excitations beams by a distance within a range from about 10 µm to about 1000 mm. In some cases, the scanning of the plurality of excitation light sources and the excitation laser is synchronized. In some cases, the synchronization is achieved through a synchronized clock signal. The plurality of excitation light sources and the extraction beam may be located on the same side of the cassette. The plurality of excitation light sources and the extraction beam may be located on opposite sides of the cassette.

In some cases, the system may be configured to scan the microchannels at a rate of more than 10,000 channels per second, more than 50,000 channels per second, more than 100,000 channels per second, more than 500,000 channels per second, more than 1,000,000 channels per second, more than 5,000,000 channels per second, more than 10,000,000 channels per second, more than 50,000,000 channels per second, or more than 100,000,000 channels per second. The system may be configured to scan the microchannels at a rate lying in a range defined by any two of the preceding values. In some cases, the system may be configured to scan the microchannels at a rate within a range from about 3,000 to about 300,000,000 channels per second.

System 1200 may scan the substrate at a rate greater than 1,000,000 microchannels per second, greater than 2,000,000 microchannels per second, or greater than 3,000,000 microchannels per second. System 1200 may scan the substrate at a rate that is within a range defined by any two of the preceding values. System 1200 may extract target particles from the substrate at a rate greater than 500,000 microchannels per second, greater than 600,000 microchannels per second, greater than 700,000 microchannels per second, greater than 800,000 microchannels per second, greater than 900,000 microchannels per second, or greater than 1,000,000 microchannels per second. System 1200 may extract target particles at a rate that is within a range defined by any two of the preceding values. System 1200 may extract the target particles such that a collection of extracted target particles has a purity greater than 90%, greater than 95%, or greater than 99%. System 1200 may extract the target particles such that the collection of extracted target particles has a purity that is within a range defined by any two of the preceding values.

Though shown as forming a single device in FIG. 12, system 1200 may be configured such that the fluorescence subsystem (comprising elements 1110, 1112, 1120, 1122, 1124, 1140, 1150, 1160, 1162, 1164, 1170, and 1172) are arranged as a fluorescence device and the extraction subsystem (comprising elements 1130, 1132, 1142, and 1152) are arranged as an extraction device. In such an arrangement, the substrate 100 may be subjected to a fluorescence analysis as described herein using the fluorescence device. Following the fluorescence analysis, the substrate may be transferred to the extraction device for extraction of locations of interest on the substrate identified during the fluorescence analysis. Proper alignment of the substrate in each of the fluorescence device and the extraction device may be achieved by referring to one or more fiducial markers on the substrate.

Figure 13:
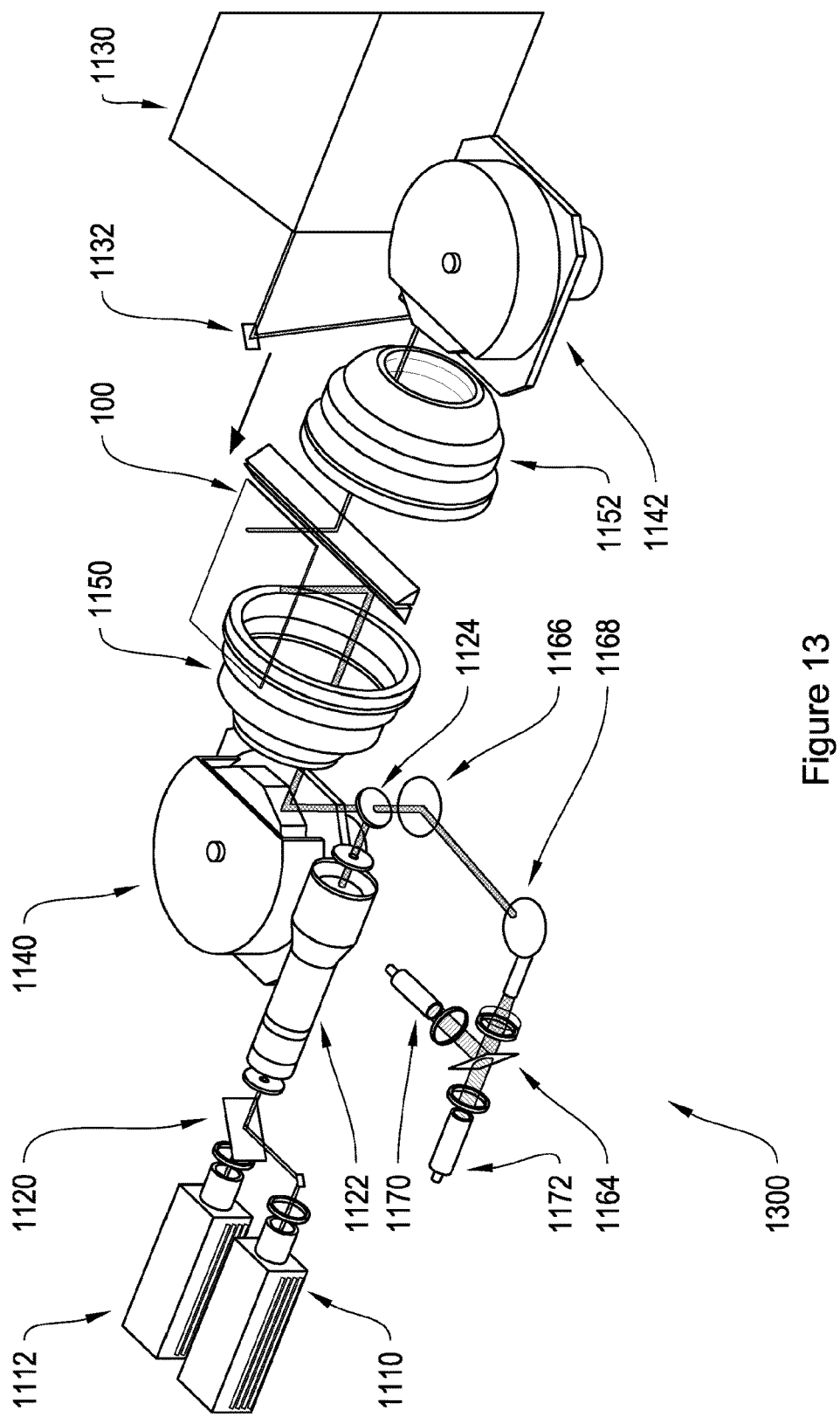
FIG. 13 is a schematic of an optical apparatus for laser scanning cell sorting utilizing two rotating polygon mirrors and a confocal detection technique.

In another embodiment of an optical apparatus for laser scanning cell sorting, FIG. 13 illustrates an optical apparatus utilizing two rotating polygon mirrors and a confocal detection technique. The apparatus 1300 comprises many of the elements of apparatus 1100 from FIG. 11. The apparatus comprises: a plurality of excitation light sources 1110 and 1112, a dichroic mirror 1120, a beam expander 1122, an excitation light mirror 1124, an extraction laser 1130, an extraction laser mirror 1132, a rotating polygon mirror 1140, an F-theta lens 1150, coupling optics 1162, a plurality of beamsplitters 1164, and a plurality of detectors 1170 and 1172.

Additionally, the apparatus 1300 may comprise a second rotating polygon mirror 1142 and a second F-theta lens 1152. The system may be configured such that the plurality of excitation light sources are directed to the cassette 100 by the first rotating polygon mirror 1140 and the first F-theta lens 1150, while the extraction laser is directed to the cassette by the second rotating polygon mirror 1142 and the second F-theta lens 1152. The plurality of excitation light sources and the extraction beam may be located on the same side of the cassette. The plurality of excitation light sources and the extraction beam may be located on opposite sides of the cassette.

In place of the light guide, the apparatus 1300 further comprises a set of mirrors to direct light to the one or more detectors. The excitation light mirror 1124 may be a dichroic mirror. The confocal detection cavity may comprise mirrors 1166 and 1168. The mirrors may be flat mirrors. The mirrors may be concave mirrors. The mirrors may be spherical mirrors. The mirrors may be arranged in a confocal configuration.

System 1300 may scan the substrate at a rate greater than 1,000,000 microchannels per second, greater than 2,000,000 microchannels per second, or greater than 3,000,000 microchannels per second. System 1300 may scan the substrate at a rate that is within a range defined by any two of the preceding values. System 1300 may extract target particles from the substrate at a rate greater than 500,000 microchannels per second, greater than 600,000 microchannels per second, greater than 700,000 microchannels per second, greater than 800,000 microchannels per second, greater than 900,000 microchannels per second, or greater than 1,000,000 microchannels per second. System 1300 may extract target particles at a rate that is within a range defined by any two of the preceding values. System 1300 may extract the target particles such that a collection of extracted target particles has a purity greater than 90%, greater than 95%, or greater than 99%. System 1300 may extract the target particles such that the collection of extracted target particles has a purity that is within a range defined by any two of the preceding values.

Though shown as forming a single device in FIG. 13, system 1300 may be configured such that the fluorescence subsystem (comprising elements 1110, 1112, 1120, 1122, 1124, 1140, 1150, 1164, 1166, 1168, 1170, and 1172) are arranged as a fluorescence device and the extraction subsystem (comprising elements 1130, 1132, 1142, and 1152) are arranged as an extraction device. In such an arrangement, the substrate 100 may be subjected to a fluorescence analysis as described herein using the fluorescence device. Following the fluorescence analysis, the substrate may be transferred to the extraction device for extraction of locations of interest on the substrate identified during the fluorescence analysis. Proper alignment of the substrate in each of the fluorescence device and the extraction device may be achieved by referring to one or more fiducial markers on the substrate.

Figure 14:
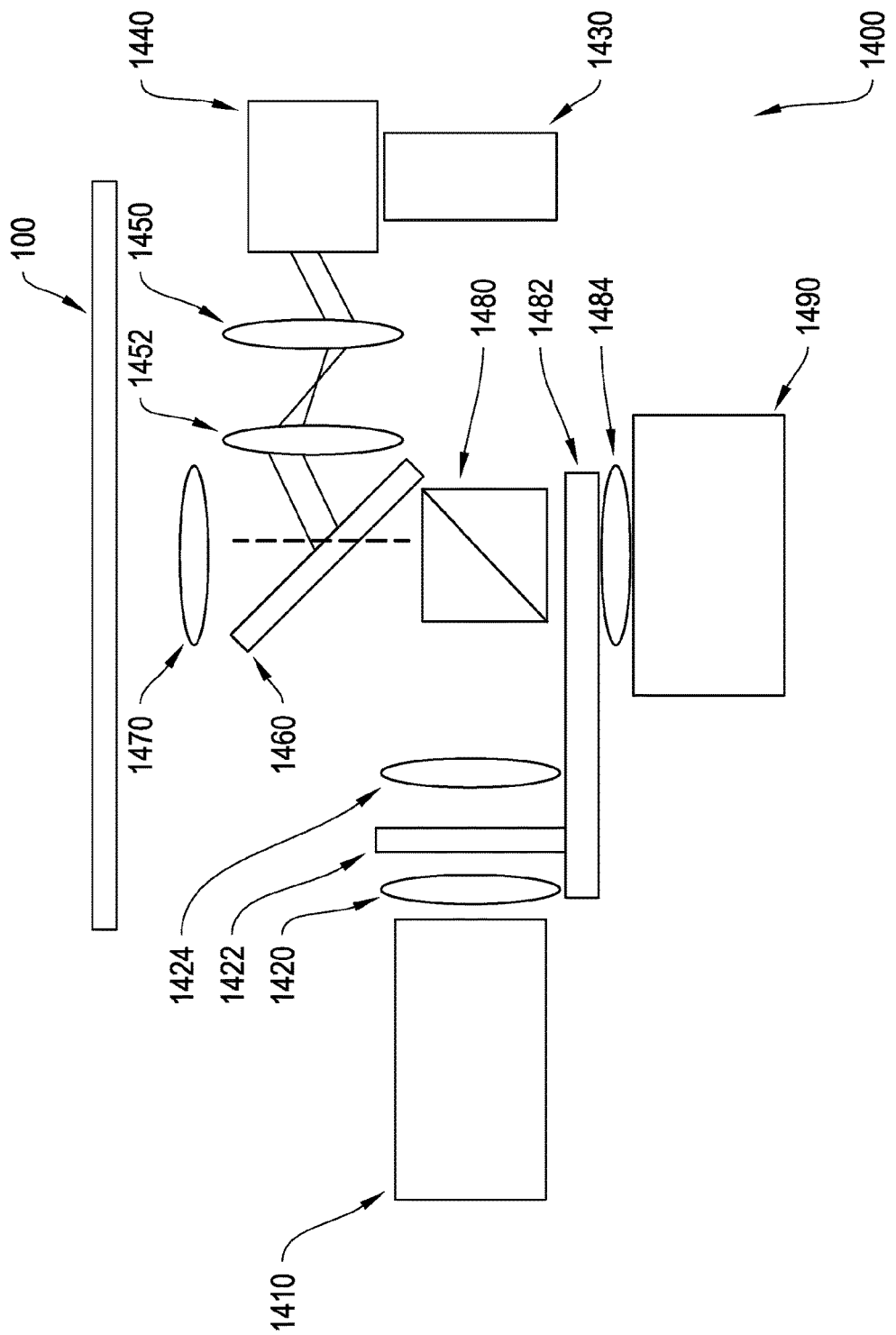
FIG. 14 is a schematic of an optical apparatus for laser scanning cell sorting utilizing a galvanometer scanning mechanism.

In another embodiment of an optical apparatus for laser scanning cell sorting, FIG. 14 illustrates an optical apparatus utilizing a galvanometer scanning mechanism. The apparatus 1400 comprises a fluorescence excitation light source 1410. In some cases, the apparatus may comprise a plurality of fluorescence excitation light sources. In some cases, the plurality of excitation light sources may overlap. In some cases, the plurality of excitation light sources may comprise 1, 2, 3, 4, 5, 6, 7, 8, 9, 10, 11, 12, or greater than 12 fluorescence excitation light sources. One or more of the plurality of fluorescence excitation light sources may comprise laser light sources. One or more of the excitation light sources may comprise light emitting diode (LED) light sources. In some cases, one or more of the plurality of fluorescence excitation light sources may emit light at a wavelength corresponding to the fluorescence excitation wavelength of a particular fluorophore. In some cases, one or more of the excitation light sources may be configured to emit a plurality of wavelengths of light. In some cases, one or more of the excitation light sources may be configured to emit a plurality of wavelengths of light, such that each of the plurality of wavelengths comprises a peak separated from others peaks of the plurality of wavelengths. One or more of the plurality of fluorescence excitation light sources may emit light at a wavelength corresponding to an excitation wavelength of a fluorophore that is endogenous to a cell to excite autofluorescence. For instance, one or more of the plurality of fluorescence excitation light sources may be tuned to the excitation wavelength of an autofluorescent molecule such as nicotinamide adenine dinucleotide phosphate (NADPH), chlorophyll, collagen, retinol, riboflavin, cholecalciferol, folic acid, pyridoxine, tyrosine, dityrosine, indolamine, lipofuscin, polyphenol, tryptophan, flavin, or melanin. One or more of the excitation light sources may emit light at a wavelength corresponding to an excitation wavelength of any autofluorescent molecule.

One or more of the plurality of fluorescence excitation light sources may emit light at a wavelength corresponding to an excitation wavelength of a fluorophore that is exogenous to a cell. For instance, one or more of the plurality of fluorescence excitation lights sources may be tuned to the excitation wavelength of hydroxycoumarin, methoxycoumarin, Alexa fluor, aminocoumarin, Cy2, carboxyfluorescein (FAM), Alexa fluor 488, fluorescein isothiocyanate (FITC), Alexa fluor 430, Alex fluor 532, 6-carboxy-2,4,4,5, 7,7-hexachlorofluorescein (HEX), Cy3, tetramethylrhodamine (TRITC), Alexa fluor 546, Alexa fluor 555, R-phycoerythrin, Rhodamine Red-X, Tamara, Cy3.5 581, Rox, Alexa fluor 568, Red 613, Texas Red, Alexa fluor 594, Alexa fluor 633, allophycocyanin, Alexa fluor 647, Cy5, Alexa fluor 660, Cy5.5, TruRed, Alexa fluor 680, Cy7, or any other fluorophore as known to one having skill in the art.

Light from the fluorescence excitation light sources is directed to a set of conditioning optics. The conditioning optics may comprise a first lens 1420 and a second lens 1424. The two lenses may act to expand the beamwaist of the excitation light, reduce the beamwaist of the excitation light, and/or to collimate the excitation light. The conditioning optics may further comprise a filter wheel 1422.

The excitation light is then passed to a dichroic mirror 1480. In some cases, a plurality of dichroic mirrors are utilized to direct light from more than two excitation light sources to the beam expander. The apparatus may comprise 1, 2, 3, 4, 5, 6, 7, 8, 9, 10, 11, 12, or more than 12 dichroic mirrors. In some cases, the apparatus may comprise a multi-edge dichroic cube.

The excitation light is directed to a dichroic mirror 1460. The dichroic mirror 1460 may be a dichroic mirror configured to pass light having a wavelength in the ultraviolet or visible region of the electromagnetic spectrum and to reflect light having a wavelength in the infrared region of the electromagnetic spectrum. The excitation light is directed to an objective lens 1470. The objective lens may have a magnification greater than 1×, 2×, 5×, 10×, 20×, 50×, 100×, 200×, 500×, 1000×. The objective lens may have a magnification in a range defined by any two of the preceding values. The objective lens may be an infinity corrected objective lens. The objective lens provides a large excitation field and a large field-of-view. This allows the excitation light source to illuminate a large area of the cassette 100 without requiring scanning of the excitation light sources. In some cases, the apparatus may comprise a plurality of objective lenses having a plurality of fields-of-view.

In some cases, the apparatus is configured to transmit the excitation light coaxially with the field-of-view through the objective lens. In some cases, the excitation light comprises diffused excitation light. In some cases, the excitation light comprises diffused infinity corrected excitation light. The excitation light may excite fluorescence over an excitation field of less than 1 mm, less than 5 mm, less than 10 mm, less than 50 mm, or less than 100 mm. The excitation light may excite fluorescence over an excitation field lying in a range defined by any two of the preceding values. The objective lens may have a field-of-view of less than 1 mm, less than 5 mm, less than 10 mm, less than 50 mm, or less than 100 mm. The objective lens may have a field-of-view lying in a range defined by any two of the preceding values. In some cases, the field-of-view is defined with an optical structure. The optical structure may be an aperture. The optical structure may be a dimension across an aperture. The optical structure may be a pinhole. The optical structure may be a mirror. The optical structure may be a dimension across a reflective surface of a mirror.

Upon receiving light from the excitation light sources, one or more cells in a microchannel may fluoresce and emit light of a greater wavelength than the wavelength of the excitation light source that stimulated the fluorescence. The fluorescence may be due to the presence of endogenous fluorophores located within or on the cell. The fluorescence may be due to the presence of exogenous fluorophores. The emitted light is directed to a wavelength selector 1482 to select desired wavelengths of light. In some cases, the wavelength selector produces filtered light. The filtered light is directed to a two-dimensional array detector 1490 using a lens 1484. In some cases, the two-dimensional array detector comprises a camera. In some cases, the lens 1484 comprises a tube lens. The camera produces a fluorescence image of cells that are located within its field-of-view.

The wavelength selector may comprise a filter. The filter may comprise an emission filter. The filter may comprise an emission filter wheel. The emission filter wheel may comprise a plurality of filters. In some cases, the apparatus may comprise a plurality of wavelength-selective filters. The wavelength selector may comprise a dichroic mirror. The wavelength selector may comprise a prism. The wavelength selector may comprise a diffraction grating. The apparatus may comprise 1, 2, 3, 4, 5, 6, 7, 8, 9, 10, 11, 12, or greater than 12 wavelength selectors. In some cases, the apparatus may comprise a plurality of cameras. The apparatus may comprise 1, 2, 3, 4, 5, 6, 7, 8, 9, 10, 11, 12, or greater than 12 cameras. Each filter of the plurality of wavelength selectors may allow one or more wavelengths of emitted light to pass to one or more of the plurality of cameras and may redirect or absorb other wavelengths of emitted light. Each camera of the plurality of cameras may be a charge-coupled device (CCD) camera, a complementary metal oxide semiconductor (CMOS) camera, or any other camera as known to one having skill in the art.

Each camera registers an image corresponding to the intensity of emitted light having a particular wavelength. The light intensity at each camera is electronically sampled, digitized, and directed to electronic circuity (not shown). The electronic circuitry processes the signals from each camera in order to make a determination as to whether a particular microchannel contains a cell that should be removed from the microchannel. In some cases, the electronic circuitry acts to determine whether the intensities of emitted light at each pixel detected by each of the plurality of cameras exceeds a threshold value. In some cases, the electronic circuitry acts to determine whether the intensities of emitted light at each pixel detected by each of the plurality of cameras falls within a range of values. In some cases, the range of values may be different for each camera. If the intensities of emitted light detected by each of the plurality of cameras lies within the range of values for a given pixel, the electronic circuitry sends a signal to remove the corresponding cell from the given microchannel. In some cases, the circuitry is implemented as firmware. In some cases, the circuitry is implemented as a field programmable gate array (FPGA).

In some instances, the range of values for each detector may be unknown at the outset of the scanning procedure. For instance, the range of values may depend on the cell type (e.g. red blood cell, white blood cell, etc). The range of values may depend on operating parameters of the system (e.g. age-related degradation of optical components). Thus, it may be beneficial to determine acceptable ranges of values upon receiving a new cassette in the system. For instance, such ranges may be determined by scanning the plurality of excitation light sources over a sample population of cells and determining the intensities at each pixel of each camera for the population of cells. The population of cells may comprise more than 1,000, more than 10,000, more than 100,000, or more than 1,000,000 cells. The population of cells may lie in a range defined by any two of the preceding values. The range of values may be chosen such that only a subpopulation of the cells from the sample population gives rise to fluorescence intensities falling within the range of values. For instance, the range of values for each pixel of each camera may be chosen such that less than 1%, less than 5%, less than 10%, less than 20%, or less than 50% of the cells give rise to fluorescence intensities at each pixel at each camera that fall within the range of values. The range of values may be chosen to lie within a range defined by any two of the preceding values. These ranges of values may then be used to determine whether a given cell should be removed from a given microchannel during a scan of the entire cassette.

When the electronic circuitry makes a determination that a given cell in a given microchannel meets the criteria for removal from the microchannel, a signal may be sent to direct light from an extraction laser source 1430 to the microchannel. In some cases, the extraction laser and the circuitry may be synchronized to a shared clock. The extraction laser source may emit light at a wavelength that allows extraction of a cell from a microchannel. For instance, the extraction laser source may emit light at a wavelength that is absorbed by a particle in a microchannel, as described herein. The extraction laser source may emit light at a wavelength in the ultraviolet, visible, or near infrared region of the electromagnetic spectrum. The extraction laser source may emit light in a range of wavelengths from about 200 nm to about 2000 nm. The extraction laser source may comprise a continuous wave laser source. The extraction source may comprise a quasi-continuous wave laser source. The extraction laser source may comprise a pulsed laser source. The pulsed laser source may emit laser pulses having a duration shorter than 10 fs, shorter than 100 fs, shorter than 1 ps, shorter than 10 ps, shorter than 100 ps, shorter than 1 ns, shorter than 10 ns, shorter than 100 ns, shorter than 1 µs, shorter than 10 µs, shorter than 100 µs, or shorter than 1 ms. The pulsed laser source may emit laser pulses having a duration lying in a range defined by any two of the preceding values. In some cases, the pulsed laser source may emit laser pulses having a duration within the range from about 1 fs to about 100 µs. In some cases, the pulsed laser source may emit laser pulses having a duration within the range from about 100 ns to about 10 µs. The pulsed laser source may emit laser pulses having an adjustable duration.

The pulsed laser source may emit laser pulses with a repetition rate of less than 1 kHz, less than 10 kHz, less than 100 kHz, less than 1 MHz, less than 10 MHz, less than 100 MHz, or less than 1 GHz. The pulsed laser source may emit laser pulses with a repetition rate lying in a range defined by any two of the preceding values. In some cases, the pulsed laser source may emit pulses with a repetition rate within the range from about 10 KHz to about 1 MHz. In some cases, each pulse may produce less than 1 nJ, less than 10 nJ, less than 100 nJ, less than 1 µJ, less than 10 µJ, less than 100 µJ, less than 1 mJ, or less than 10 mJ of energy. Each pulse may produce an energy lying in a range defined by any two of the preceding values. In some cases, each pulse may produce an energy lying in the range from about 100 nJ to about 1 mJ. The pulsed laser source may emit a peak power in the range from 0.1 W to $10^7$ W.

The pulsed laser source may be a fiber laser source. The pulsed laser source may be a pulse-on-demand fiber laser source. The pulsed laser source may be a master oscillator fiber amplifier (MOPA) laser source. The pulsed laser source may be a doped fiber laser source. The pulsed laser source may be a rare earth ion doped fiber laser source. The pulsed laser source may be a ytterbium doped fiber laser source. The pulsed laser source may be a laser utilizing a doped crystal gain medium. The pulsed laser source may be a laser utilizing a neodymium-doped crystal gain medium. The pulsed laser source may be a Nd:YAG laser. The pulsed laser source may be a Nd:YVO$_4$ laser. The pulsed laser source may be a semiconductor laser. The pulsed laser source may be a diode laser. The pulsed laser source may be a vertical cavity surface emitting laser (VCSEL). The pulsed laser source may be a VCSEL array. The pulsed laser source may be a gas laser. The pulsed laser source may be a CO$_2$ laser. The pulsed laser source may be an excimer laser. The pulsed laser source may employ Q-switching. The pulsed laser source may employ mode locking. The pulsed laser source may be any pulsed laser source as is known to one having skill in the art.

The pulsed laser source may direct a laser pulse to a microchannel in response to a signal from electronic circuitry in response to intensities of light detector at each of the plurality of detectors. The pulse may be directed to the microchannel using an acousto-optical modulator (AOM), electro-optic modular (EOM), or any modulation device as may be known to one having skill in the art. For instance, the modulation device may be configured to pass the zero-order diffracted beam only in response to a signal that the extraction laser should remove a cell from a microchannel; at all other times, the modulation device may be configured to pass the first-order diffracted beam or higher-order diffracted beam. In some cases, the pulsed laser may produce pulses only in response to a signal that the extraction laser should remove a cell from a microchannel. For instance, a doped fiber laser may be operated in a reverse-biased configuration until receiving a signal to direct a pulse to the microchannel; upon receiving the signal to direct a pulse to the microchannel, the doped fiber laser may be operated in the forward-biased configuration.

The extraction laser may be directed to a galvonometer scanner block 1440. The galvonometer scanner block may be configured to rapidly scan light from the extraction laser along a curved focal plane perpendicular to its axes of rotation. The galvonometer may be scanned until receiving a signal from the circuitry to fire a laser pulse at a desired firing position. The galvonometer scanner block may be configured to wait for a signal from the circuitry before directing the extraction laser to a desired firing position. Following direction of the extraction beam by the galvonometer scanner block, F-theta relays lenses 1450 and 1452 produce a focal plane that is substantially flat. After reflection from the galvonometer scanner block and refraction through the F-theta lenses, light from the extraction laser is directed to the cassette 100. The F-theta lenses may be configured to focus the plurality of extraction beams to a microchannel in the cassette. When the extraction laser is directed to a microchannel, energy from the laser causes cavitation of the liquid sample in which a cell is suspended. This causes the removal of the cell from the microchannel.

The system may be configured to scan the extraction beam. In some cases, the system may be configured to scan the microchannels at a rate of more than 10,000 channels per second, more than 50,000 channels per second, more than 100,000 channels per second, more than 500,000 channels per second, more than 1,000,000 channels per second, more than 5,000,000 channels per second, more than 10,000,000 channels per second, more than 50,000,000 channels per second, or more than 100,000,000 channels per second. The system may be configured to scan the microchannels at a rate lying in a range defined by any two of the preceding values. In some cases, the system may be configured to scan the microchannels at a rate within a range from about 3,000 to about 300,000,000 channels per second.

System 1400 may scan the substrate at a rate greater than 1,000,000 microchannels per second, greater than 2,000,000 microchannels per second, or greater than 3,000,000 microchannels per second. System 1400 may scan the substrate at a rate that is within a range defined by any two of the preceding values. System 1400 may extract target particles from the substrate at a rate greater than 500,000 microchannels per second, greater than 600,000 microchannels per second, greater than 700,000 microchannels per second, greater than 800,000 microchannels per second, greater than 900,000 microchannels per second, or greater than 1,000,000 microchannels per second. System 1400 may extract target particles at a rate that is within a range defined by any two of the preceding values. System 1100 may extract the target particles such that a collection of extracted target particles has a purity greater than 90%, greater than 95%, or greater than 99%. System 1400 may extract the target particles such that the collection of extracted target particles has a purity that is within a range defined by any two of the preceding values.

Though shown as forming a single device in FIG. 14, system 1400 may be configured such that the fluorescence subsystem (comprising elements 1410, 1420, 1422, 1424, 1460, 1470, 1480, 1482, 1484, and 1490) are arranged as a fluorescence device and the extraction subsystem (comprising elements 1430, 1440, 1450, 1452, 1460, and 1470) are arranged as an extraction device. In such an arrangement, the substrate 100 may be subjected to a fluorescence analysis as described herein using the fluorescence device. Following the fluorescence analysis, the substrate may be transferred to the extraction device for extraction of locations of interest on the substrate identified during the fluorescence analysis. Proper alignment of the substrate in each of the fluorescence device and the extraction device may be achieved by referring to one or more fiducial markers on the substrate. In some cases, arranging system 1400 on two devices may require duplication of one or more elements of system 1400.

For instance, elements 1460 and 1470 may be required on both the fluorescence device and the extraction device.

Alternative Fluorescence Detection System

Figure 17:
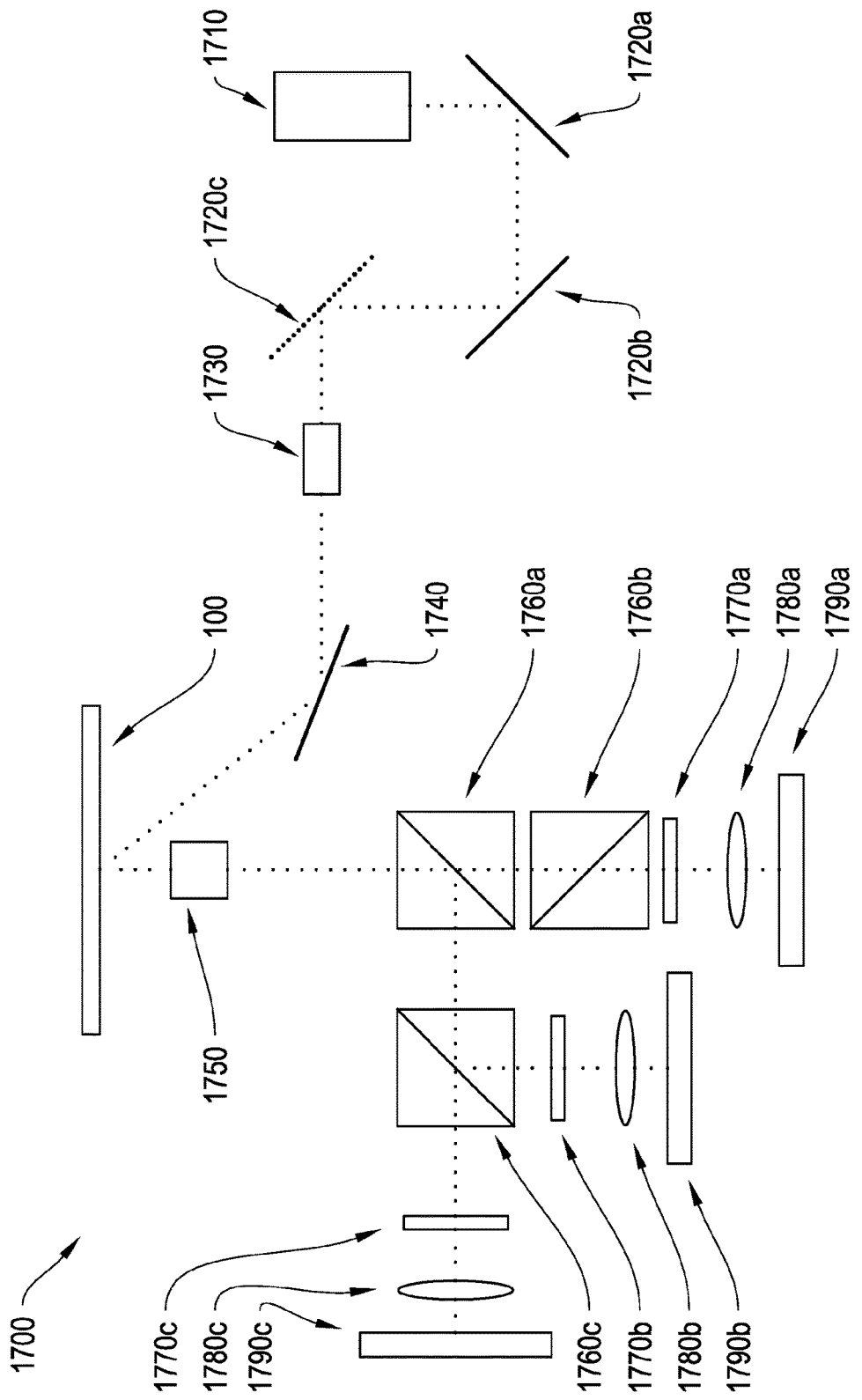
FIG. 17 is a schematic for an alternative fluorescence detection system.

FIG. 17 shows a schematic for an alternative fluorescence detection system 1700. The system 1700 may be used in place of any other fluorescence detection system described herein. For instance, the system 1700 may be used in place of any subset of the set of components 1110, 1112, 1120, 1122, 1124, 1132, 1150, 1160, 1162, 1164, 1170, and 1172 of FIG. 11, any subset of the set of components 1110, 1112, 1120, 1122, 1124, 1140, 1150, 1160, 1162, 1174, 1170, and 1172 of FIG. 12, any subset of the set of components 1110, 1112, 1120, 1122, 1124, 1140, 1150, 1164, 1166, 1168, 1170, and 1172 of FIG. 13, or any subset of the set of components 1410, 1420, 1422, 1424, 1460, 1470, 1480, 1482, 1484, and 1490 of FIG. 14.

In contrast to certain epifluorescence microscope systems, the system 1700 may operate by sending excitation light along an optical path that does not pass through an objective lens and by collecting emitted fluorescence light through the objective lens. The system 1700 may comprise an excitation light source 1710. The excitation light source may be any excitation light source described herein. For instance, the excitation light source may be any excitation laser source described herein. The excitation light source may produce light at any wavelength described herein.

The system 1700 may comprise one or more mirrors for directing light from the excitation light source to a beam expander 1730. For instance, the system may comprise mirrors 1720a, 1720b, and 1720c. Though shown as comprising three mirrors in FIG. 17, the system may comprise any number of mirrors for directing light to the beam expander, such as 1, 2, 3, 4, 5, 6, 7, 8, 9, 10, or more than 10 mirrors. The mirrors may comprise one or more coatings for enhancing reflectivity, such as one or more dielectric coatings as are known to one having skill in the art.

The beam expander 1730 may expand the beam waist of the excitation light by a factor of 1, 2, 5, or 10. The beam expander may expand the beam waist of the excitation light by a factor that is within a range defined by any two of the preceding values.

The beam expander may direct expanded excitation light to a scanning mechanism 1740. The scanning mechanism may be similar to any scanning mechanism described herein. For instance, the scanning mechanism may comprise a polygon mirror as described herein. The scanning mechanism may comprise a galvanometer as described herein. The scanning mechanism may direct the excitation light to one or more locations on a substrate 100. The substrate may be any substrate described herein (such as one or more microchannels on a microchannel array described herein).

The scanning mechanism may direct the excitation light to the one or more locations on the substrate such that the excitation light does not pass through an objective lens 1750. The scanning mechanism may direct the excitation light to the one or more locations on the substrate such that the excitation light hits the one or more locations on the substrate at an angle to the normal. Configuring the system in this manner may reduce noise associated with the fluorescence system. For instance, such a configuration may reduce speckle noise or noise associated with auto-fluorescence of the objective lens. In some embodiments, such a configuration reduces background fluorescence by 20% or more. The configuration may reduce background fluorescence by 30% or more, 40% or more, 50% or more, 60% or more, or 70% or more. In an exemplary embodiment, such a configuration reduces background fluorescence by 60% or more. Configuring the system in this matter may reduce speckle noise detected by the light detector by 30% or more, 40% or more, 50% or more, 60% or more, or 70% or more. In an exemplary embodiment, the configuration reduces speckle noise detected by the light detector by 50% or more.

The excitation light may interact with the locations on the substrate to produce fluorescence light, as described herein.

The objective lens 1750 may collect the fluorescence light. The objective lens may comprise any objective lens described herein. The objective lens may direct fluorescence light to one or more beamsplitters 1760a, 1760b, and 1760c, one or more filters 1770a, 1770b, and 1770c, one or more lenses (such as one or more tube lenses) 1780a, 1780b, 1780c, and one or more light detectors (such as photodiodes, CCD cameras, or CMOS cameras) 1790a, 1790b, and 1790c. Though shown as comprising three beamsplitters, three filters, three lenses, and three light detectors in FIG. 17, the fluorescence detection system 1700 may comprise any number of beamsplitters, such as 1, 2, 3, 4, 5, 6, 7, 8, 9, 10, or more than 10 beamsplitters, any number of filters, such as 1, 2, 3, 4, 5, 6, 7, 8, 9, 10, or more than 10 filters, any number of lenses, such as 1, 2, 3, 4, 5, 6, 7, 8, 9, 10, or more than 10 lenses, and any number of light detectors, such as 1, 2, 3, 4, 5, 6, 7, 8, 9, 10, or more than 10 light detectors. The beamsplitters may comprise any beamsplitters described herein. The filters may comprise any filters described herein. The lenses may comprise any lenses described herein. The light detectors may comprise any light detectors described herein.

Digital Processing Device

In some embodiments, the platforms, systems, media, and methods described herein include a digital processing device, or use of the same. In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 16:
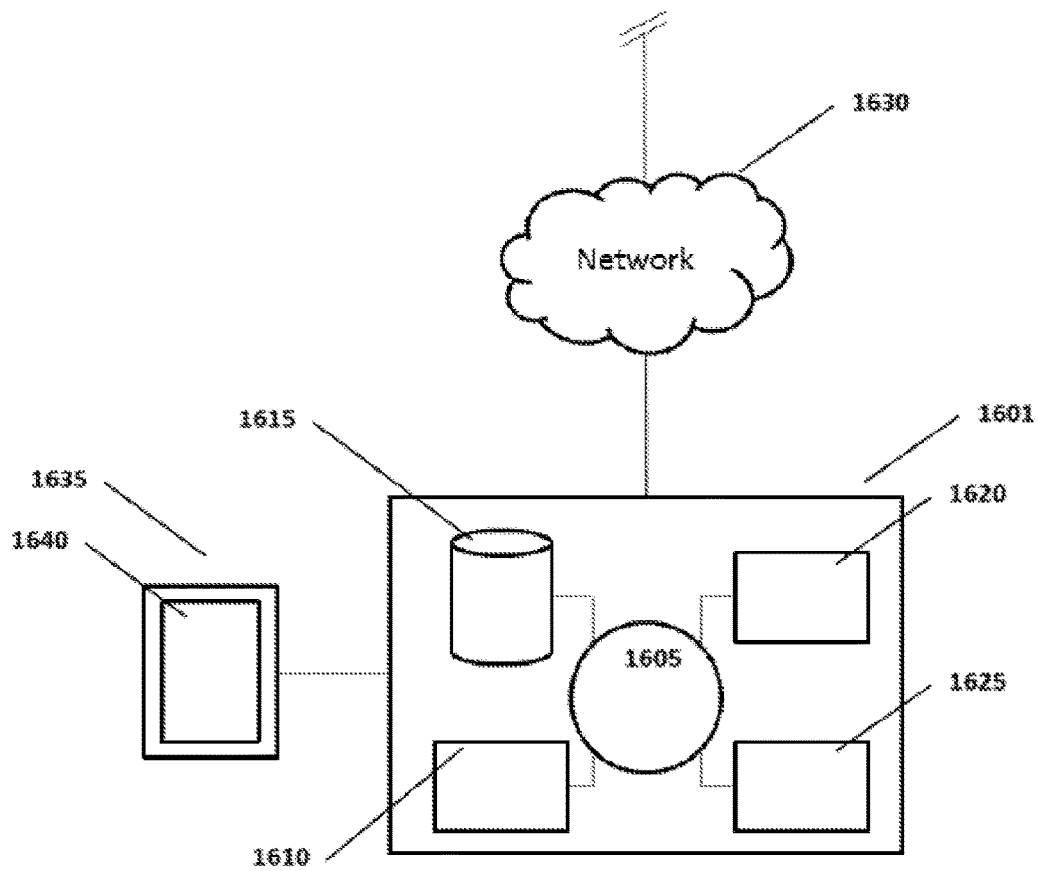
FIG. 16 shows an exemplary digital processing device programmed or otherwise configured to operate a laser scanning cell sorting device.

Referring to FIG. 16, in a particular embodiment, an exemplary digital processing device 1601 is programmed or otherwise configured to operate a laser scanning cell sorting device. The device 1601 can regulate various aspects of the laser scanning cell sorting of the present disclosure, such as, for example, performing processing steps. In this embodiment, the digital processing device 1601 includes a central processing unit (CPU, also "processor" and "computer processor" herein) 1605, which can be a single core or multi core processor, or a plurality of processors for parallel processing. The digital processing device 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The digital processing device 1601 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the device 1601, can implement a peer-to-peer network, which may enable devices coupled to the device 1601 to behave as a client or a server.

Continuing to refer to FIG. 16, the CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and write back. The CPU 1605 can be part of a circuit, such as an integrated circuit. One or more other components of the device 1601 can be included in the circuit. In some cases, the circuit is an application specific integrated circuit (ASIC) or a field programmable gate array (FPGA).

Continuing to refer to FIG. 16, the storage unit 1615 can store files, such as drivers, libraries and saved programs. The storage unit 1615 can store user data, e.g., user preferences and user programs. The digital processing device 1601 in some cases can include one or more additional data storage units that are external, such as located on a remote server that is in communication through an intranet or the Internet.

Continuing to refer to FIG. 16, the digital processing device 1601 can communicate with one or more remote computer systems through the network 1630. For instance, the device 1601 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1315 can be precluded, and machine-executable instructions are stored on memory 1610.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

EXAMPLES

Example 1: Macro-Gel Isolation

As presented in FIG. 6, opaque particles and cells may be separated in a microchannel of a substrate in order to protect the cells from electromagnetic radiation during extraction. First, approximately 1 g of agarose (Sigma-Aldrich, Cat No: A9539) was added to approximately 100 mL of distilled water. The mixture was heated in a microwave oven and the mixture was stirred intermittently to dissolve the agarose. Opaque beads (Dynabeads M-270 Epoxy, Thermo Fisher, Cat No: 14301) were added to the mixture and the beads were mixed to make a uniform distribution. The mixture was applied onto the surface of a micropore array and the mixture was allowed to enter into the pores by surface tension. The mixture in the pores was allowed to cool for at least approximately 20 min at room temperature and to set inside the pores to make a gel infused micropore array. The gel infused micropore array may be stored in approximately 4° C. for future use. Then, a reservoir on one side of the gel infused micropore array was created and buffer QG (QIAGEN, Cat No: 19063) was added. Buffer QG was allowed to sit and dissolve a portion of the agarose on one side of the pore for approximately 5 min. The QG buffer was washed off with PBS (Thermo Fisher, Cat No: 10010023) and with 2% BSA (VWR, Cat No. 97063-626), and this step was repeated twice. A cell suspension solution was added to the side of the pore that was dissolved ("etched out"). The cell suspension solution was allowed to sit for approximately 10 min and allowed the cells to sediment into the pores. The micropore array was washed twice with PBS and 2% BSA solution to get rid of extra cells stuck to the surface of the pore. The pore was inverted and allowed to sit for approximately 10 min. The cells sediment on the meniscus due to gravity.

Example 2: Micro-Gel Isolation

As presented in FIG. 7B, opaque particles and cells may be separated in a microchannel of a substrate in order to protect the cells from electromagnetic radiation during extraction. First, cells in PBS and 2% BSA were added to beads that have a magnetic core and an agarose shell (Cube-BioTech) in a volume of approximately 20 µL of 50% (V/V) per 50 µL of cell suspension. The suspension was loaded onto a micropore array and allowed the suspension to enter into the pores by capillary action. A strong neodymium magnet (cylindrical shape diameter 6.5 mm, length 25 mm, strength N52) was applied for approximately 5 min to the top of the array in order to cause the magnetic beads to settle on the upper meniscus. Then, the magnet was removed. The cells and beads were allowed to settle for approximately 10 min, and allowed a distinct layer of cells to settle on the lower meniscus and a layer of beads to settle on the top.

Example 3: In-Pore Spacer

As presented in FIG. 8A, magnetic particles and cells may be separated in a microchannel of a substrate in order to protect the cells from electromagnetic radiation during extraction. First, cells in PBS and 2% BSA were added to approximately 10 µL of $0.25 \times 10^9$ beads/mL in 100 µL, of transparent silica (Bangs Laboratories, Inc., Cat No: SS05N, size 3.48 µm) and approximately 2 µL of $2 \times 10^9$ beads/mL in 100 µL of opaque magnetic beads (Dynabeads® M-270 Epoxy, Thermo Fisher, CAT No: 14301). The suspension was loaded onto a micropore array and allowed the suspension to enter into the pores by capillary action. A strong neodymium magnet (cylindrical shape diameter 6.5 mm, length 25 mm, strength N52) was applied for approximately 5 min to the top of the array in order to cause the magnetic beads to settle on the upper meniscus. Then, the magnet was removed. The cells and beads were allowed to settle for approximately 10 min, and allowed a distinct layer of cells and transparent silica beads to settle on the lower meniscus and a layer of beads to settle on the top.

Example 4: Sequential Loading

As presented in FIG. 9A, cells may be loaded into an array sequentially with opaque beads or loaded in a mixed batch in order to quantify cells. First, load the micropore array with cells suspended in PBS and 2% FBS. Allow the cells to settle for 10 min. Then, add beads to the micropore array with a concentration between 1 to 2 billion per mL. Allow the contents of the microarray to sit for at least 10 min to allow the beads to settle into the pores and rest on top of the cells.

Example 5: Hanging Bead

Put 60 µL of cell suspension on the bottom of a clean glass slide, so that the droplet is inverted. The droplet stays in place due to the hydrophilicity and the surface tension balancing out the gravitational pull. Allow the droplet to settle for 10 min. Apply the micropore array to the hanging drop. The micropore array may be applied with a Z-translation stage or by hand. The first end, middle portion, and second end of the micropore array should be substantially in the same plane and flat when applied to the hanging drop. Allow the cell suspension to enter the micropore array by capillary action. Put a PDMS reservoir on the side that touched the hanging drop. Fill up the reservoir with 100 µL of buffer for hydration. Settle for 10 min before imaging.

Example 6: Flooding

The PDMS reservoir (diameter 7 mm and height 3 mm) was fixed to the top of a micropore glass array. Approximately 60 µm of cell suspension (of different concentration) was added to the top of the micropore glass array. Approximately 10 µL of cell suspension was taken out from the top of a micropore glass array. The PDMS reservoir was filled with approximately 100 µL, of buffer to keep the pores hydrated. Settled for approximately 10 min before imaging.

Example 7: Sonication

Approximately 100 µL of buffer (PBS+0.2% BSA) was added to a 20 µm glass microchip. Remove approximately 20 µL of buffer from the PDMS reservoir. Approximately 15 µL of re-suspended beads was added at a known concentration. Waited for approximately 10 min. Imaged with microscopy. The Tide sonicator (sonicator frequency 40 KHz) was applied on the side of the chip. Waited for approximately 10 min. Imaged with microscopy. A strong neodymium magnet was applied at the bottom of the chip to pull the beads to the bottom. Imaged with microscopy.

Example 8: Fluorescence Displacement

A micropore array was loaded with cells and COMPEL™ beads (5 µL of $0.6 \times 10^9$ in 100 µL of cell suspension, Bangs Laboratories, Inc., Cat No: UMC3F, size 2.85 µm, fluorescent emission: green) suspended in PBS and 2% FBS. A strong neodymium magnet (cylindrical shape diameter 6.5 mm, length 25 mm, strength N52) was added at top of the array for approximately 5 min to cause the magnetic beads to settle on the upper meniscus. The magnet was removed and allowed the cells and beads to settle for approximately 10 min. Imaged the cells settled on the lower meniscus.

Example 9: Extraction

Figure 15:
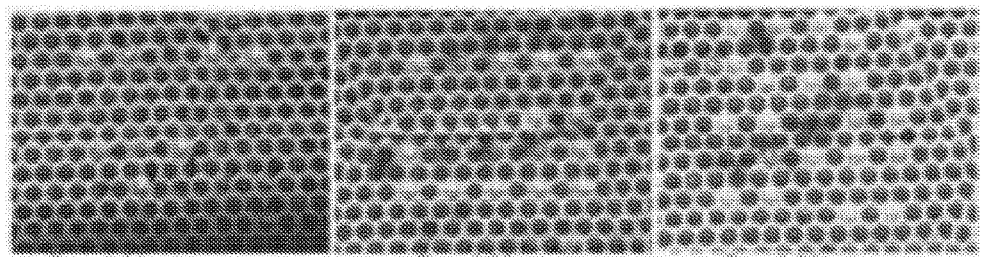
FIG. 15 shows the optimal pulse power settings for laser extraction of cells from a microchannel array.

FIG. 15 shows the optimal pulse power settings for laser extraction of cells from a microchannel array. A study was conducted to determine extraction laser settings that would allow the expulsion of fluid from desired wells within a microchannel array. The study was conducted using a IPG Photonics YLPN-1-1x120-100-M adjustable pulse duration nanosecond ytterbium-doped fiber laser. The laser was focused to a beam diameter of 6.55 µm and scanned across a microchannel array using a SCANLab hurrySCAN II 14 galvonometer scanner. The extraction light was focused onto a flat plane using a Linos F-Theta-Ronar lens with a 163 mm focal length. Direction of the extraction laser pulses was controlled using a Lanmark Maestro 3000 LEC-1 Ethernet smart controller with a built-in IPG Photonics laser extension board. The controller was programmed using the Lanmark WinLase LAN v 5.1.9.17 software. The pulse duration was arbitrarily set to 4 ns. The pulse repetition rate was set at 100 kHz.

Trials were performed with varying levels of average laser power. As shown in the left pane of FIG. 15, an average laser power of 2.0 W resulted in only marginal expulsion of fluid from desired microchannels (light spots in the array of microchannels). As shown in the right pane, an average laser power of 3.3 W resulted in the complete expulsion of fluid from the desired microchannels. As shown in the central pane, the optimal average laser power was determined to be 2.3 W, corresponding to an energy of 23 µJ for each laser pulse.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A cassette for detecting and sorting target particles, the cassette comprising:
   a substrate with a first surface and a second surface and a plurality of microchannels extending from said first surface to said second surface;
   a first housing configured to receive said substrate wherein said first housing comprises an internal surface to receive a target particle released from said substrate;
   a second housing coupled to said first housing in a manner wherein said first and second housing together encapsulate said substrate and wherein said first or second housing further comprises a first fill port; and
   a transmissive portion located in one or each of said first housing and said second housing, wherein said transmissive portion permits transmission of electromagnetic radiation from outside of said cassette to said substrate,
   wherein the cassette further comprises a hydration membrane positioned to contact said substrate or positioned adjacent to said substrate, or a sample well in fluid communication with said first fill port, wherein said sample well is configured to load a sample material mixture into said microchannels of said substrate, and wherein said sample well is movable across said first surface of said substrate.

2. The cassette of claim 1, wherein said transmissive portion is at least partially transparent to a wavelength in the range of about 250 nm to 1600 nm.

3. The cassette of claim 1, wherein said transmissive portion is located in said second housing.

4. The cassette of claim 1, wherein said first fill port is configured to receive a sample material mixture into said cassette.

5. The cassette of claim 1, wherein said second housing comprises said first fill port.

6. The cassette of claim 1, wherein said first or second housing further comprises a release port.

7. The cassette of claim 6, wherein said release port is in fluid communication with said internal surface to permit transfer of said target particles out of said release port in said cassette.

8. The cassette of claim 6, wherein said first housing comprises said release port.

9. The cassette of claim 1, wherein the first housing and second housing are coupled irreversibly as a single housing unit.

10. The cassette of claim 1, wherein said substrate comprises glass.

11. The cassette of claim 1, wherein said plurality of microchannels is from about 1 million to about 100 billion microchannels.

12. The cassette of claim 1, wherein said plurality of microchannels have an average internal diameter of about 50 nm to about 500 µm.

13. The cassette of claim 1, wherein the distance from said first surface to said second surface of said substrate is on average from about 10 µm to about 1 mm.

14. The cassette of claim 1, wherein the cassette comprises the sample well in fluid communication with said first fill port, wherein said sample well is configured to load a sample material mixture into said microchannels of said substrate, and wherein said sample well is movable across said first surface of said substrate.

15. The cassette of claim 1, wherein said first or second housing further comprise a second fill port.

16. The cassette of claim 15, wherein said first or second fill port is in fluid communication with said internal surface of said first housing.

17. The cassette of claim 1, wherein said first or second housing further comprise a third fill port.

18. The cassette of claim 1, wherein said cassette further comprises the hydration membrane positioned to contact said substrate or positioned adjacent to said substrate.

19. The cassette of claim 18, wherein said first, second, or third fill port is in fluid communication with said hydration membrane.

20. The cassette of claim 1, wherein said internal surface further comprises a collection well.

21. The cassette of claim 20, wherein said collection well is in fluid communication with said release port.

22. The cassette of claim 1, wherein said first or second housing further comprises a metal frame which is affixed to said first or second housing and said first or second surface of said substrate and applies tension across the surface of said substrate.

23. The cassette of claim 1, wherein said target particles comprise cells.

24. The cassette of claim 1, wherein said cassette is sterilized before use.

25. The cassette of claim 1, wherein said substrate has dimensions of 3 mm×3 mm×0.3 mm to 5000 mm×15000 mm×1000 mm.

\* \* \* \* \*